(12) United States Patent
Salman

(10) Patent No.: US 10,260,956 B2
(45) Date of Patent: Apr. 16, 2019

(54) TIME AND/OR TEMPERATURE SENSITIVE DEVICES AND METHODS OF USE THEREOF

(71) Applicant: Freshpoint Quality Assurance Ltd., Haifa (IL)

(72) Inventor: Husein Salman, Ghajar Village (IL)

(73) Assignee: FRESHPOINT QUALITY ASSURANCE LTD., Haifa (IL)

( * ) Notice: Subject to any disclaimer, the term of this patent is extended or adjusted under 35 U.S.C. 154(b) by 562 days.

(21) Appl. No.: 14/571,074

(22) Filed: Dec. 15, 2014

(65) Prior Publication Data

US 2015/0308901 A1 Oct. 29, 2015

Related U.S. Application Data

(63) Continuation-in-part of application No. PCT/IL2013/050512, filed on Jun. 16, 2013.

(60) Provisional application No. 61/660,457, filed on Jun. 15, 2012, provisional application No. 61/916,237, filed on Dec. 15, 2013.

(51) Int. Cl.
*G01K 3/04* (2006.01)

(52) U.S. Cl.
CPC ..................... *G01K 3/04* (2013.01)

(58) Field of Classification Search
CPC . G01K 3/04; G01K 3/10; G01K 11/06; G01K 11/08; G01K 11/12; G01K 11/02
See application file for complete search history.

(56) References Cited

U.S. PATENT DOCUMENTS

| | | | | |
|---|---|---|---|---|
| 4,057,029 A | | 11/1977 | Seiter | |
| 4,664,056 A | * | 5/1987 | Jehanno | G01K 3/00 116/160 |
| 4,737,463 A | | 4/1988 | Bhattacharjee et al. | |
| 4,931,420 A | * | 6/1990 | Asano | G01K 3/04 374/E3.004 |
| 5,053,339 A | * | 10/1991 | Patel | G01K 3/04 116/206 |

(Continued)

FOREIGN PATENT DOCUMENTS

| | | |
|---|---|---|
| WO | 95/33991 A1 | 12/1995 |
| WO | 99/39197 A1 | 1/1999 |

(Continued)

OTHER PUBLICATIONS

Plazanet et al. "Inverse freezing in molecular binary mixtures of a-cyclodextrin and 4-methylpyridine"; May 13, 2010; Physical Chemistry Chemical Physics; Phys. Chem. Chem. Phys., 2010, 12, 7026-7031.*

*Primary Examiner* — Jonathan Dunlap
*Assistant Examiner* — Philip Cotey
(74) *Attorney, Agent, or Firm* — Browdy and Neimark, PLLC

(57) ABSTRACT

An apparatus, system and method for a time temperature indicator (TTI) which is capable of providing a summary of the time and temperature history of a good to which it is coupled, optionally including with regard to providing an indication as to whether one or more temperature thresholds have been breached. According to other embodiments, the TTI specifically provides an indication as to whether a temperature threshold at or around the freeze point has been breached, optionally even without providing a time and temperature history.

7 Claims, 72 Drawing Sheets

(56) References Cited

U.S. PATENT DOCUMENTS

| | | | |
|---|---|---|---|
| 6,042,264 | A | 3/2000 | Prusik et al. |
| 6,435,129 | B1 | 8/2002 | McDonald et al. |
| 7,490,575 | B2 | 2/2009 | Taylor et al. |
| 8,343,437 | B2 | 1/2013 | Patel |
| 9,022,648 | B2 * | 5/2015 | Vanier .................... B82Y 40/00 374/161 |
| 9,130,227 | B2 * | 9/2015 | Arsenault ........... H01M 6/5044 |
| 2006/0130734 | A1 * | 6/2006 | Koivukunnas ........... G01K 3/04 116/216 |
| 2007/0125296 | A1 * | 6/2007 | Taylor .................... G01K 3/005 116/216 |
| 2009/0123334 | A1 * | 5/2009 | Cavallini ............... G01K 11/06 422/400 |
| 2009/0301382 | A1 | 12/2009 | Patel |
| 2010/0043694 | A1 * | 2/2010 | Patel .................... G09F 3/0292 116/201 |
| 2010/0296545 | A1 | 11/2010 | Haarer et al. |
| 2012/0044970 | A1 * | 2/2012 | Arsenault ........... G01K 11/125 374/159 |
| 2013/0001940 | A1 * | 1/2013 | Arsenault ............. G02B 1/005 283/67 |
| 2013/0148690 | A1 | 6/2013 | Chan et al. |
| 2013/0287059 | A1 * | 10/2013 | Selman .................... G01K 3/04 374/104 |

FOREIGN PATENT DOCUMENTS

| | | |
|---|---|---|
| WO | 01/25472 A1 | 4/2001 |
| WO | 03044521 A1 | 5/2003 |
| WO | 03077227 A2 | 9/2003 |
| WO | 2007118933 A1 | 10/2007 |

* cited by examiner

Figure 1C
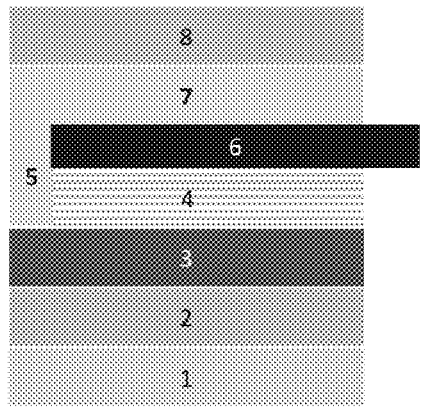
1) Back printing
2) PET
3) Aluminum
4) Front printing (pictorgams, graphics, barriers etc.)
5) Adhesive binding aluminum and etchant labels
6) Release layer (Liner)
7) Etching adhesive
8) PET
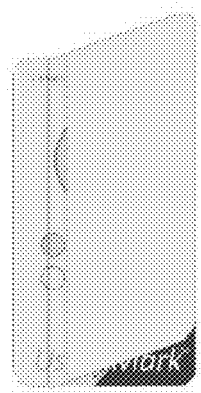
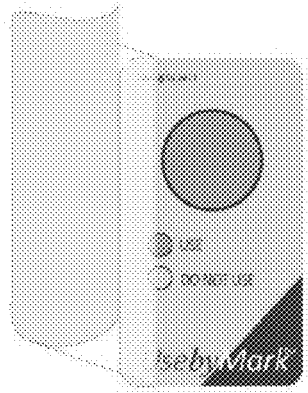
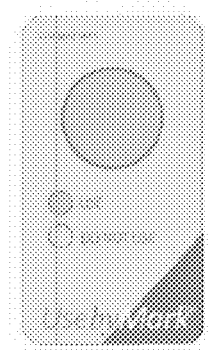
A              B              C

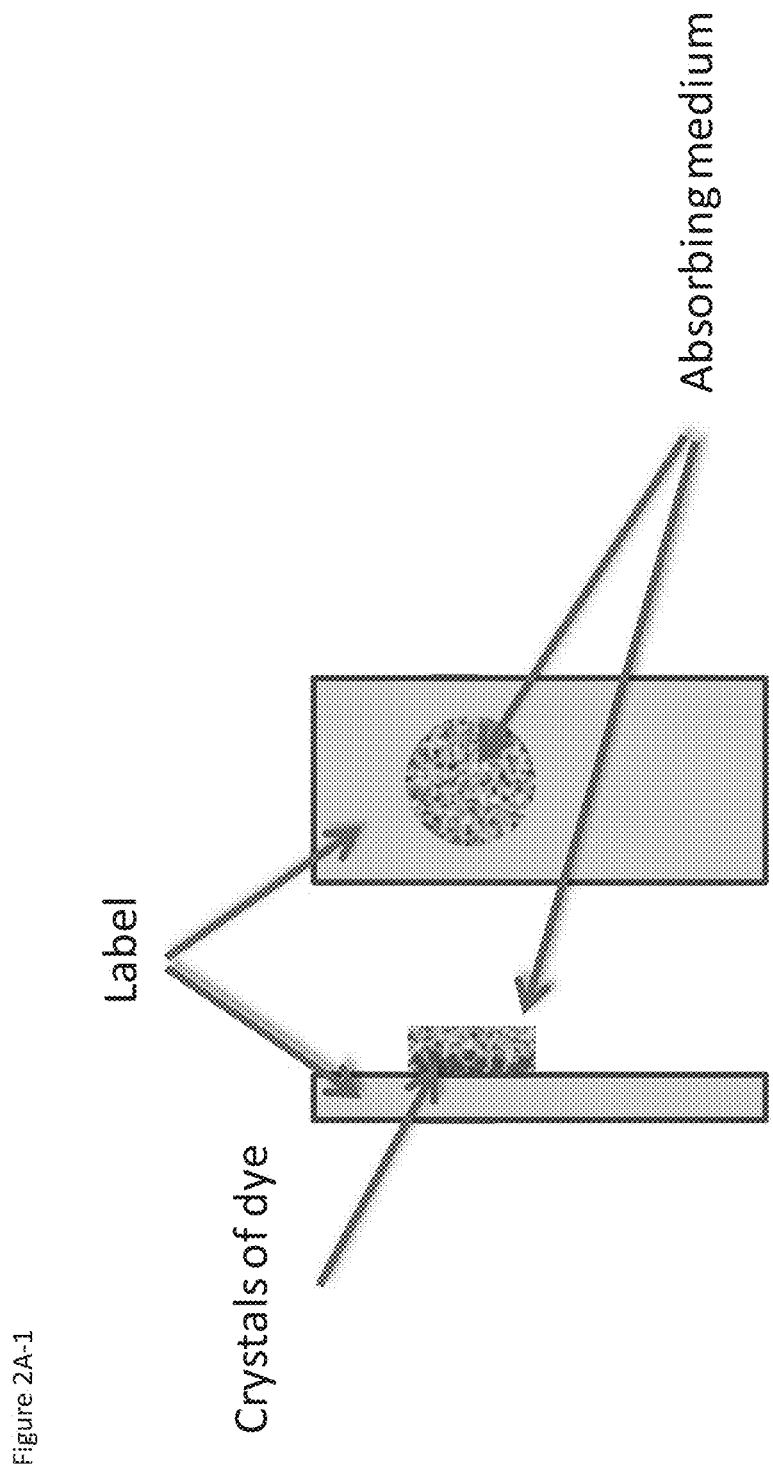

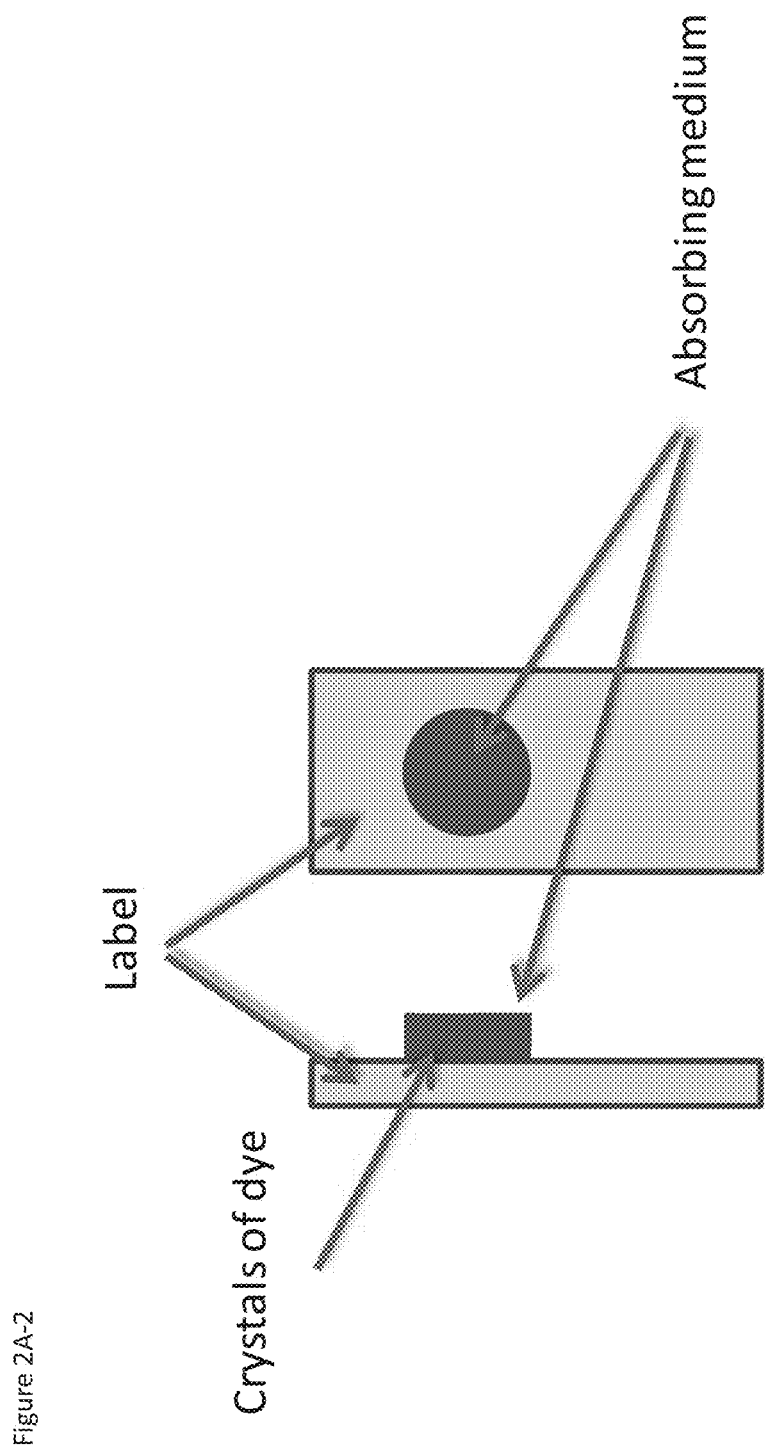

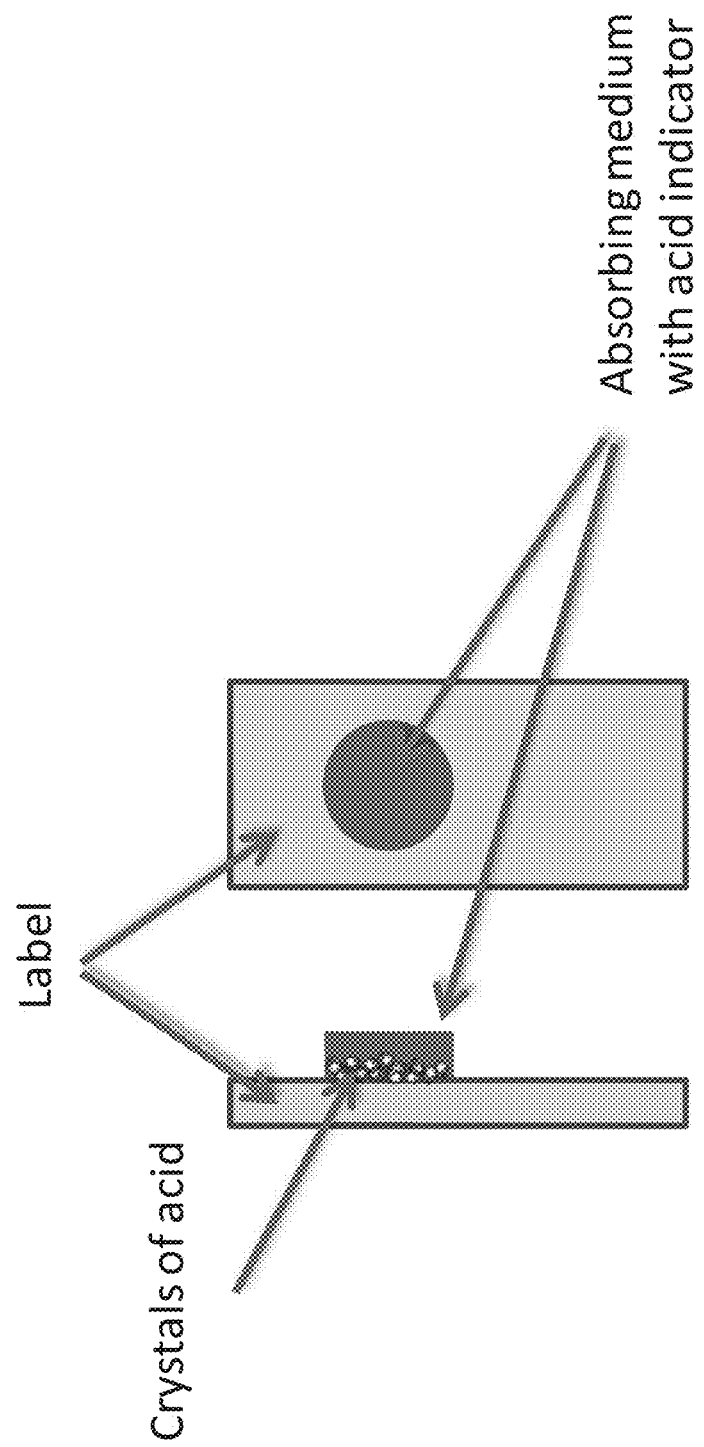

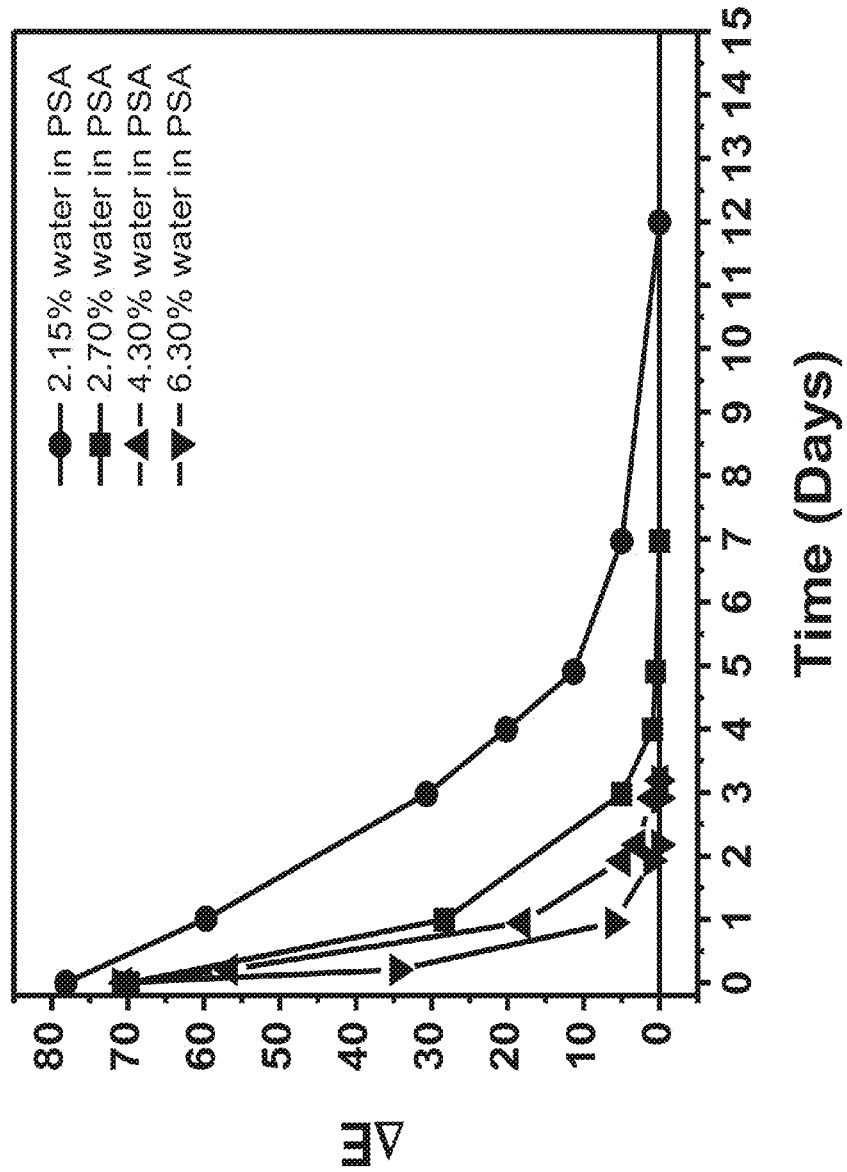
Figure 3 The lifetime of the TTI (active reactant: Al layer, OD=0.6) as a function of the water content in the PSA layer containing the etchant (passive reactant), Temp.=4C.

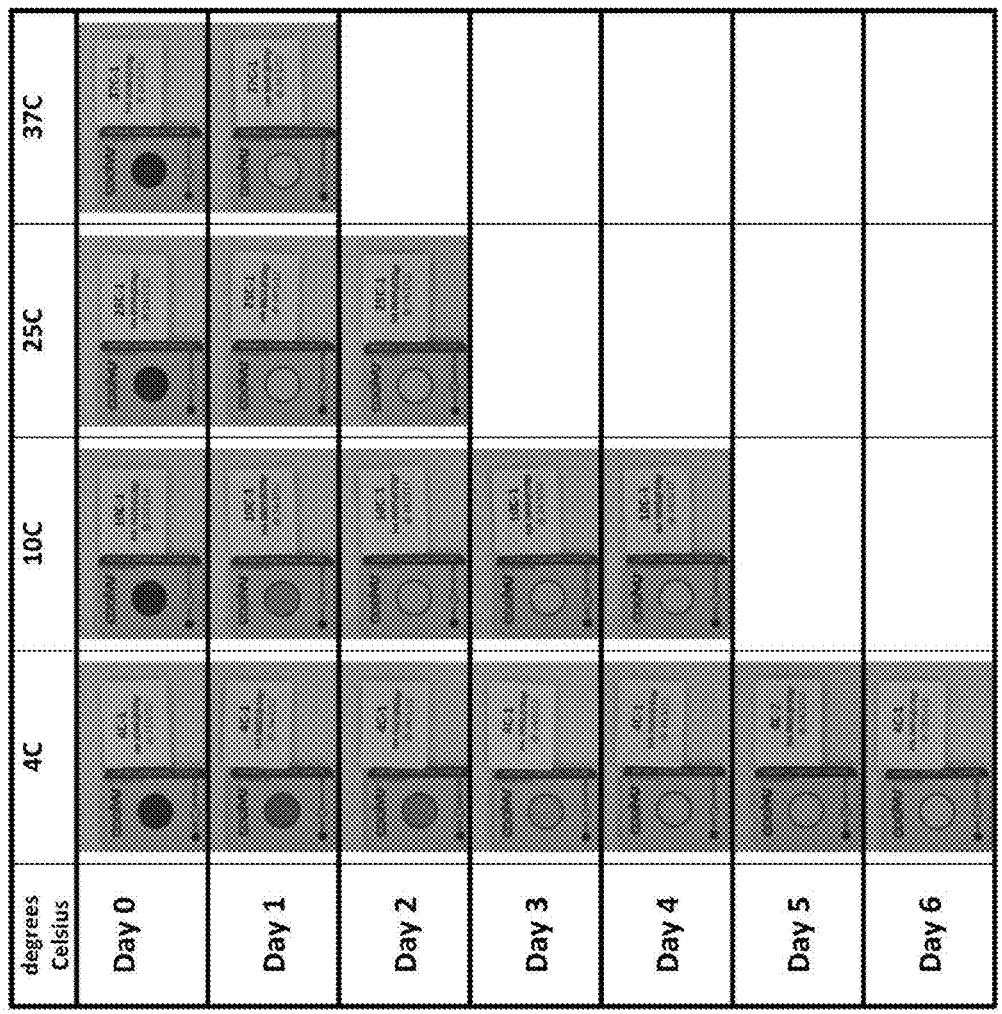
Figure 4: The color of an active spot of an aluminum (OD=0.6) based TTI having no barrier as a function of the time after activation.

Figure 5
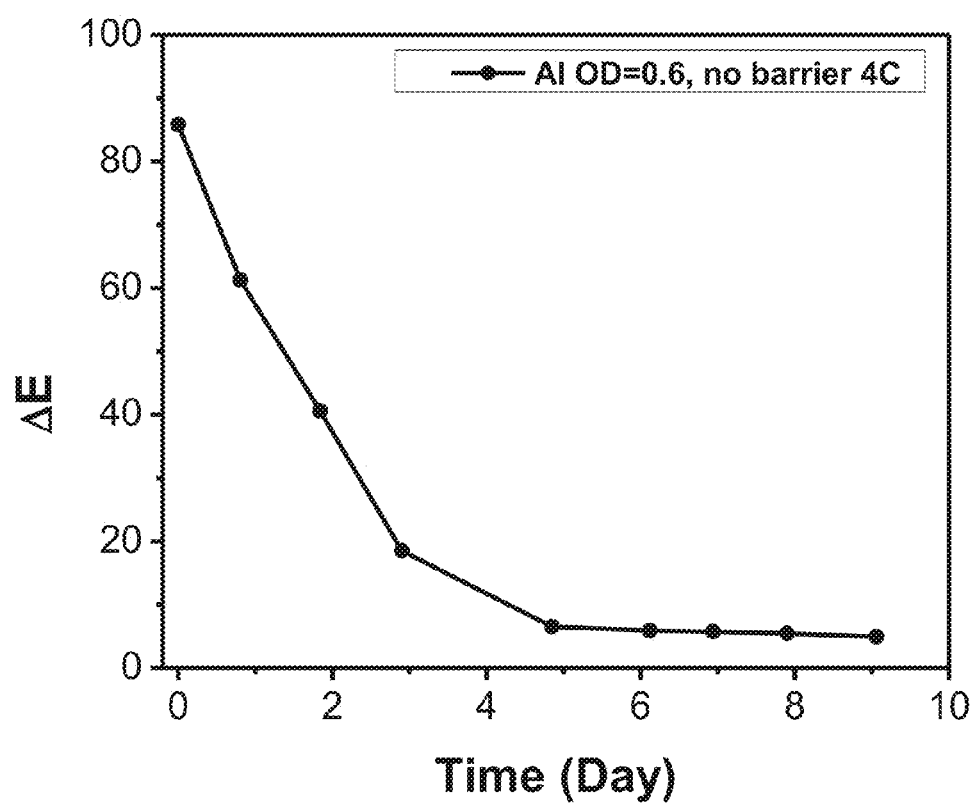
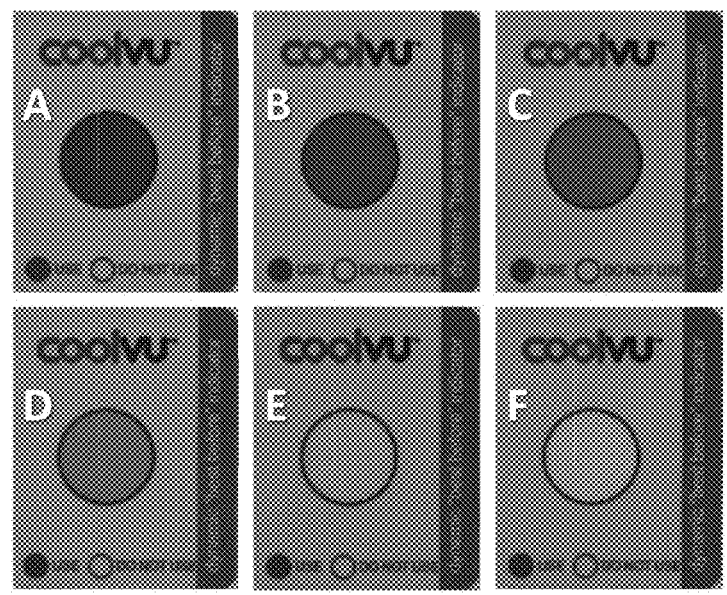

Figure 6 Left: The time to reach end point of a printed TTI as a function of the print thickness (ΣAnilox);

Figure 7: An embodiment of a three-spot time-temperature indicator having three trapezoid spots, each having a different barrier thickness, at different times after activation and at different temperatures.

Figure 8: An example of how printing series of barriers made of the same monomer composition but having different proportions yield different time-temperature behavior of the TTIs.

Figure 9: The density of H$_2$O as a function of the temperature

Figure 14
 

Figure 22
| | 37C | | 50C | |
|---|---|---|---|---|
| | with barrier | without barrier | with barrier | without barrier |
| Day 0 | 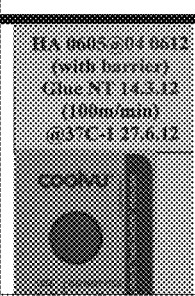<br>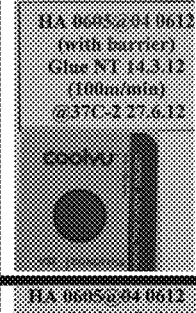 | 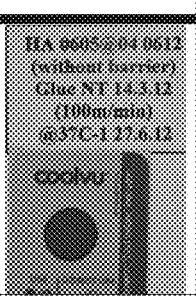<br>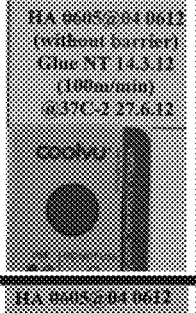 | 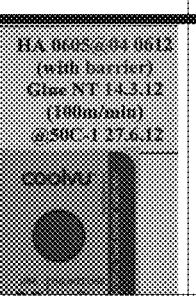<br>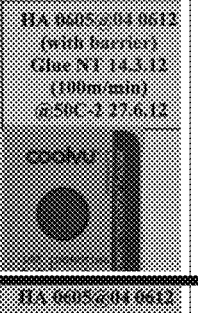 | 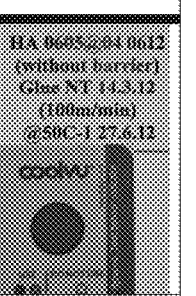<br>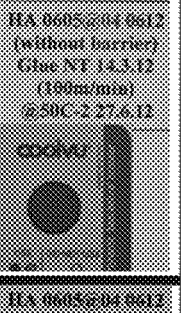 |
| Day 203 | 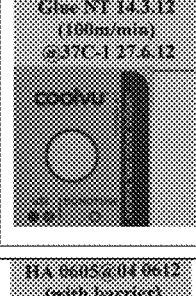 | 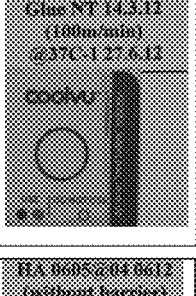 | 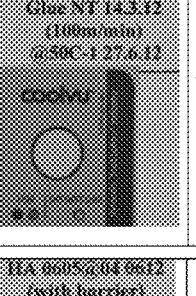 | 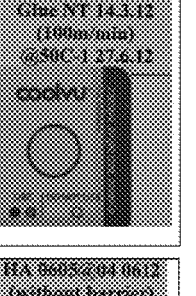 |
| | 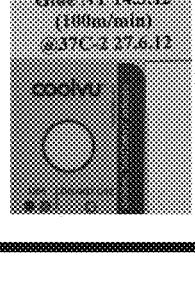 | 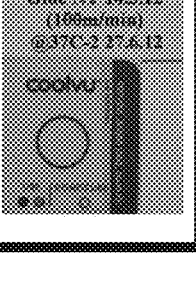 | 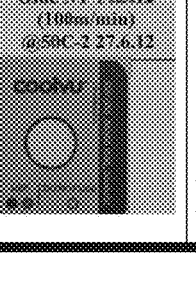 | 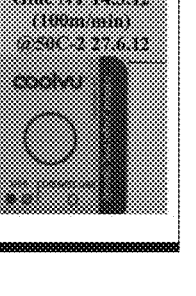 |
Activation label: Freshpoint adhesive 5% NT-14.3.12 100m/min – label)
Label: HA 0605@04 0612. With and without impervious barrier
Printed – June 2012; Kinetics: 50C and 37C started 27.6.12

Figure 25

| Ratio | | α-CD[1] | H$_2$O[2] | 2-MP[3] | Proprieties @ | | | | | |
|---|---|---|---|---|---|---|---|---|---|---|
| | | | | | 50C | 23C | 4C | 2C | 0C | -23.5C |
| 1:6:40 | 1 | 0.1094 g | 11 μl | 0.4 ml | Solid | Solid | Liquid | Liquid | | Liquid |
| | 2 | 0.1024 g | 11 μl | 0.4 ml | Solid | Solid | Liquid | Liquid | | Liquid |
| 1:6:30 | 3 | 0.1 g | 11 μl | 0.3 ml | | | | | | |
| | 4 | 0.1013 g | 11 μl | 0.3 ml | Solid | Solid | P.S* | P.S* | | Liquid |
| 1:6:20 | 5 | 0.2022 g | 22 μl | 0.4 ml | Solid | Solid | Solid | Solid | | Liquid |
| | 6 | 0.2023 g | 22 μl | 0.4 ml | Solid | Solid | Solid | Solid | | Liquid |

| | | | | 4-MP[4] | Proprieties @ | | | | | |
|---|---|---|---|---|---|---|---|---|---|---|
| 1:6:40 | 7 | 0.1 g | 11 μl | 0.4 ml | Solid | Liquid | | | | |
| 1:6:30 | 8 | 0.1 g | 11 μl | 0.3 ml | Solid | Liquid | | | | |
| 1:6:20 | 9 | 0.1 g | 22 μl | 0.3 ml | Solid | Liquid | | | | |
| 1:12:30 | 10 | 0.1 g | 22 μl | 0.3 ml | Solid | Liquid | | | | |

* P.S.=Phase separation

[1] Mw=972.84 g/mol, 100 mg=1.028×10$^{-4}$ mol

[2] Mw=18 g/mol, 11.11 mg

[3] Mw=93.13 g/mol, d=0.944 g/ml, 1.028×10$^{-4}$ mol=0.01014 ml

[4] Mw=93.13 g/mol, d=0.957 g/ml, 1.028×10$^{-4}$ mol=0.01014 ml

100: packaging
101: porous medium
102: destroyable seal
103: inverse melting material in container
104: inspection window
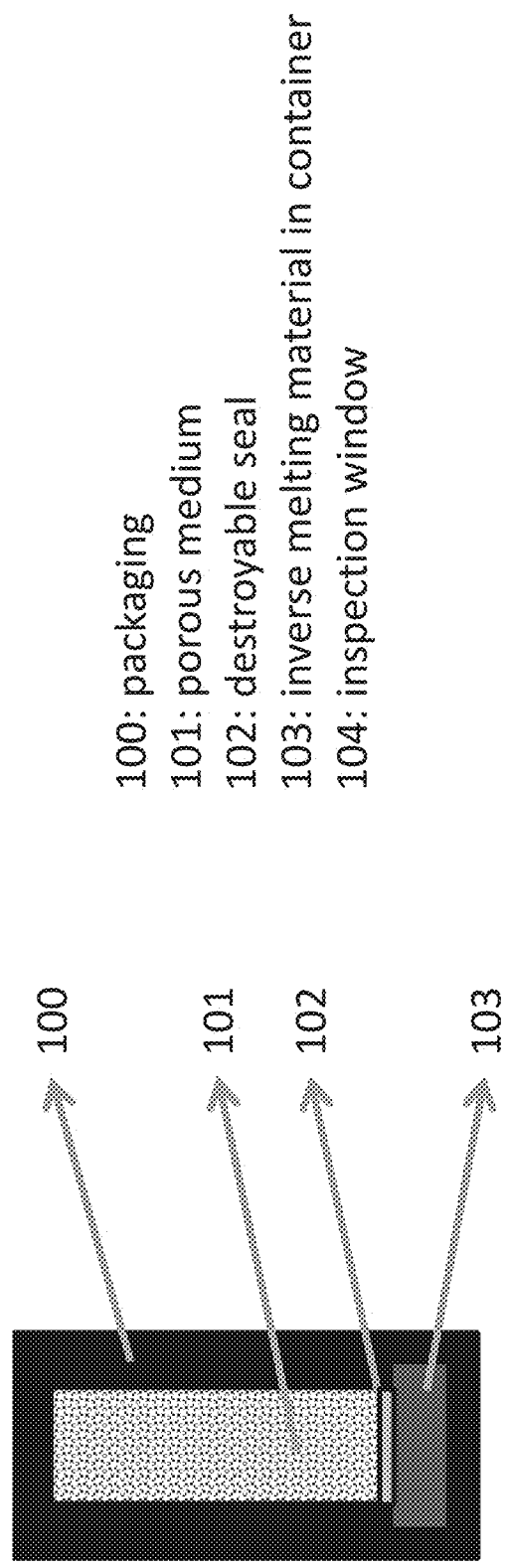
Figure 30A1
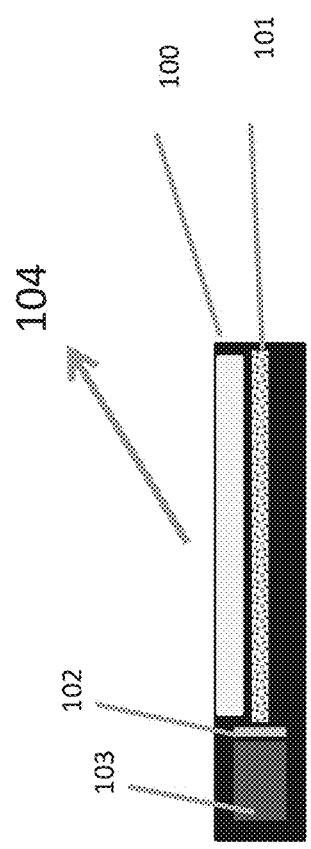
Figure 30A2

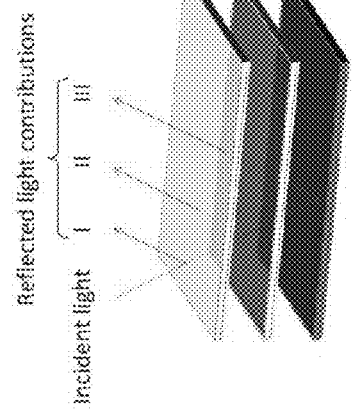
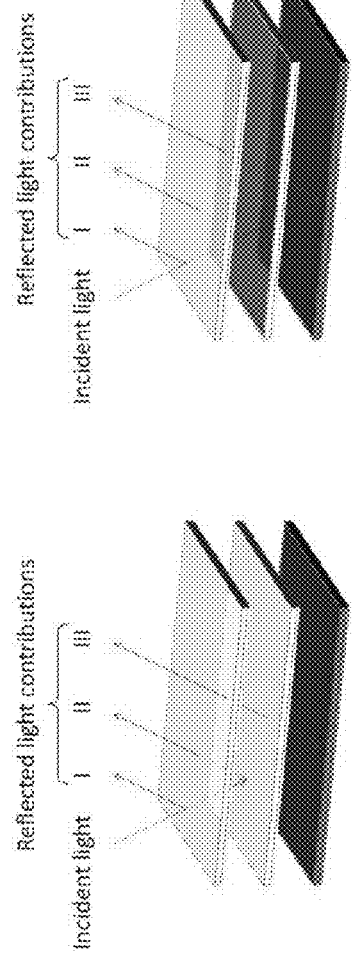
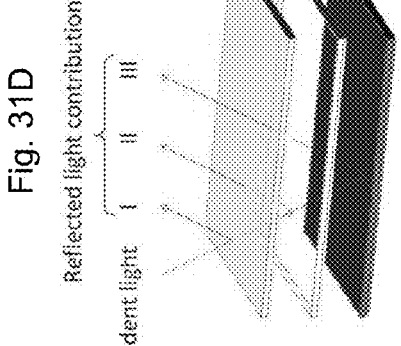
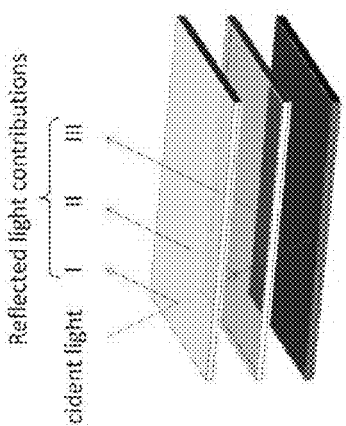

*Free product appearing in window*

TIME AND/OR TEMPERATURE SENSITIVE DEVICES AND METHODS OF USE THEREOF

FIELD OF THE INVENTION

The present invention, in some embodiments thereof, relates to temperature sensitive applied materials and devices, and, more particularly, but not exclusively, to temperature indicators, whether as a threshold, a temperature history or a combination thereof, optionally with a visually and/or instrumentally visible summary of the elapsed time-temperature profile the device had experienced, for various business applications.

BACKGROUND OF THE INVENTION

Time temperature indicators (alternatively called "time temperature integrators") are devices that are characterized by at least one changeable observable physical property that progresses at a rate that is proportional to the temperature or at a rate that is proportional to the temperature and the time, and thus provide an indication of the full or partial time-temperature history of their immediate surroundings. Time temperature indicators (TTIs) are simple and inexpensive devices, typically designed as labels. When attached to a perishable good, a TTI (appropriately designed and calibrated) monitors its time-temperature history and provides a simple, usually visual, straightforward summary of the exposure history of the product to time-temperature, thereby providing indication of the product's freshness condition. Consequently, TTIs are among the most promising shelf-life-report technologies.

The TTI concept was developed to ensure the safety and quality of perishable goods, such as food and drug products, throughout their entire lifespan, from manufacturing to the time they are consumed by the end-user. The safety and quality of many perishable goods such as food, drugs, vaccines and blood, depend mainly on appropriate storage conditions during distribution and storage. Different factors such as gas composition, relative humidity and temperature affect their real lifetime. The fact that changing conditions affect the effective shelf-life of these kinds of goods is not reflected by a "best before . . . " type label that relies on appropriate storage conditions. Of all storage factors, temperature abuse is the most frequently observed factor for deterioration, based on diverse physical, chemical, enzymatic or microbial processes. Therefore, the TTI technology can provide a simple tool for controlling the food and drug supply-chain. The color and/or other visual physical properties of the TTI varies as a function of the time at a rate which is temperature dependent or time-temperature dependent, thus providing an active scale of "freshness" of the product to which it is attached, by comparing the color (or darkness) or any other varying visual property of the TTI label with a given comparative scale. Since the TTI indicators may be designed to provide a distinct "Yes" or "No" type of answer regarding the time temperature factor, they may provide an important "clear cut" answer and save further elaborate data inspection. This is ideal for HACCP (Hazard Analysis Critical Control Point), where the emphasis is on real time decision making and action.

Various TTIs are disclosed, for example in the following patent publications. U.S. Pat. No. 4,737,463 discloses a photoactivatable time-temperature indicator based on diacetylenic salts. A thermally unreactive ("inactive") diacetylenic salt (or a mixture of such salts) is mixed, in a polymeric matrix, with a material that generates acid upon exposure to light. Photoexcitation, preferably by UV or near UV light, causes the formation of a thermal reactive ("active") free diacetylenic acid. Following this activation step, a progressive color development occurs at a rate that increases with temperature. The indicator is useful for monitoring the freshness of perishable products, particularly those that require refrigeration.

WO 99/39197 discloses a technique, which provides a substrate for packaging time- and temperature-sensitive products or for application thereon. According to this technique, planar time-temperature integrator is used consisting of a matrix and at least one reversible indicator embedded therein being arranged in the area of the substrate. The indicator has photochromic properties.

U.S. Pat. No. 6,435,128 discloses a time-temperature integrating indicator device that provides a visually observable indication of the cumulative thermal exposure of an object. The device includes a substrate having a diffusely light-reflective porous matrix and a backing. The backing includes on its surface a viscoelastic indicator material for contacting the substrate and a barrier material for substantially inhibiting the lateral and longitudinal flow of viscoelastic indicator material between the substrate and the backing.

U.S. Pat. No. 6,042,264 discloses a time-temperature indicator device, designed as a label, for measuring the length of time to which a product has been exposed to a temperature above a pre-determined temperature. The period of time of exposure is integrated with the temperature to which the indicator is exposed. The label is a composite of a plurality of layers adapted to be adhered at its underside to a product container. The label includes a printable surface layer, a longitudinal wicking strip that is adhered underneath the surface layer substantially at the opposite extremities only of the wicking strip and a lower substrate layer forming an envelope with the surface layer. A heat-fusible substance, which melts and flows above a pre-determined temperature, is applied on the surface of the wicking strip contiguous to at least one of the ends of the wicking member. When the heat-fusible substance is exposed to a temperature above the pre-determined temperature, the heat-fusible substance flows along the length of the wicking member. The label has a printable surface layer and is sealed at its peripheral edge to the peripheral edge of the substrate layer. These layers encapsulate the wicking member and the heat-fusible substance. The surface layer is provided with a sight window at an intermediate location over the wicking member through which the progress of flow on the wicking member is observed.

PCT Publication Application No. WO 03/077227 discloses a time indicating label comprising a label substrate having first and second surfaces, an acid-based indicator composition, and an activator composition. One of the acid-based indicator composition and the activator composition is on the first surface of the substrate, and both of these compositions when brought in contact remain adhered. The label may have a pressure sensitive adhesive on the second surface of the label. The label provides an effective means for determining the safety of frozen foods. The labels also provide a means of providing security by providing name badges that are time sensitive and may not be reused. The name badges provide a means to monitor the length of a visitor's time and prevent reusing the name badge.

PCT Publication Application No. WO 03/044521 discloses a sensor adapted to be remotely readable by RF techniques for identification of the quality of a packaged foodstuff. The sensor either reacts with compounds generated in the atmosphere of the foodstuff package due to the microbiological decay of the foodstuff, for example hydrogen sulfide or other sulfide compounds, or the sensor is responsive to an increased oxygen content in the atmosphere of the package due to a leakage in the package. The sensor is based on a RF circuit. Oxygen or the microbiologically generated gas affects the electrical properties of the circuit material. For example, the resistor, the capacitor or the inductive coil of the circuit or at least a fraction thereof are made of silver, iron, aluminum, a redox-type indicator-dye, a conductive polymer, or copper. Due to the reaction of the aforementioned gases with these materials, the sensor resistance, conductivity, capacitance and/or inductance of the respective sensor elements changes depending on the amount of the disintegrating gas.

PCT Publication Application No. WO 01/25472 discloses a biosensor useful to monitor the time and temperature to which a product has been exposed. The biosensor is based on a RF circuit comprising a unit, which changes its conductivity/resistance as a function of time and temperature. This unit comprises an enzyme and a substrate, wherein the enzyme is adapted to affect the substrate so that its conductivity increases as a function of time and temperature. Thus, a biosensor is disclosed, whose RF circuit can be activated by applying, for instance, a magnetic field over the same to generate a measurable current, which is dependent on the total resistance of the circuit and which thus varies as a function of the time and temperature to which the unit of the biosensor has been exposed.

PCT Publication Application No. WO 95/33991 discloses a condition indicator for perishable goods. The indicator comprises sensor means for gas or vapor associated with decay or contamination affecting an electrical property of the sensor means, which are incorporated into an electrical circuit measuring the property. The electrical circuit disclosed in WO 95/33991 is not a RF circuit. That means the sensor changes are not remotely readable. The circuit may be printed. The sensor may comprise a semiconducting material such as polypyrroles, which change an electrical property such as resistance or impedance on exposure to certain gases.

SUMMARY OF THE INVENTION

The present invention, in some embodiments thereof, relates to temperature sensitive applied materials and devices as temperature indicators, whether as a threshold, a temperature history or a combination thereof, optionally with a visually and/or instrumentally visible summary of the elapsed time-temperature profile the device had experienced.

According to at least some embodiments, the devices may optionally be time and/or temperature sensitive devices. Regardless of their sensitivity, and hence the factor(s) which affect the devices, the devices may optionally be perceived as being affected by time, in the sense that a visual display on the devices evolves or changes over time, even if both time and temperature optionally affect such a visual display.

According to at least some embodiments, there is provided a promotional object, which is a time and/or temperature sensitive device having a display that features a coupon or other incentive to stimulate a purchase and/or a visit to a commercial location. Non-limiting examples of such a commercial location include a store, a restaurant, a movie theatre, a live performance location, a club and the like. The display may optionally feature the incentive in a single appearance after a set time or with a multi stage appearance, in which the display changes a plurality of times to feature the incentive(s).

According to at least some embodiments, there is provided a prize object, which is a time and/or temperature sensitive device having a display that features a prize that is won. The prize may optionally be a lottery prize or the like. Optionally, the prize is only indicated as being won on certain prize objects, while other objects may optionally feature a display indicating a consolation prize or no prize. The display may optionally feature the prize in a single appearance after a set time or with a multi stage appearance, in which the display changes a plurality of times to feature the prize(s).

According to at least some embodiments, there is provided an entertainment object, which is a time and/or temperature sensitive device having a display that features a story in parts or a greeting card that reveals some type of visual indication over time. Such a story and/or visual indication may be described as information. This information can be preprinted or variable; if the latter, optionally the information is controlled by the user.

According to at least some embodiments, optionally any of the above embodiments may be combined with a time limitation, such that after a certain amount of time has elapsed, the promotion, prize or entertainment display ceases to display the visual indication. For example, for an incentive such as a store coupon, the user would need to bring the coupon to the store while the visual indication was still being displayed, thereby incentivizing the user to go to the store more quickly.

According to at least some embodiments, optionally any of the technologies described below may be used to implement these devices, non-limiting examples of which are given in Examples 1-4 below, provided after technology Examples A-P.

In at least some embodiments, the devices may optionally be used for determining a temperature status of a temperature sensitive product, such as a perishable good for example. By "temperature status" it is meant a temperature experienced by the product to which it is thermally coupled and in equilibrium or pseudoequilibrium, whether as a breach of a minimum or maximum temperature threshold, a temperature history, a time temperature history or a combination thereof. By a "temperature history" it is meant cumulative exposure to temperature over any given period of time. By "time temperature history" it is meant the collective exposure to temperature and elapsed time, as a temperature sensitive product may be expected to suffer from the cumulative effects of both temperature and time.

The present invention, in some embodiments thereof, relates to a temperature indicator apparatus, system and method capable of reporting a summary of the elapsed time-temperature history of a good to which it is thermally coupled (a TTI). The TTI can provide a summary of the elapsed time-temperature above a pre-set temperature threshold (HTTI), below a pre-set temperature threshold (LTTI), or at all the temperature ranges (TTI).

According to other embodiments, the temperature indicator specifically provides an indication as to whether a temperature threshold at, around or below a set low temperature point has been breached, without providing a time and temperature history (hereinafter referred to as "freeze indicator", FI).

According to yet other embodiments, the temperature indicator specifically provides an indication as to whether a temperature threshold at, around or above a set high temperature point has been breached, optionally without providing a time and temperature history (hereinafter referred to as "threshold indicator", TI).

According to yet other embodiments, different indicators are attached to one another, providing both threshold and/or freeze indications optionally without providing a time-temperature history.

Also optionally, different embodiments of temperature sensitive devices as described herein (TTIs, TIs and/or FIs) may be combined in one label and/or one device, optionally including providing such a combination on one substrate, for example by printing on a single substrate.

According to yet other embodiments, different indicators provide one "YES"/"NO" indication that accounts for both threshold and freeze indications, optionally without providing a time-temperature history.

According to yet other embodiments, freeze (FI) and/or threshold (TI) indicators are attached to a TTI, providing a time-temperature history indication that is optionally accompanied by threshold and freeze indications. The latter indications would preferably have a reaction temperature that is outside of the range the TTI is effectively monitoring the freshness of the product to which it is attached.

The TTI device according to at least some embodiments of the present invention is configured so as to provide a change in the properties of the TTI structure, induced by a time-temperature dependent chemical process in the TTI structure. Such changes in the properties of a TTI structure may include optical properties and/or electrical properties.

In one embodiment of the invention the TTI comprises two types of reactants and the process commences when these two types of reactants are contacted with one another. The first type of reactants (also referred to as the "passive reactant") comprise of a reactant that upon contacting with second type of reactants interacts and/or reacts with at least one of them. The second type of reactants (also referred to as the "active reactant") comprise of at least one metallic layer, optionally being at least a part of an electrical component, in which the at least one metallic layer is selected such it changes at least an electrical property, optionally of the electrical component, at a rate that is temperature dependent or at a rate that time-temperature dependent upon coming in contact with the passive reactant.

In some embodiments the at least one metallic layer changes at least one optical property at a rate that is temperature dependent or at a rate that time-temperature dependent upon coming in contact with the passive reactant. In other embodiments the at least one metallic layer changes at least an electrical property and changes at least one optical property at a rate that time-temperature dependent upon coming in contact with the passive reactant. The change in electrical properties and optical properties may be correlated or non-correlated.

This change in at least an electrical property is detectable as a change in one or more electrical properties of the TTI structure, such as its interaction with electromagnetic radiation (emission, reflection, absorption etc.) and/or its interaction with electrons (resistance, conductance, capacitance etc.). The change in at least an electrical property may be transmitted to the spectator relying on internal energy resources such as batteries, in the case it is configured as a so-called "active TTI structure", or by relying on interaction of the TTI with external electromagnetic and/or any other source of stimulus in the case of a so-called "passive TTI structure". This component of the TTI structure (passive or active) is initially an electrically conductive component and changes its conductivity as a function of the temperature and the time after coming in contact with the "passive reactant".

The change in properties of the TTI structure may also be visually detectable, as a change in the interaction of the TTI with light, such as color, reflectivity, etc.). In this type of embodiments the visual properties of the TTI change as a function of the time and the temperature. In some embodiments, the TTI may change its optical and electrical properties.

As a non-limiting example of changed optical properties, such changed optical properties may occur when the chemical reaction is selected from the group consisting of acid-base reaction, oxidation-reduction reaction and salt forming reaction.

In yet other embodiments, the "passive reactant" is in the form of inactivated reactant residing dormant on the surface of the "active reactant". Upon activation of the inactivated and dormant "passive reactant" is activated and the time-temperature process starts.

The term "active reactant", as compared to a "passive reactant", signifies a reactant forming, undergoing or being a part of the TTI component of a changeable electrical and/or optical property.

The technology of the present invention relies on a reaction, which preferably takes place between at least two reactants, of which one is a "passive reactant" and one is an "active reactant".

As indicated above, the reaction (process) may involve or be mediated, catalyzed, inhibited and/or induced by additional one or more substances (passive reactant(s)).

Optionally, such additional substances may comprise one or more substances affecting diffusion, such as viscous materials. For example, the passive reactant(s) may for example include a viscous substance (termed here "viscous component") that contains and/or mediates diffusion of the passive and/or active reactants to one another at a rate that is correlated to the time or at a rate that is correlated to the time and the temperature.

Alternatively, a viscous substance may be present within or as part of the active reactant of the TTI structure, as for example in the case of a TTI that is in the form of a capacitor as an electrical component: the capacitor is composed of two electrodes separated by a porous and insulating medium acting as a spacer. A viscous substance fills the vacancies of the porous medium that is located in between the capacitor plates, and the degree of penetration of this viscous liquid, being a function of the elapsed time-temperature, changes the capacitance. Similarly, the active component may be composed of several capacitors, the time-temperature history being expressed in the number of capacitors that have been penetrated and thus "destroyed" by the viscous liquid. In case at least one electrode of the capacitor transmits visible light and the viscous substrate liquid is colored one can use this TTI structure as a visual TTI.

The viscous medium may be a normal viscous medium having its viscosity inversely proportional to the temperature (i.e. viscosity increasing with decreasing temperature) or an abnormal viscous medium having its viscosity proportional to the temperature (i.e. viscosity increasing with increasing temperature); see for example R. ANGELINI, G. RUOCCO, Philosophical Magazine, 87, 553-558, 2007 and van Hooy-Corstjens C. S. J., Hohne G. W. H., Rastogi S., Macromolecules, 38, 1814-1821, 2005.

According to other embodiments of the invention, the device comprises at least two reactants located adjacent to each other (e.g., in contact with one another), wherein these at least two reactants are selected such that when at least one passive reactant from the at least two reactants undergoes a phase change, it affects the chemical reaction with at least one active reactant from the at least two reactants, the reaction effecting a change in an electrical and/or optical property of a component with which the at least one active reactant is associated.

It should be understood that the term "undergoes a phase change" used herein signifies local, partial or complete sublimation, or melting, or dissolution, or material penetration, or any of first, second and mixed order phase transitions, such as glass transition, melting, inverse freezing, inverse melting etc.

If a TTI undergoes a phase transition, as described above then according to at least some embodiments, the TTI is a partial history time-temperature indicator, as the TTI only reacts or records time spent at temperatures above (HTTI) and/or below (LTTI) a set threshold. In the case of upper threshold temperature indicators (HTTIs), the embodiment may include a viscous passive reactant solution that freezes below a set temperature (viscosity increases significantly, and sometimes abruptly, upon lowering the temperature such that below a set temperature its process is practically stopped).

In yet other embodiments for lower threshold temperature indicators (LTTIs), the embodiment may include a viscous passive reactant solution that practically freezes above a set temperature (viscosity increases significantly, and sometimes abruptly, upon elevating the temperature such that above a set temperature its process is practically stopped). The later embodiment may rely, on a phenomenon termed "inverse freezing" and "inverse melting".

As indicated above, the device may include a viscous component as a second "passive reactant", which may be at the outer surface of the device; or may be present in or with the "active reactant". The viscous component may or may not have a solid-to-liquid transition at temperatures that are relevant to the specific application and consequently monitor partial or full time-temperature history. The viscous component is characterized by that when upon exposure to temperatures higher/lower (for normal and inverse freezing systems respectively) than a certain threshold temperature specific for the viscous component, it undergoes a change in its mobility and/or viscosity and/or ability to dissolve and transport other chemical substances as well as propagate, for example in porous solids, such as, but not limited to, for example glass powder packed in a tube. This certain temperature (which may for example optionally comprise a freezing point) may be selected to be within a temperature range relevant for a specific application of a TTI device and thus the use of this viscous component provides for partial time-temperature history indication: below/above (for normal and inverse freezing systems respectively) this temperature, there is no measurement of time-temperature changes, e.g., since the viscous component is a solid and has no (or very low) time-temperature dependence of mobility until reaching the temperature. Alternatively, the viscous component may be selected with such a threshold temperature well outside the relevant temperature range thus providing for full time-temperature history measurements.

The TTIs and/or TI and/or FI device is preferably appropriately designed to prevent the chemical reaction from occurring unnecessarily when the device is inoperative, and allow the development of this process/reaction when the device is put in operation. This may be achieved by initially placing the entire TTI and/or TI and/or FI structure in a sealed enclosure, which is configured to allow breaking, removing or puncturing thereof to thereby expose the TTI and/or TI structure to the environmental changes. Another option is to use an adhesive-type viscous polymer or placing a viscous polymer on a label, thus attaching the viscous component to the other part of the TTI (active reactant, or active and passive reactants) and/or TI and/or FI, which is inactive without the viscous component.

Yet another option is to place a passive reactant (e.g., viscous component) in a sealed reservoir, so that it is separate from the active reactant, and when the TTI and/or TI and/or FI device is to be put in operation, removing the sealed enclosure and attaching the reservoir to the other part of the TTI (active reactant, or active reactant and a second passive reactant) and/or TI and/or FI to thereby allow penetration of the passive reactant (e.g., viscous component) from the reservoir to the other part of the TTI and/or TI and/or FI.

In yet another embodiment, the TTI device, while being inoperative, is kept at a temperature in which the TTI structure (i.e., passive reactant(s) and/or possibly also active reactant(s)) is either inactive or substantially inactive; and to put the device in operation, it is exposed to the relevant temperature range. In all the abovementioned options, the viscous component may serve by itself to induce the time and temperature changes in the active reactant or may include yet at least another one passive reactant that induces the time and temperature changes in the active reactant.

The active reactant may optionally be an electrically conductive material within an electric circuit. The electrically conductive material may be patterned to form the features of a component that can be part of a RF tag (antenna, resistor, capacitor etc.). The chemical reaction thus causes time and temperature dependent changes in the circuit of the tag. The RF circuit pattern may be produced by any known suitable technique, e.g., printing (e.g., ink jet printing), CVD, PVD, sputtering, patterning (e.g., molding and cutting/etching), electro-deposition, electroless deposition etc. The device may be configured as a multi-layer structure (hybrid structure), including a first substrate layer of an electrically insulting (and possibly optically transparent) material, carrying a second layer structure of a component formed by the active reactant (electrically conductive layer; or a layer structure patterned to form a capacitor or a resistor etc.), and possibly also a third layer of passive reactant material. The device may also include an uppermost layer of an optically transparent and electrically insulating material.

According to at least some embodiments, time-temperature indicator (TTI) and/or threshold temperature (threshold (TI) and/or freeze (FI)) devices are characterized in that the electrical component is selected from the group consisting of conductor resistor, capacitor, diode, inductance coil and antenna. It is especially preferred that the electrical component is configured as at least one element of an RF circuit or as at least one component that can electrically interact with an RF circuit.

The electrical embodiment may optionally be combined with the viscous substance as follows. Considering a capacitor component formed by two metal/conductive layers that are separated by a porous medium having a certain dielectric constant, a viscous component may be used as a passive reactant to penetrate the porous component at a rate that is temperature dependent or at a rate that is time-temperature dependent and thereby cause either a sudden or increasing short (change in resistance between these two metal/conductive layers) in the capacitor or a gradual change in the capacitance due to the difference in the dielectric constants of the pure porous medium and the porous medium filled with the viscous component.

According to at least some embodiments, a barrier is provided between the active and passive reactants, the barrier layer may serve as a diffusion layer for the passive reactant, thereby providing yet another type of time-temperature process for the TTI device, according to which the measured time-temperature history is determined. In order for the passive reactant layer to become in contact with the active reactant layer, the first time-temperature dependent process involves propagation of the passive reactant through the barrier, followed by the reaction and/or interaction between the passive reactant and active reactant.

In yet other embodiments of the invention the TTI comprises at least two types of reactants, including at least one "passive reactant" (a reactant that upon contacting with second type of reactants (active reactants) interacts and/or reacts with at least one of them, changing at least an optical and/or an electrical property of the TTI), and at least one "active reactant" in the form of a metallic layer, selected such it changes at least an electrical property or an optical property at a rate that is temperature dependent or at a rate that time-temperature dependent upon coming in contact with the passive reactant.

Optionally, such a metallic layer is covered with a barrier or barrier layer. Without wishing to be limited by a single hypothesis, addition of the barrier layer yields two effects, one being the retardation of the commencement of the interaction and/or reaction between the "active reactant" and "passive reactant", rendering the rate of the reaction of the TTI time-temperature dependent, while the other is expressed in the alteration of the rate and its temperature dependence of reaction and/or interaction between the "active reactant" and "passive reactant". The magnitude of the retardation as well as rate and temperature sensitivity alteration of the process depends on the nature of the barrier layer. Barrier layers are normally made of polymers and are therefore easily printable on the surface of the at least one "active reactant" in the form of a metallic layer. Alternatively, such barrier layers may be formed during production of the TTI, for example using flexography printing of a mixture of monomers thereof and polymerizing them using, UV, EB and the like.

Again without wishing to be limited by a single hypothesis, optionally bathers are constructed such that the reaction of the passive and active reactants does not provide a simple exponential decay but rather results in a hysteresis, followed by a first exponent decay. In other cases, the barriers are constructed to exhibit a rather short hysteresis and a non-first order decay. The specific nature of the time and temperature dependence of the TTI operation depends on the nature of the bather.

The addition of a barrier layer optionally permits visualization of the time-temperature count using a plurality of TTI segments each having a different thickness and/or composition. In such TTIs, the segments will change optical and/or electrical properties one after the other, providing a clear presentation of both passed time-temperature as well as remaining time-temperature and/or time at any given temperature.

According to various embodiments, activation energy (and/or the temperature sensitivity of the process) and hence lifespan of the TTI (ie—the time period during which temperature history is recorded) may optionally be controlled according to the amount and type of reactants, and also according to the selected barrier.

Optionally and preferably, the barriers may be printed as for any other layer, as described herein in more detail. Optionally, such printing enables a multi-step TTI to be prepared from such printed layers.

According to various embodiments of the TTI with a barrier, the threshold indicator may optionally comprise colored crystals, and/or colorless crystals and colored powder dissolved and/or mixed in it and/or colorless crystals of acid/base and acid/base indicators.

Another embodiment of the present invention relates to a printing ink or printing ink concentrate, comprising the at least one active reactant, the at least one first passive reactant and/or the at least one second passive reactant of the above-described time-temperature indicator devices.

Yet another embodiment of the present invention relates to a packaging material or a label, comprising at least one of the above-described time-temperature indicator devices.

As used herein, the term "viscous" may also optionally relate to viscoelastic or Newtonian liquids.

As used herein the terms "good" and "product" are used interchangeably to refer to a physical item or object, or collection of physical items or objects.

In some embodiments, the TTI is in a form selected from the group consisting of a surface coating, a flexible film, a patch, a label, a pouch, a sachet, a liquid, an adhesive and an ink component.

In some embodiments, the product to which the TTI is coupled is selected from the group consisting of an edible product, a pharmaceutical product, a nutraceutical product, a cosmetic product and a cosmeceutical product.

According to at least some embodiments, there is provided a time temperature indicator (TTI) which is capable of providing a summary of the time and temperature history, comprising an active reactant layer, a passive reactant layer and a release layer, wherein the release layer separates the active reactant layer from the passive reactant layer, and wherein physical removal of the release layer enables the active reactant layer to contact the passive reactant layer and to start indicating the summary of time and temperature history.

Optionally the active reactant layer comprises a metallic layer and wherein the passive reactant layer comprises an etchant for etching the metallic layer.

Optionally the metallic layer comprises aluminum and the etchant comprises a pressure sensitive adhesive comprising a polyacrylic polymer, an aluminum etching acid, an anti-foaming agent and flattening agent.

Optionally the TTI further comprises a backing layer, the backing layer comprising an adhesive.

Optionally the TTI further comprises a front layer, comprising a visual indicator.

Optionally the summary of time and temperature history is indicated through an optical indication appearing upon etching of the metallic layer by the etchant.

Optionally the front layer further comprises a visual indicator that does not change with time and/or temperature, the TTI further comprising an impervious barrier under the visual indicator.

Optionally the impervious barrier is impervious to a reaction between the etchant and the metallic layer and comprises UV curable ink.

Optionally the summary of time and temperature history is indicated through an electrical indication appearing upon etching of the metallic layer by the etchant.

Optionally the TTI further comprises a viscous substance acting as a barrier to reaction between the passive and active reactants.

Optionally the passive reactant comprises a viscous substance.

Optionally the TTI further comprises a water resistant coating.

Optionally the water resistant coating comprises PVDC, silicon oxide, aluminum oxide, other oxides, polychlorotrifluoroethylene (PCTFE), polyvinyl fluoride and alike Optionally the TTI is adapted to provide a summary of the elapsed time-temperature above a pre-set temperature threshold (HTTI), below a pre-set temperature threshold (LTTI), or at all the temperature ranges (TTI).

Optionally the TTI further comprises an additional material that provides an indication that a temperature threshold at, around or below a set low temperature point has been breached, wherein the additional material does not provide information regarding a time and temperature history.

Optionally the TTI further comprises an opal structure.

Optionally the TTI further comprises an inverse opal structure.

Optionally the TTI further comprises an inverse melting material.

Optionally the TTI further comprises an additional material that provides an indication that a temperature threshold at, around or above a set high temperature point has been breached, wherein the additional material does not provide information regarding a time and temperature history.

Optionally the at least one material comprises lauric acid.

Optionally the at least one material comprises a combination of 4'-Amino-N-methylacetanilide and phenol red.

Optionally the indication comprises a change in electrical and/or optical properties of the at least one material.

Optionally the TTI further comprises a perishable good for being attached to the TTI.

Optionally the TTI further comprises a temperature history indicator, attached to the TTI.

According to at least some embodiments there is provided a threshold freeze indicator, comprising an inverse viscosity freeze material capable of providing an indication as to whether a minimum temperature threshold has been breached or provide indication to the elapsed that occurred upon exposure to a set temperature.

Optionally the indicator material comprises an inverse melting or an inverse freezing material.

Optionally the indicator further comprises two conductive layers separated by a porous layer, wherein the freeze indicator material passes through the porous layer at a rate that is inversely temperature dependent, advancing more quickly at lower temperatures.

Optionally the freeze indicator material is solid or undergoes non-linear increase of viscosity above a certain temperature or above a certain temperature range.

According to at least some embodiments there is provided a threshold freeze indicator (FI), comprising a photonic crystal construction capable of providing an indication as to whether a minimum temperature threshold has been breached.

Optionally the FI further comprises an opal structure.

Optionally the opal structure comprises ordered nanospheres immersed in water.

Optionally the FI further comprises an inverse opal structure.

Optionally the inverse opal structure comprises ordered nanocontainers containing water, produced from ordered nanospheres.

Optionally the nanospheres comprise polymer beads or inorganic oxide matrix.

Optionally the FI further comprises heavy water or water/heavy water mixtures.

Optionally the FI further comprises adding salt and/or an organic solvent to control the temperature of the minimum temperature threshold.

According to at least some embodiments there is provided an inverse TTI (time temperature indicator) for providing a time temperature history, comprising a porous medium, an inverse melting material, a destroyable seal and an inspection window; wherein the porous medium is separated from the inverse melting material by the destroyable seal, and wherein upon destruction of the destroyable seal, the inverse melting material enters the porous medium and provides an optical indication of the time temperature history.

Optionally the optical indication comprises a visual indication.

Optionally the inverse melting material comprises alpha-cyclodextrin (alpha-CD), water and 4-methylpyridine (4MP).

Optionally the inverse TTI further comprises a visible dye for providing the visual indication.

As used herein the term "about" refers to ±10%.

The terms "comprises", "comprising", "includes", "including", "having" and their conjugates mean "including but not limited to". The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a biomolecule" or "at least one biomolecule" may include a plurality of biomolecules, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced. For the avoidance of doubt, it is understood that the drawings are not necessarily shown to scale.

In the drawings:

FIG. 1A-3 shows an exemplary TTI that features both a threshold indicator (TI) and a time-temperature history indicator (TTI);

FIG. 1C shows a different implementation of the metal based TTI of FIG. 1A-1 according to at least some embodiments of the present invention, having the passive and active layers attached to one another in the unactivated form of the TTI, allowing its activation by pulling release layer and combining the layers;

FIGS. 2A-1, 2A-2, 2B-1 and 2B-2 show schematic illustrations of only the threshold indicator component alone (before and after crossing the pre-set threshold temperature) according to various embodiments of the present invention;

FIG. 3 shows the kinetics of a TTI made of aluminum (OD=0.6) on PET film at 4 C as a function of the water content in the passive reactant;

FIG. 4 depicts the color of an active spot of an aluminum (OD=0.6) based TTI having no barrier as a function of the time after activation, while FIG. 5 graphs the color changes as a function of the time after activation of a label that was stored at a constant temperature of 4 C.

Figure 11:
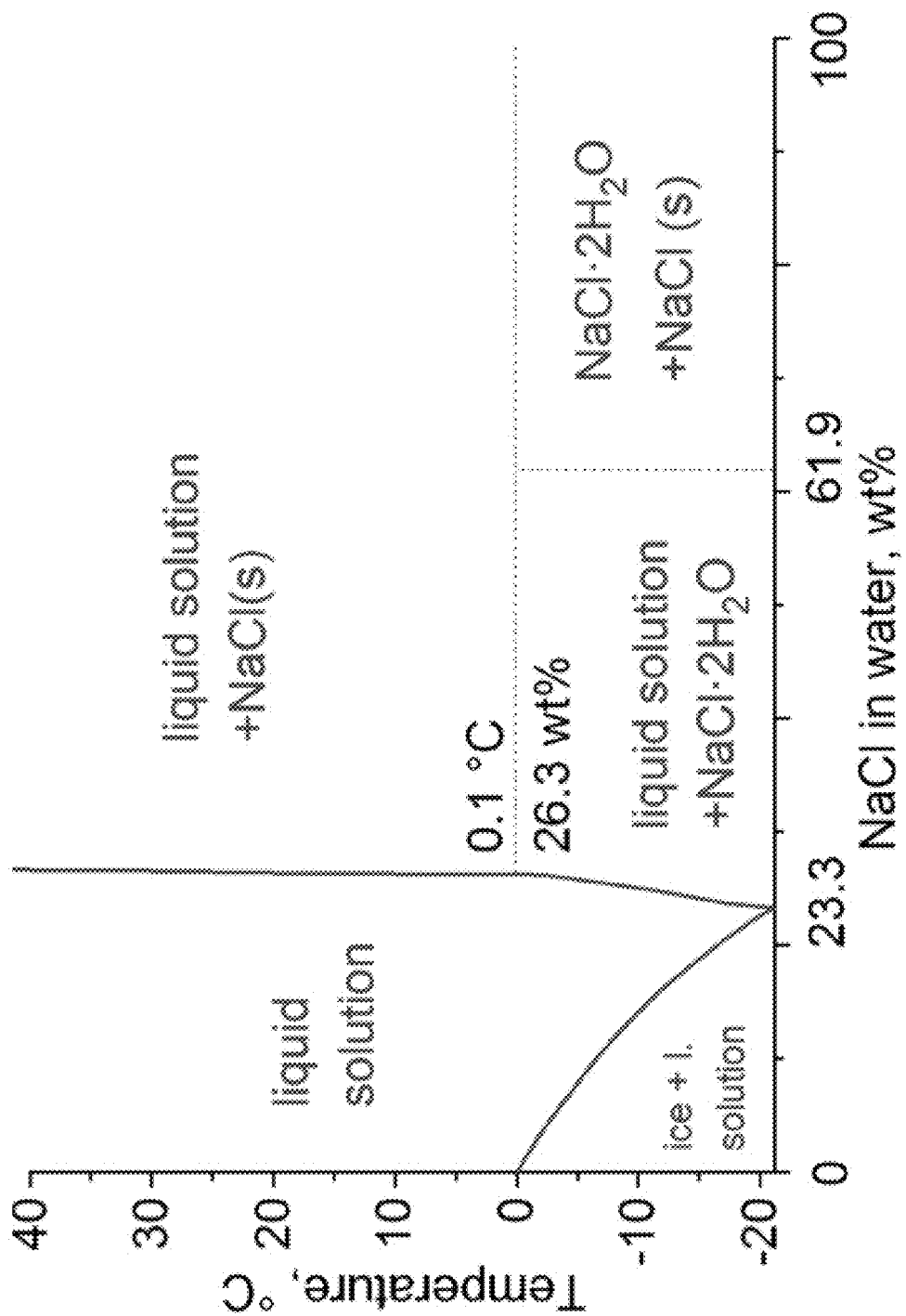
Figure 12:
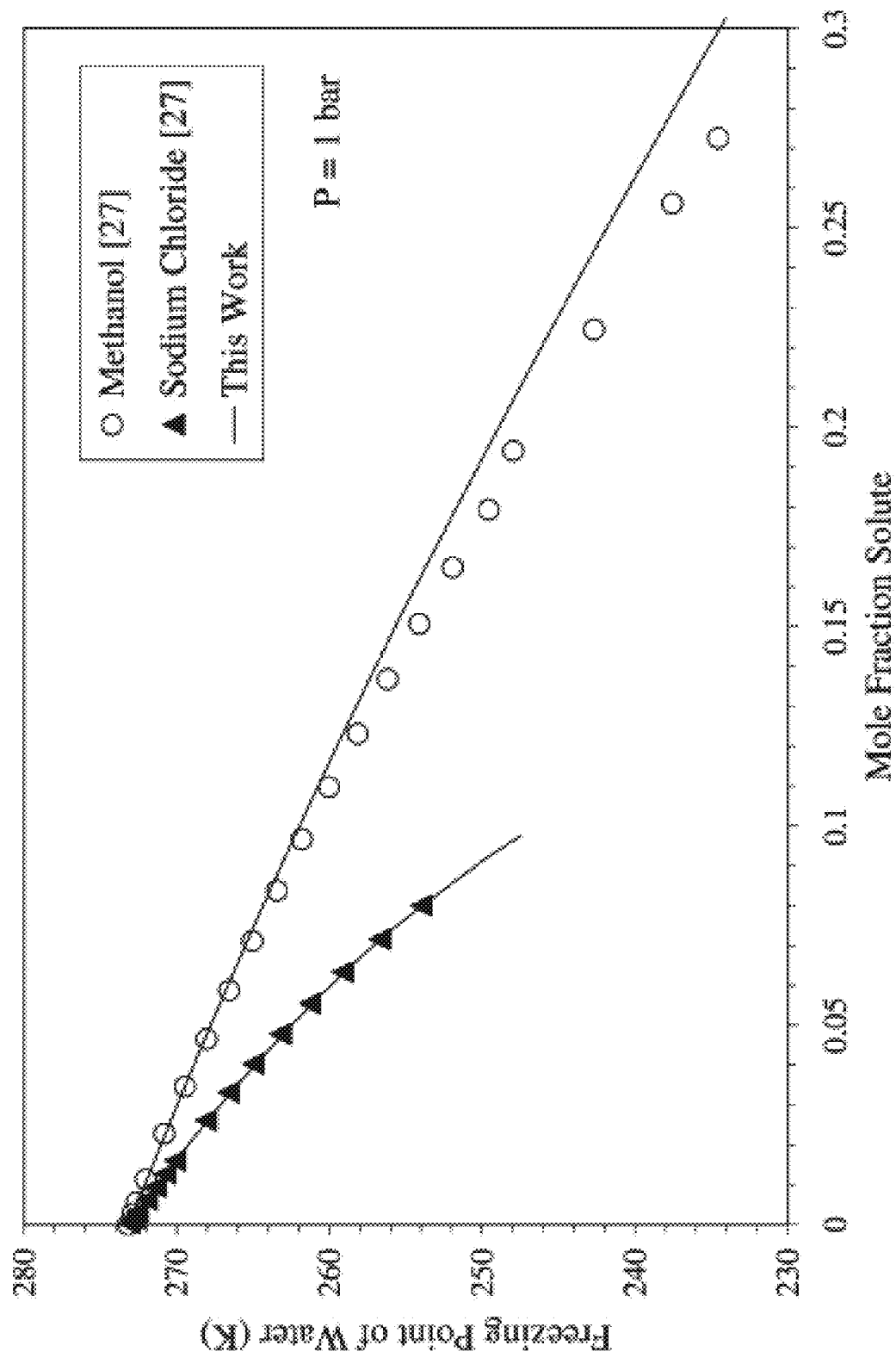

The results of mixing various salts with water are shown in FIG. 11, while the results of mixing the organic solvent methanol or the salt sodium chloride with water are shown in FIG. 12.

Figure 13:
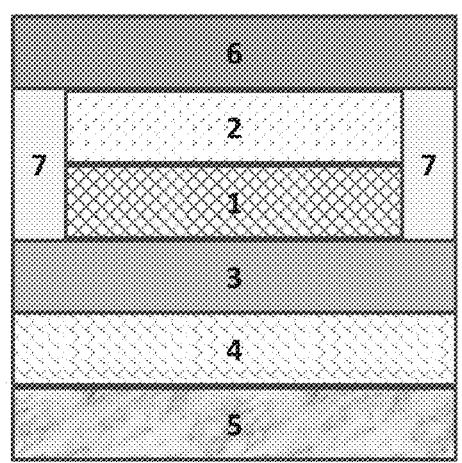
Figure 15:
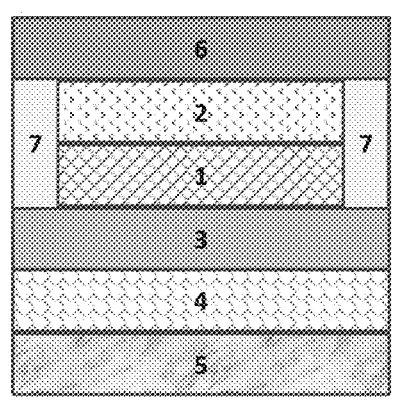
Figure 16:
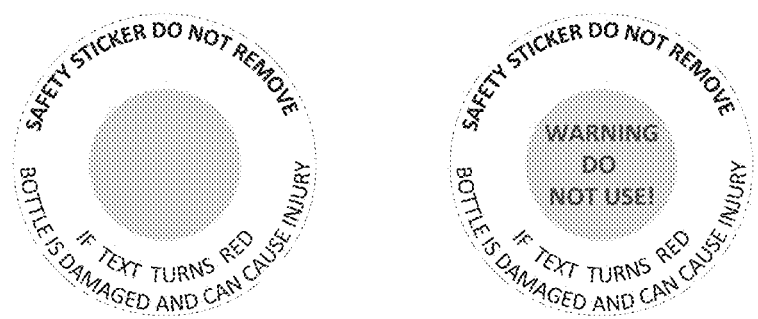
Figure 17:
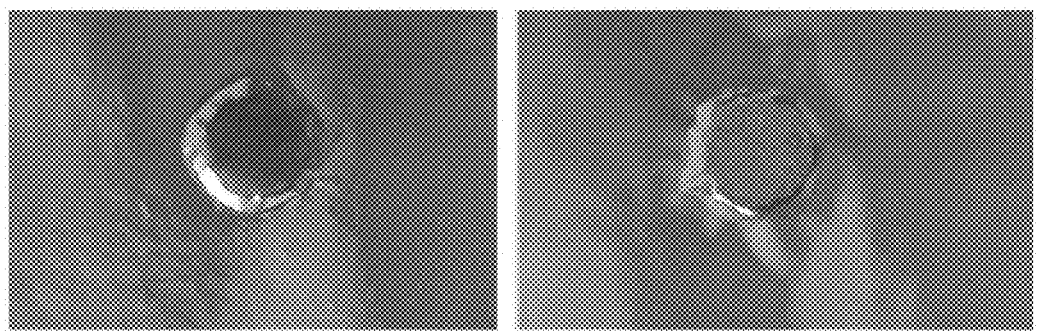
Figure 18A:
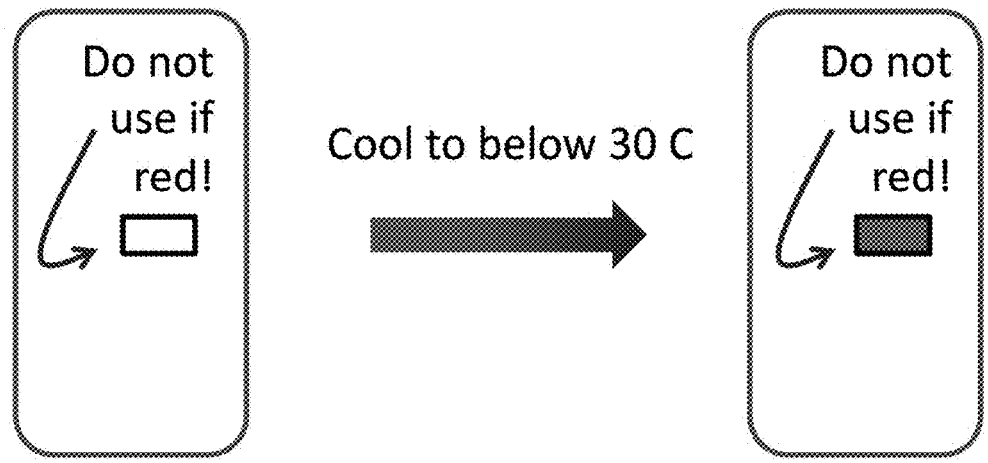
Figure 18B:
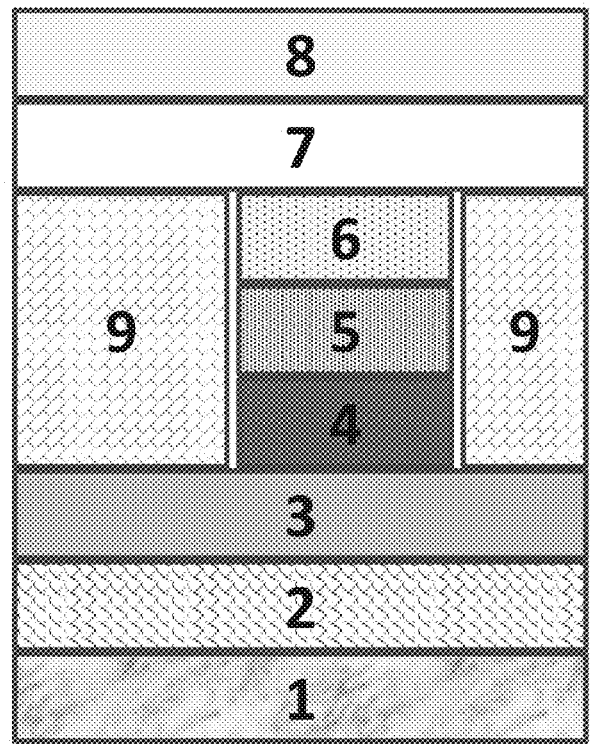
Figure 19A:
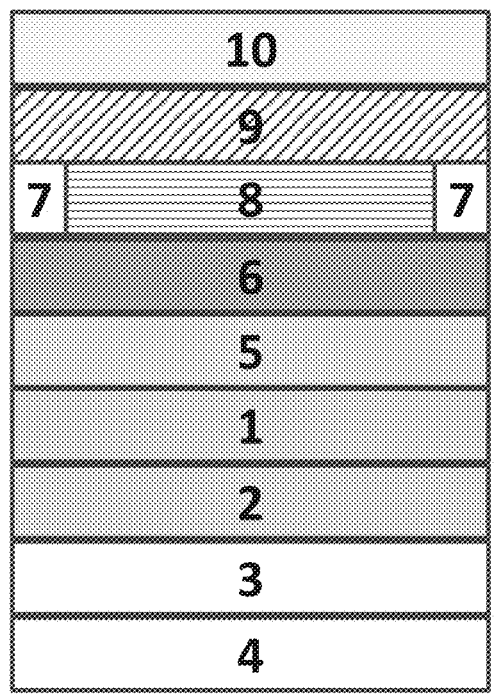
Figure 19B:
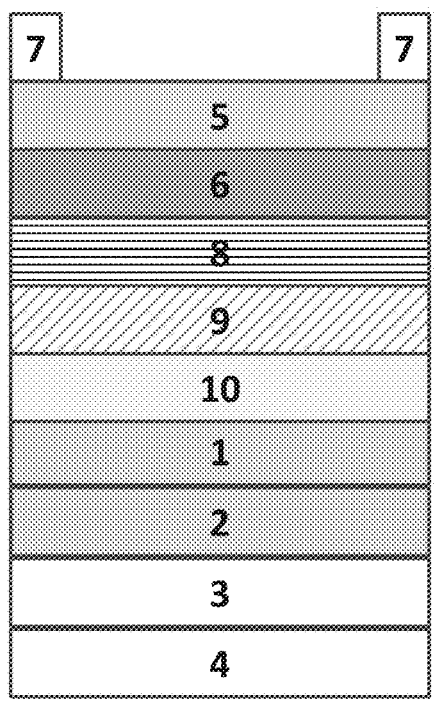
Figure 20:
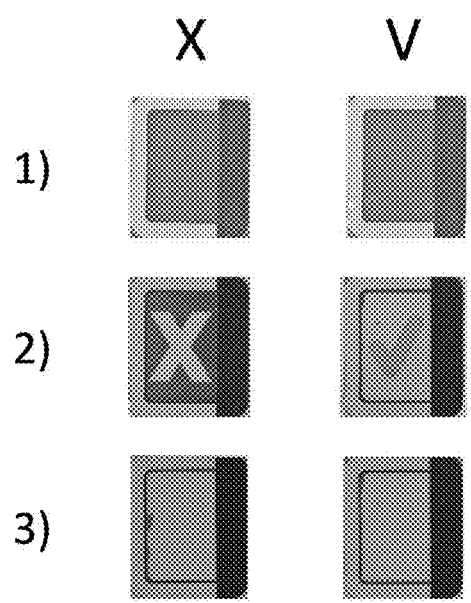

FIG. 13 shows an exemplary, illustrative, non-limiting threshold indicator based upon diffusion;

FIG. 14 shows an exemplary label having the layer structure of FIG. 13 before (left) and after (right) activation (i.e. before and after crossing the threshold temperature);

FIG. 15 shows an exemplary, non-limiting illustrative threshold indicator based upon metal etching;

FIG. 16 shows the threshold indicator of FIG. 15 in a schematic diagram of an exemplary label;

FIG. 17 shows a TI label having the layer structure of FIG. 16 before and after activation;

FIG. 18A shows an exemplary inverse freeze indicator (FI) label while FIG. 18B shows this exemplary label in a schematic cross sectional diagram;

FIG. 19A depicts a cross section of a non-limiting, exemplary, illustrative TTI label according to the embodiment in which the TTI provides a summary of the elapsed time-temperature, optionally in the form of a disappearing signal;

FIG. 19B depicts an alternative TTI structure of the embodiment of FIG. 19 where the top layer is the aluminized polymer film;

FIG. 20 depicts a non-limiting, exemplary, illustrative TTI with a disappearing signal according to at least some embodiments.

Figure 21:
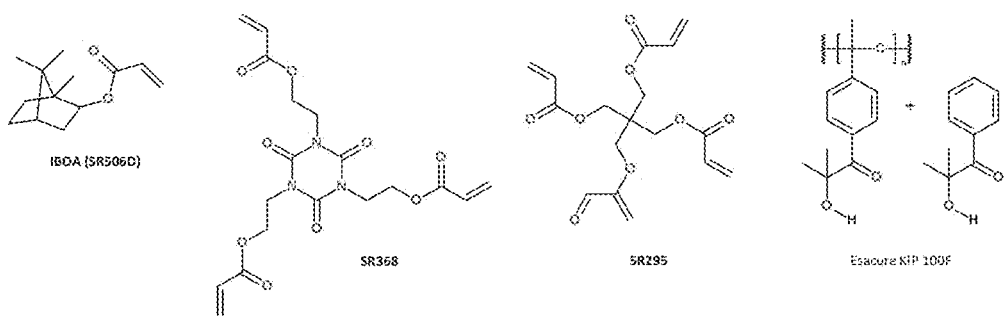

FIG. 21 shows molecules which may optionally be used for the production (for example, by flexography printing and UV curing) of a non-limiting, exemplary, illustrative impervious barrier for a TTI.

Figure 23:
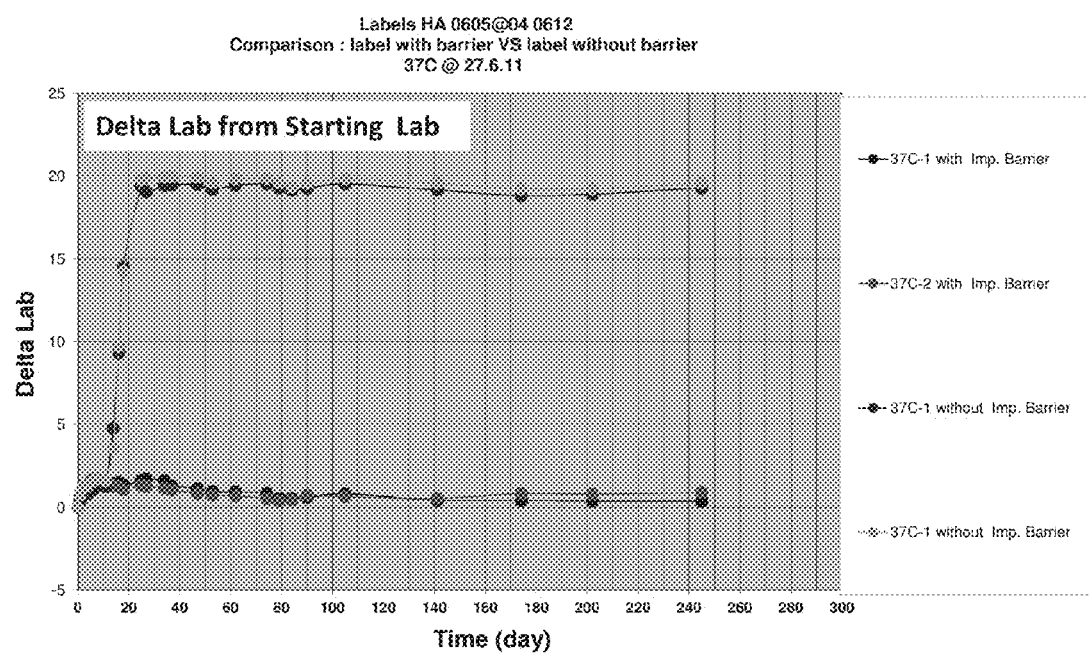
Figure 24:
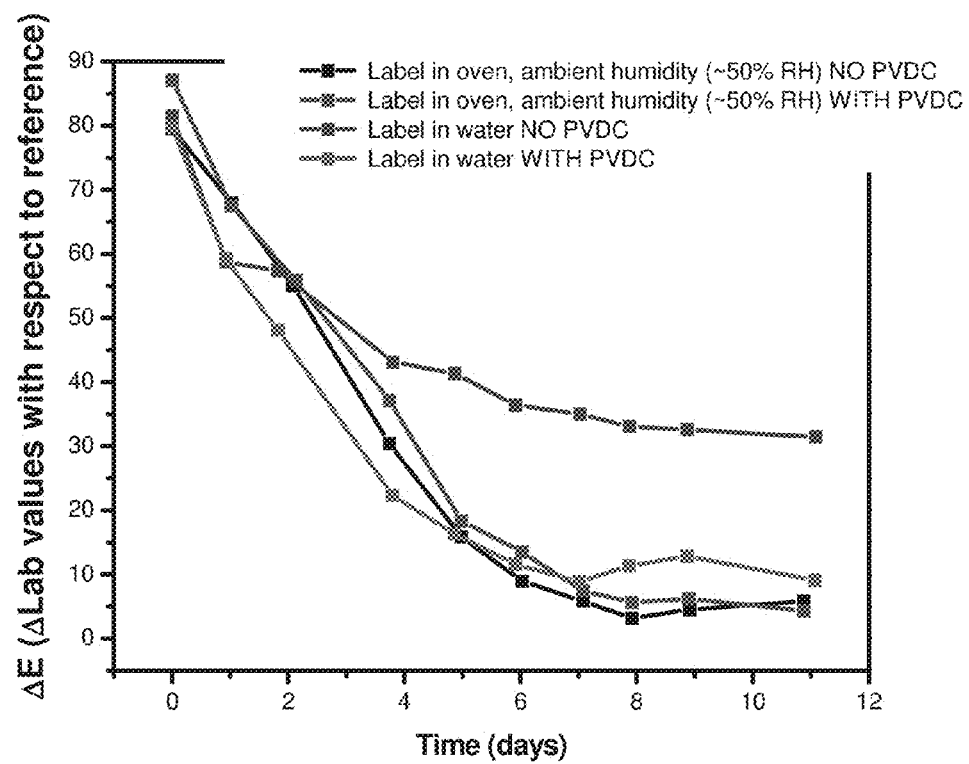
Figure 26:
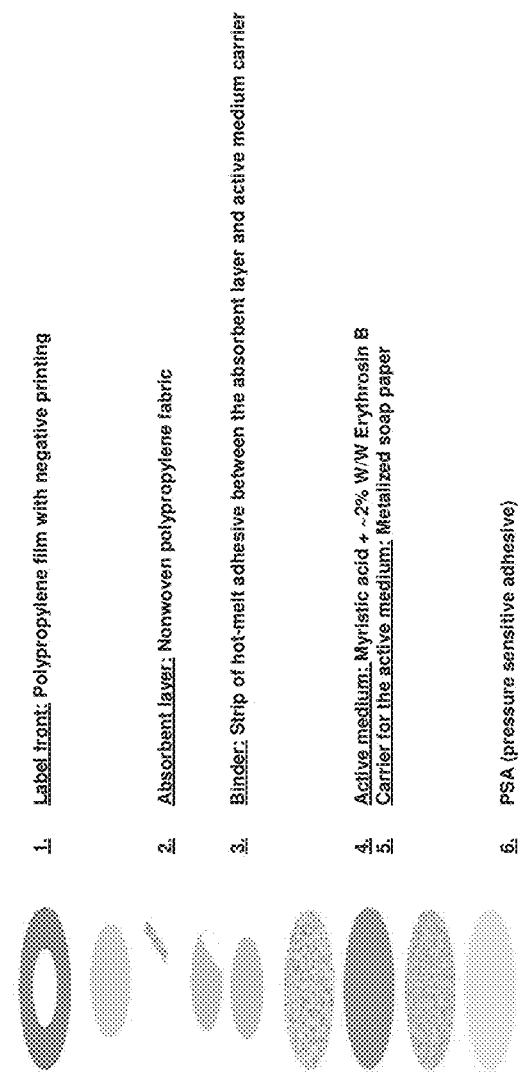
Figure 27:
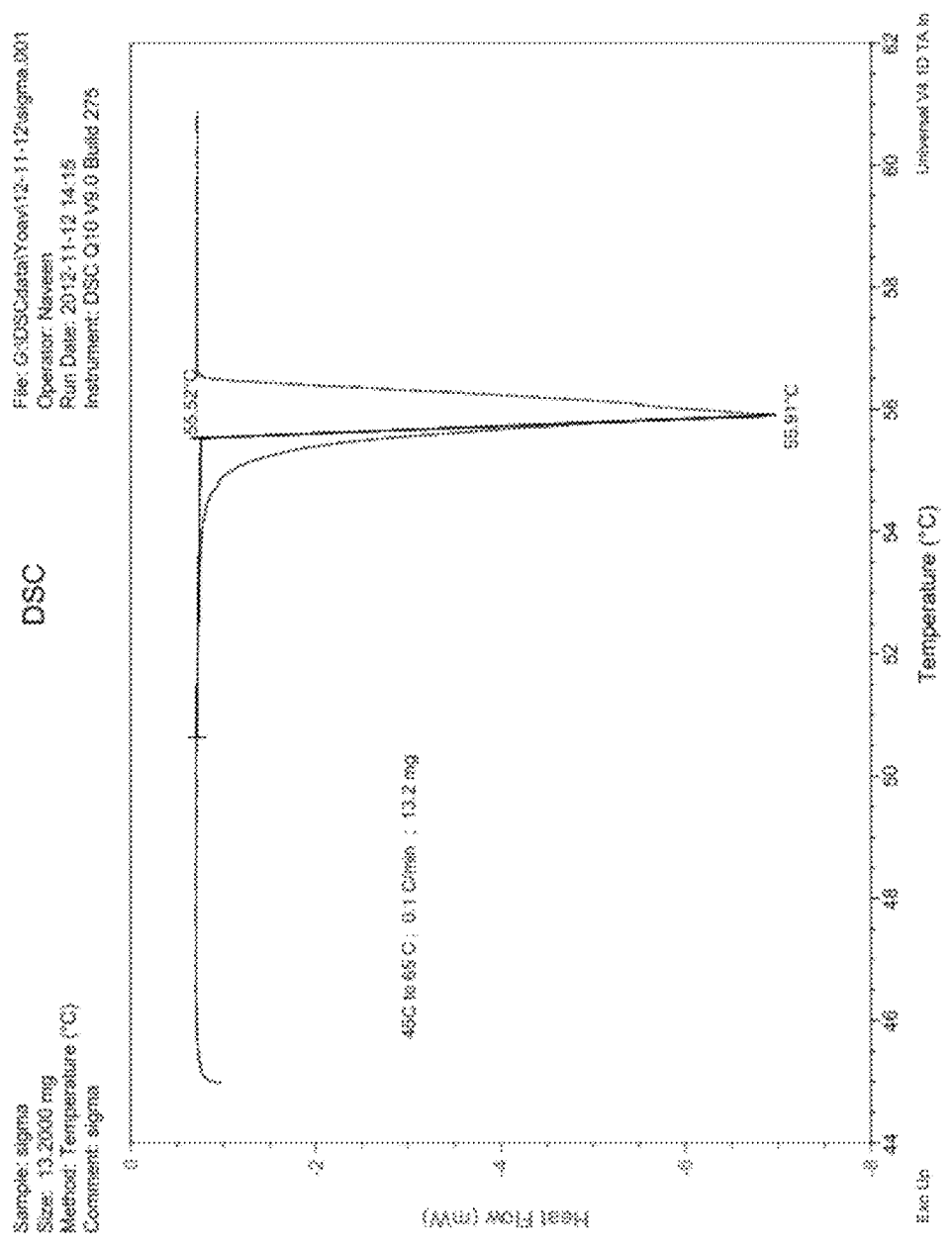

FIG. 22 depicts labels with and without the impervious barrier at different temperatures;

FIG. 23 depicts the CIE-Lab color values of the non-functional yellow part of TTI labels as a function of the time after activation with and without impervious barrier printed under the non-functional areas of the labels;

FIG. 24 depicts the kinetics of two TTI labels immersed in water at 4 C, of which one contains a top PVDC coating while the other does not;

FIG. 25 shows results for different compositions forming the active material of non-limiting embodiments of freeze indicator;

FIG. 26 shows an exemplary Threshold-60 VI Label;

FIG. 27 shows a differential scanning calorimetry graph of Myristic acid.

Figure 28A:
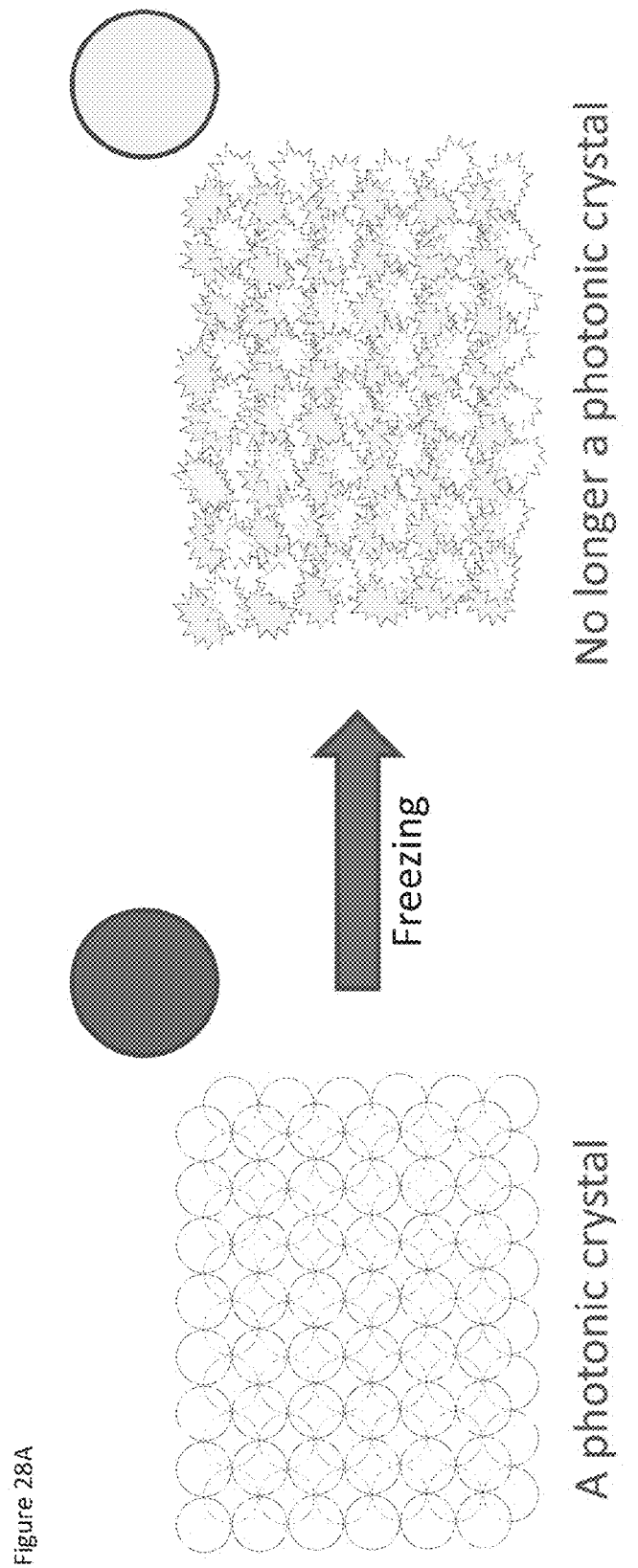
Figure 28C:
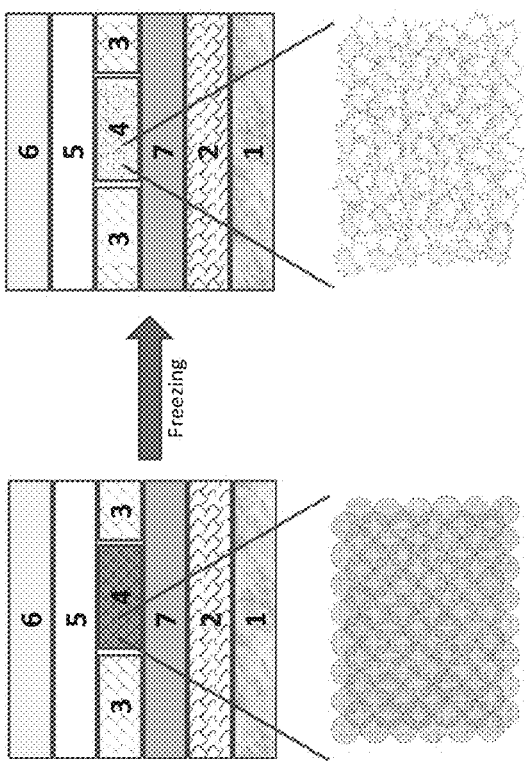
Figure 28B:
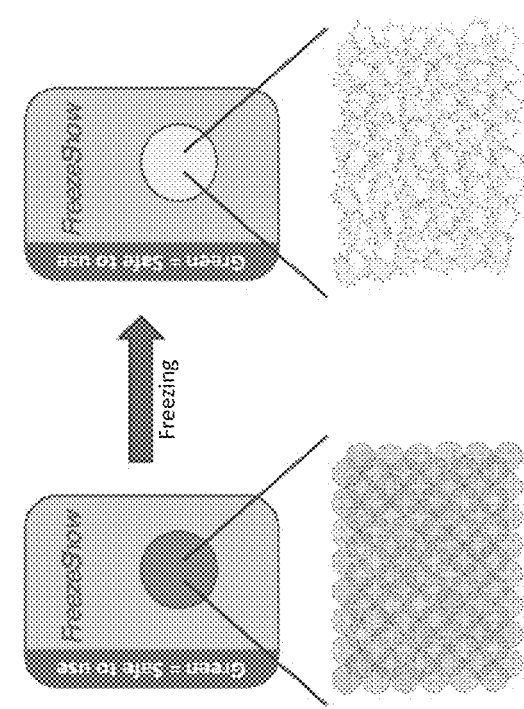

FIG. 28A shows an inverse opal photonic crystal containing an aqueous solution; FIG. 28B shows an exemplary FI based upon this technology.

Figure 29:
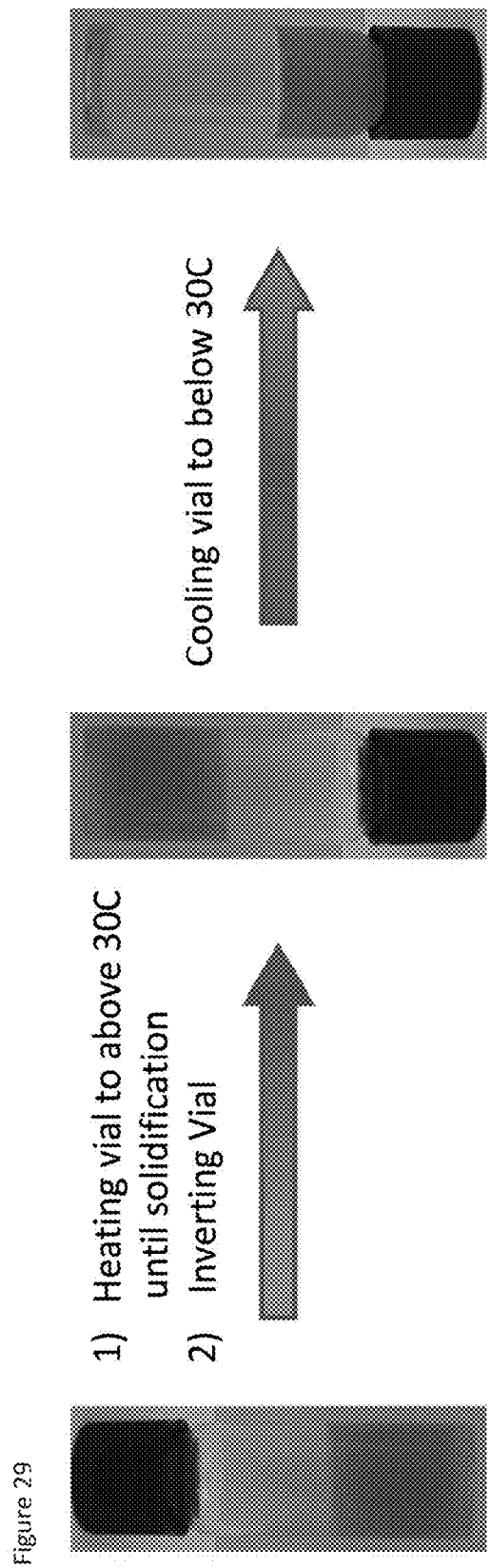

FIG. 29 shows an exemplary technology for a FI based upon inverse melting.

FIGS. 30A1, 30A2 and 30B show exemplary inverse TTIs based upon diffusion.

Figure 32A:
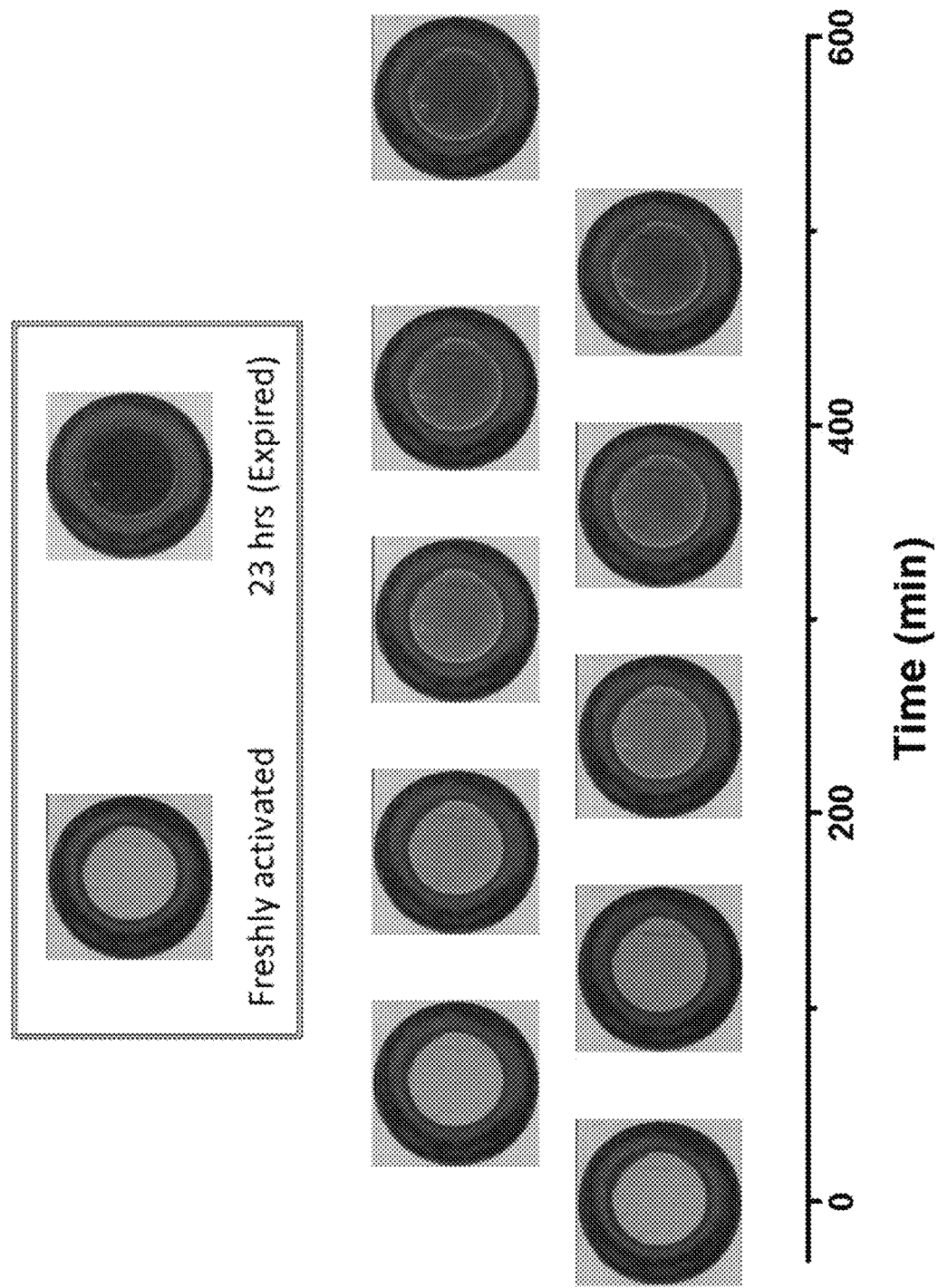
Figure 32B:
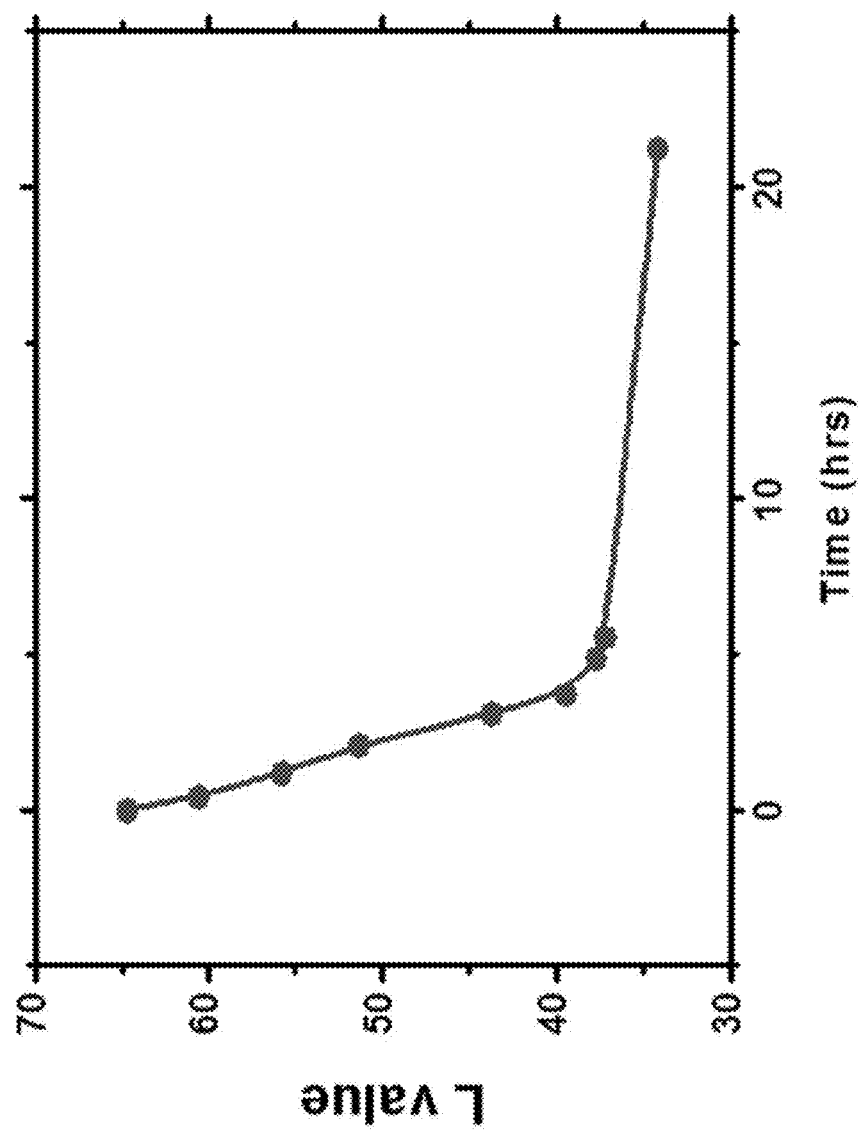
Figure 32C:
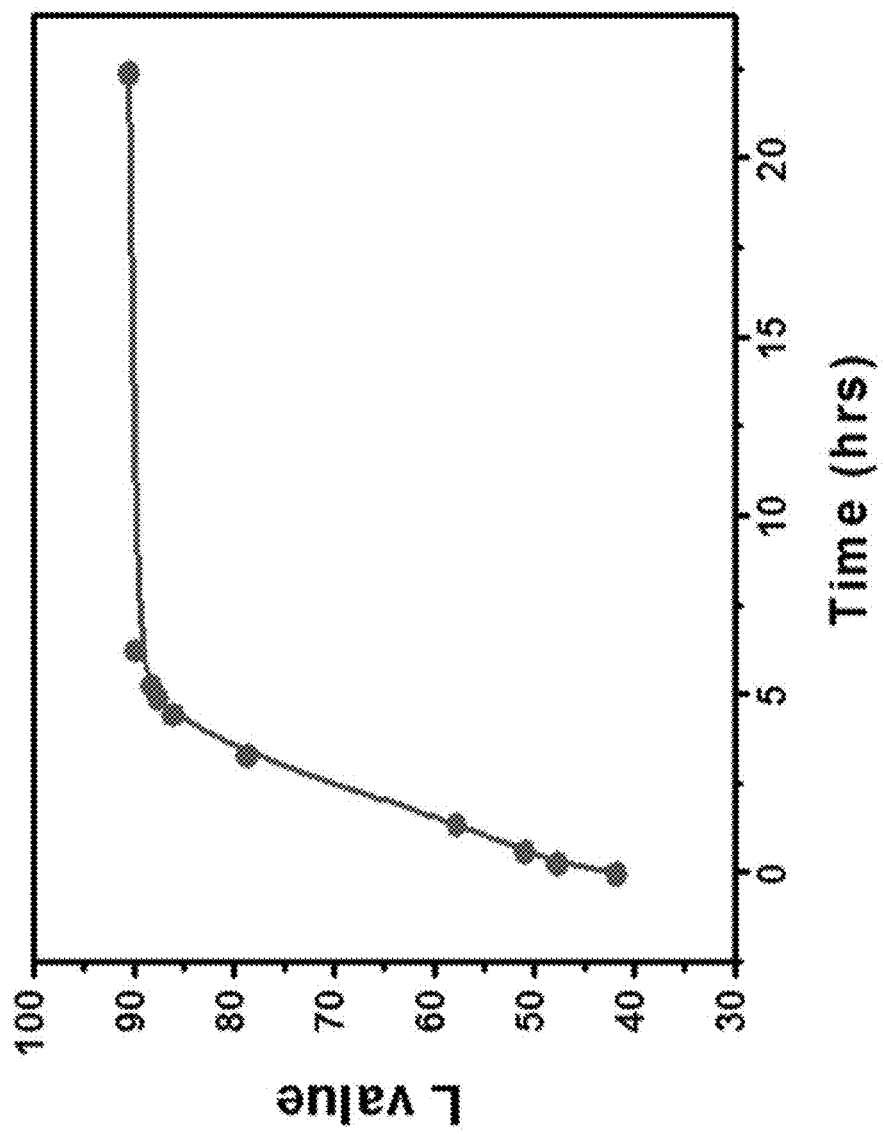
Figure 33:
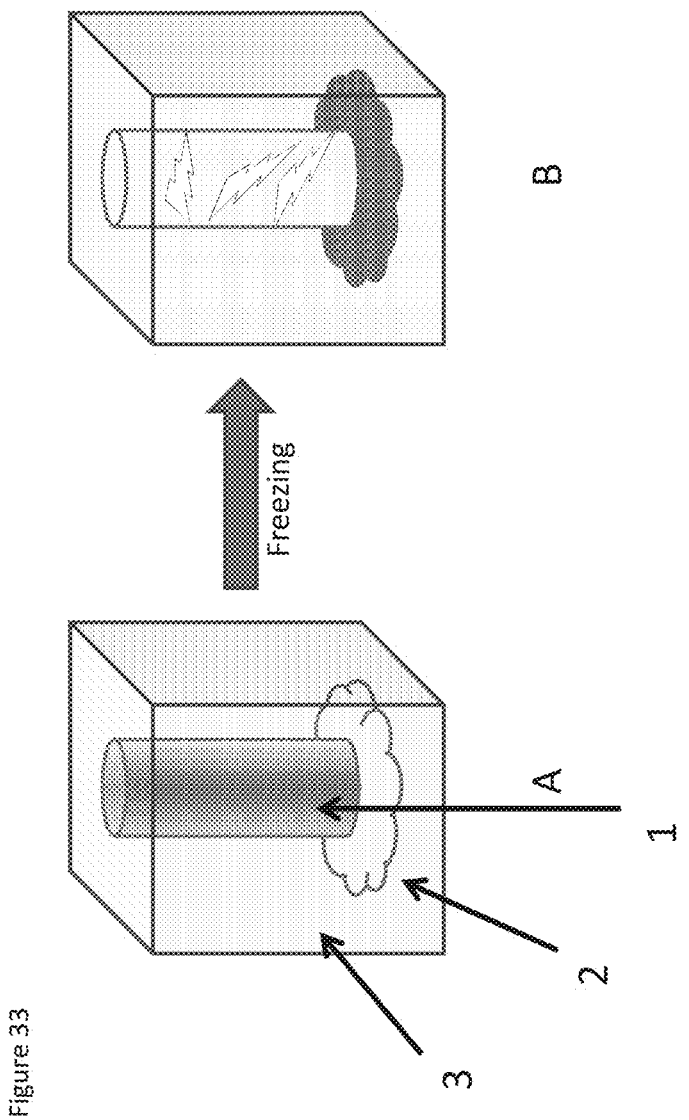
Figure 34:
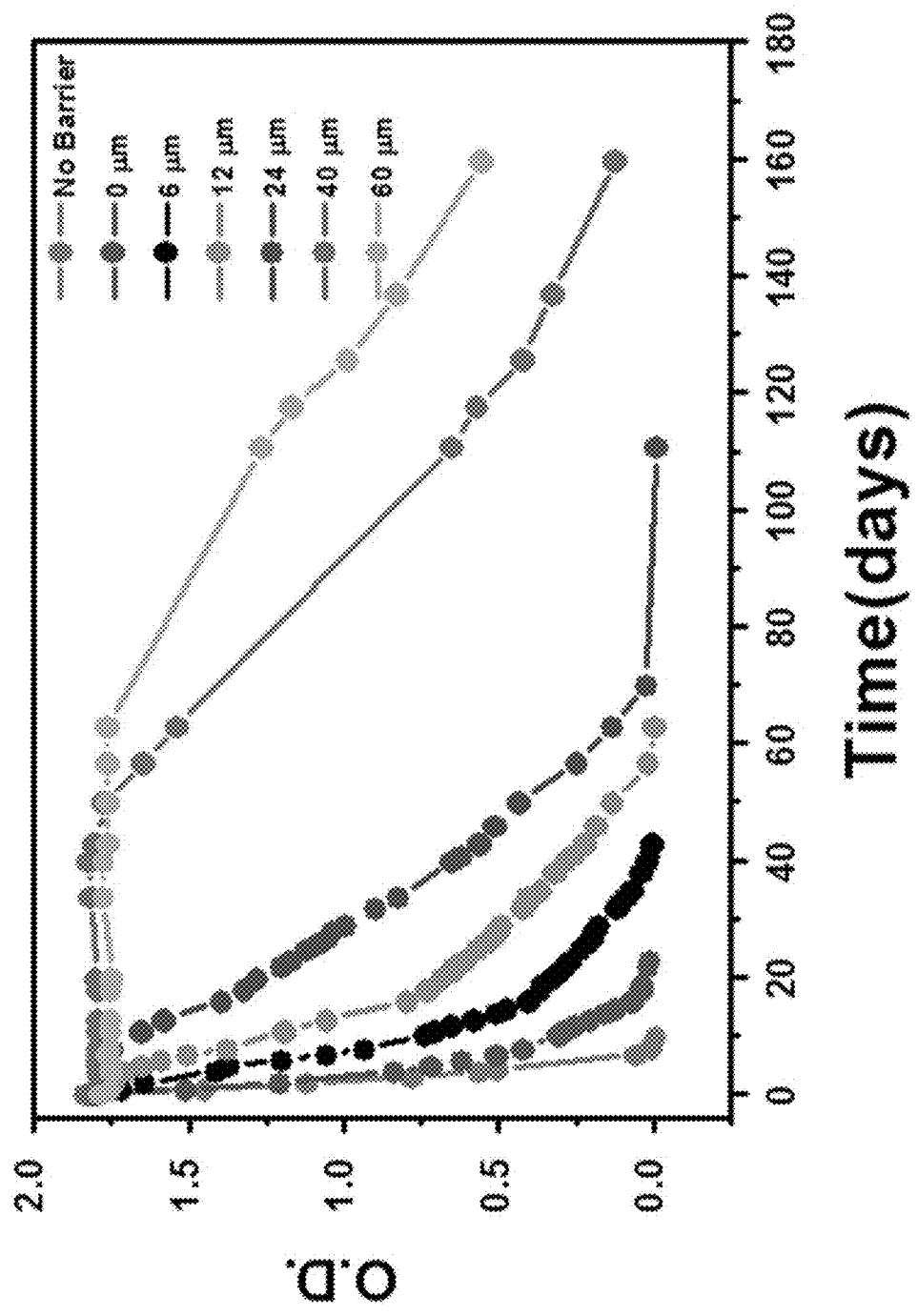

FIGS. 31 A-D show schematic block diagrams of exemplary light to dark TTI devices according to at least some embodiments of the present invention;

FIG. 32A shows such an exemplary light to dark TTI device in a label, indicating the effects of elapsed time;

FIG. 32B shows a graph of CIE-Lab color value of the active spot for an exemplary light to dark TTI device;

FIG. 32C shows a graph of CIE-Lab color value of the active spot for a TTI device that is "dark to light" as described above;

FIG. 33 shows an exemplary FI based upon breaking a sealed container upon freezing; and FIG. 34 shows the optical density as a function of the time after activation of an aluminized TTI label having an alkali soluble polyacrylate polymer printed atop the active aluminum spot by means of flexography.

Figure 35A:
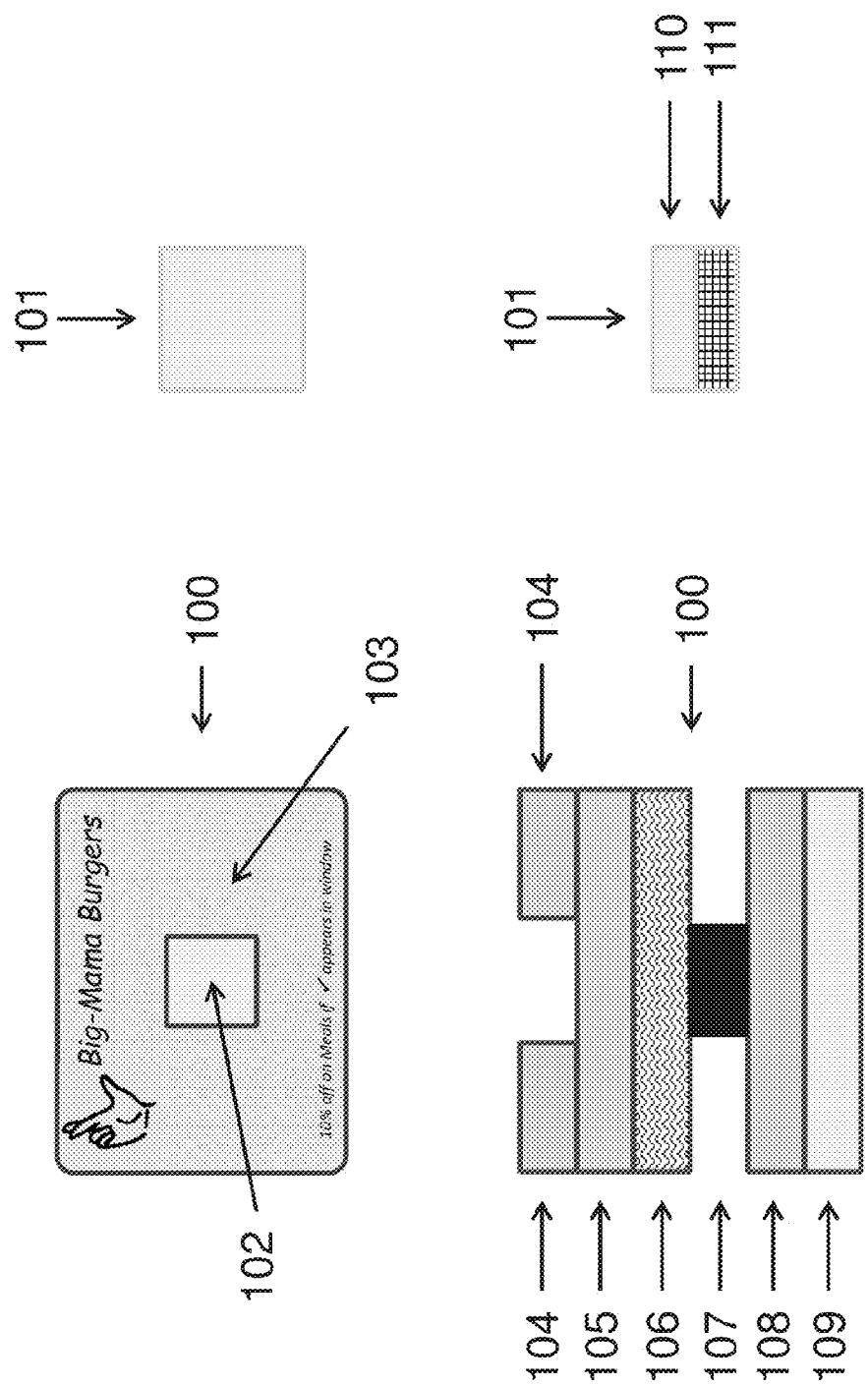
Figure 36:
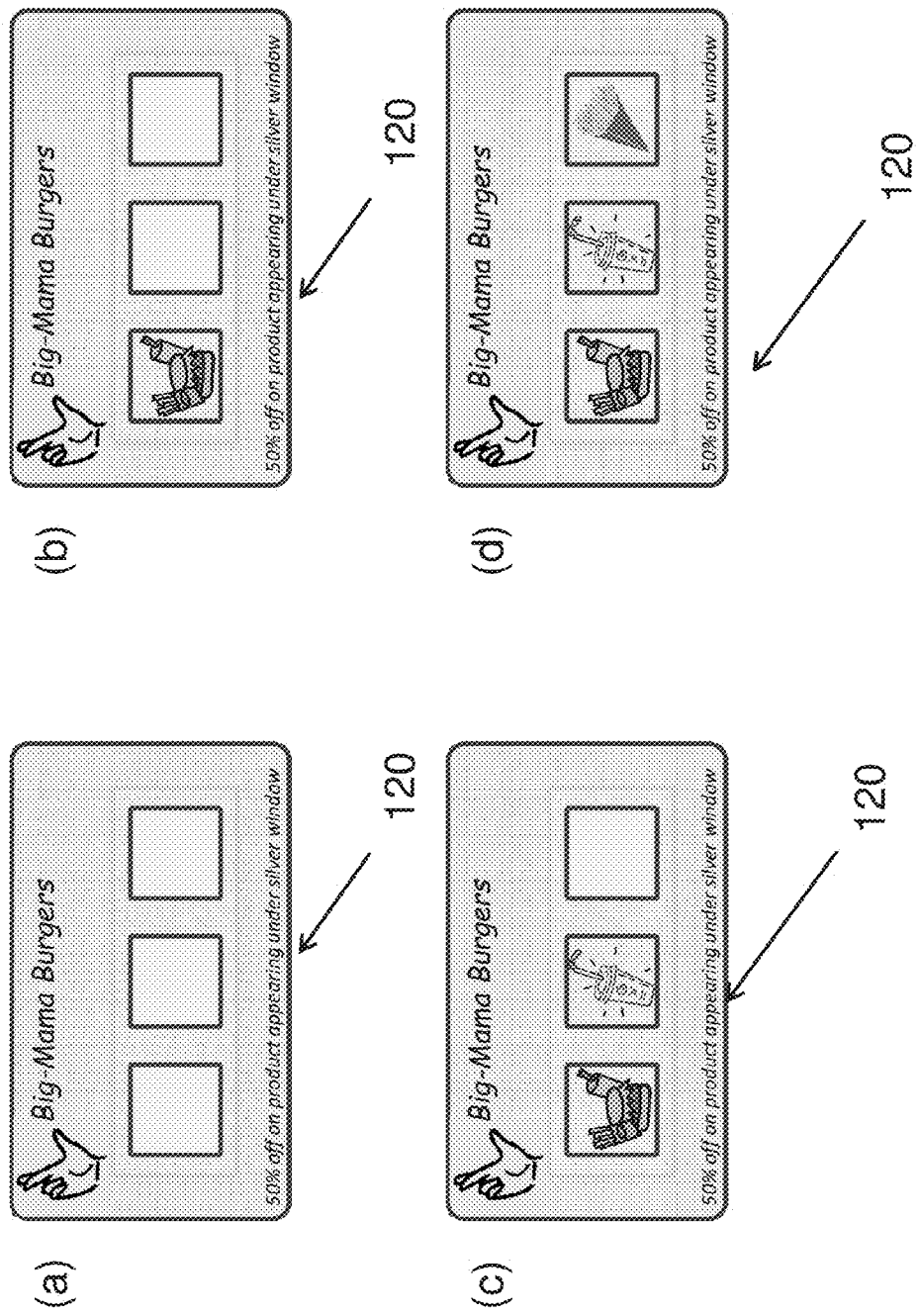

FIGS. 35A-(D-1) show a non-limiting, exemplary detailed implementation of a promotional object according to at least some embodiments of the present invention;

FIG. 36 depicts a multi spot promotional object according to at least some embodiments of the present invention.

Figure 37:
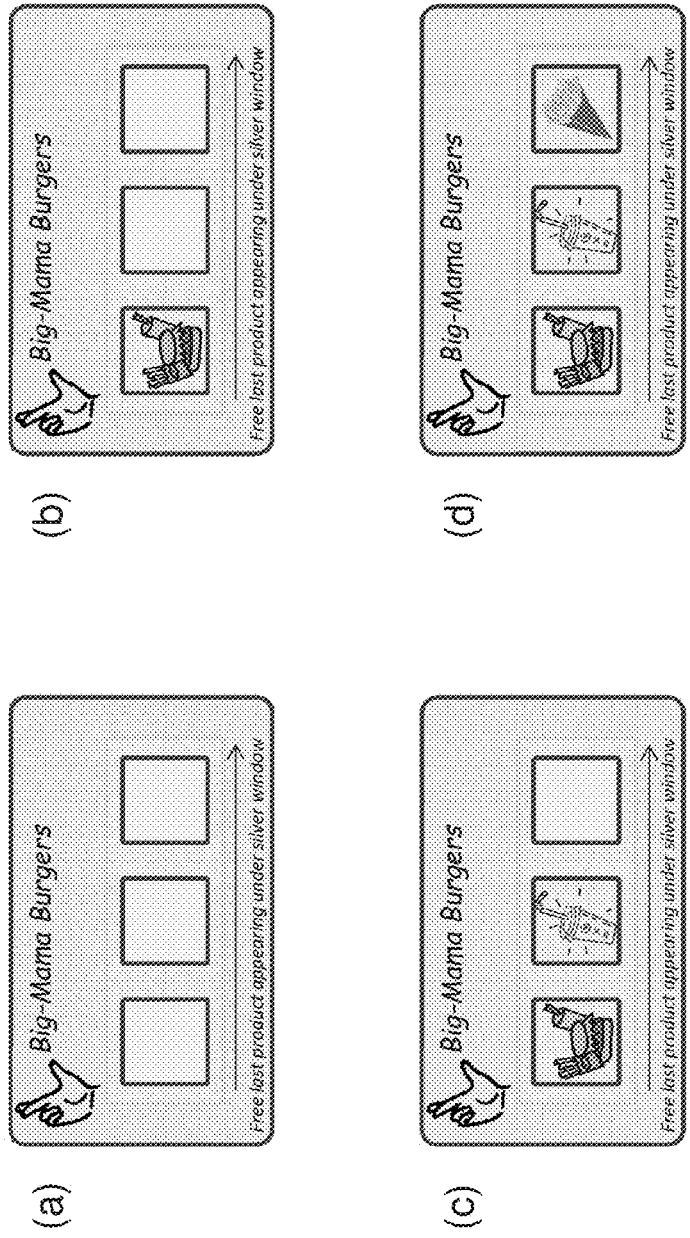

FIG. 37 shows a multi segment object made according to the abovementioned technologies according to at least some embodiments, with different segments showing different visual indications at different time intervals after activation.

Figure 38A:
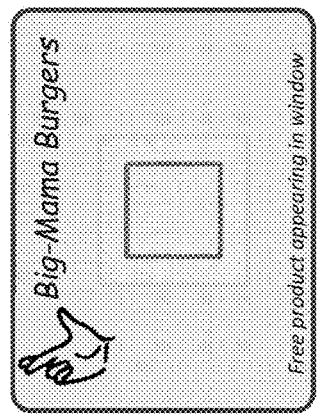
Figure 38B:
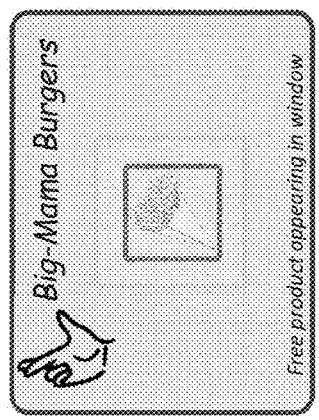
Figure 38C:
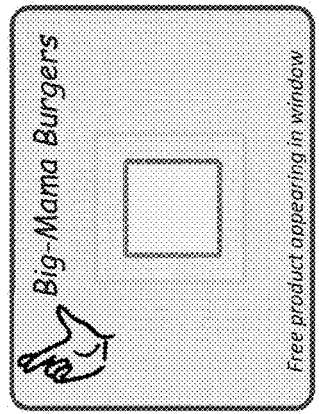

FIGS. 38A-C shows an object according to at least some embodiments in which a single spot reveals latent information after a certain time after activation and then after yet another time interval the revealed information fades and disappears.

Figure 39:
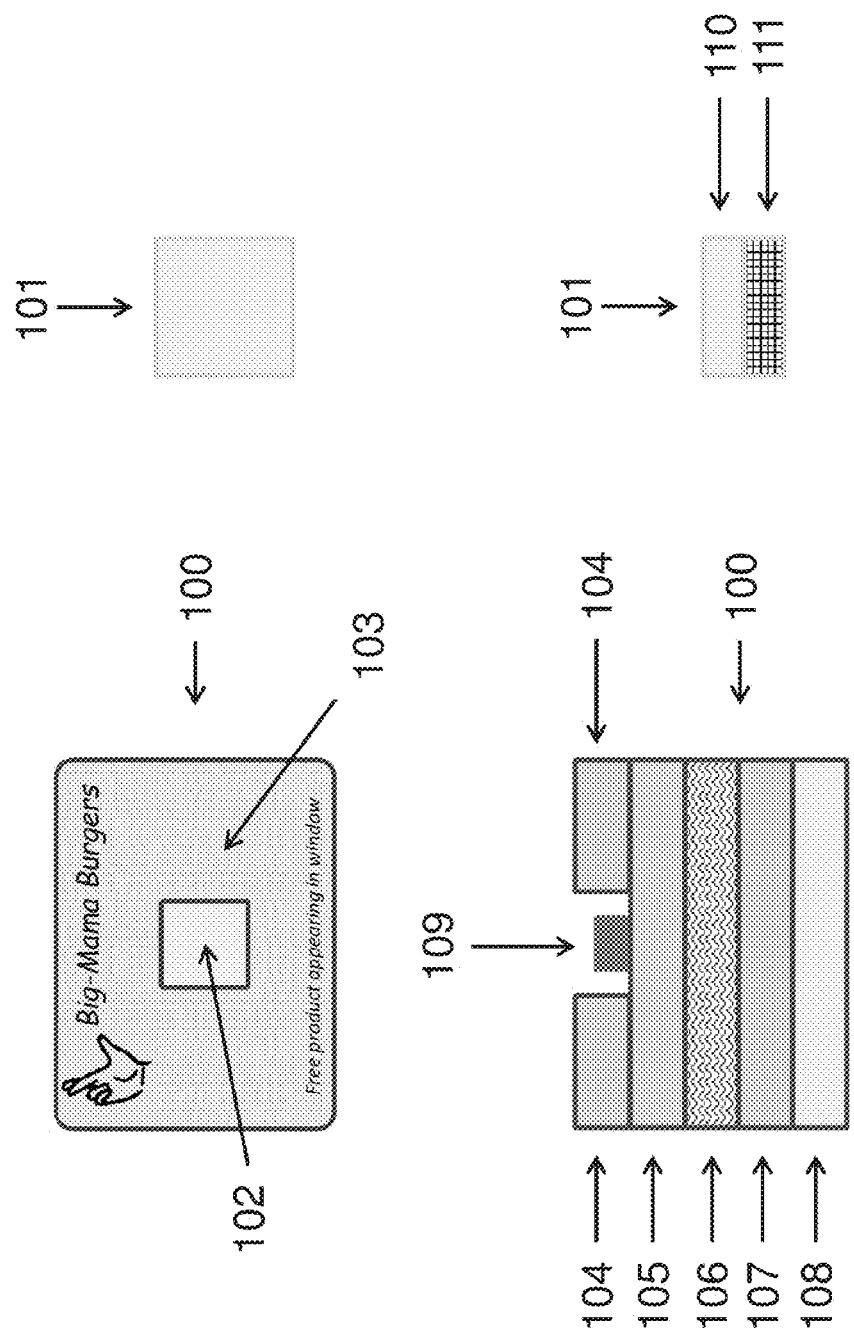

FIG. 39 presents a cross section of a non-limiting example of an object of FIG. 38.

FIGS. 40A-D depict an object in which a plurality of spots reveal latent information at different time intervals after activation and then after yet additional time intervals the revealed information exposed in the different spots they fade and disappear.

Figure 40A:
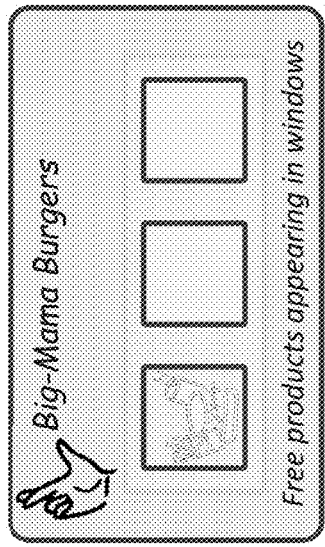
Figure 40B:
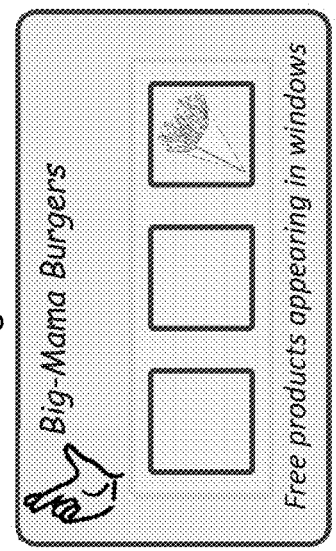
Figure 40C:
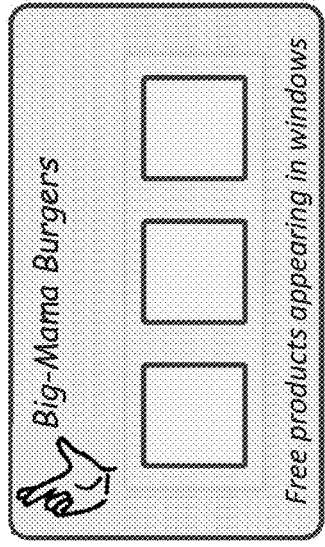
Figure 40D:
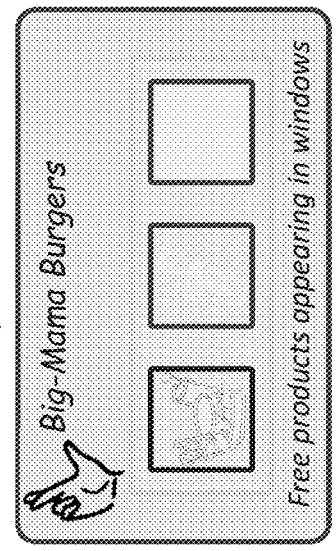
Figure 41:
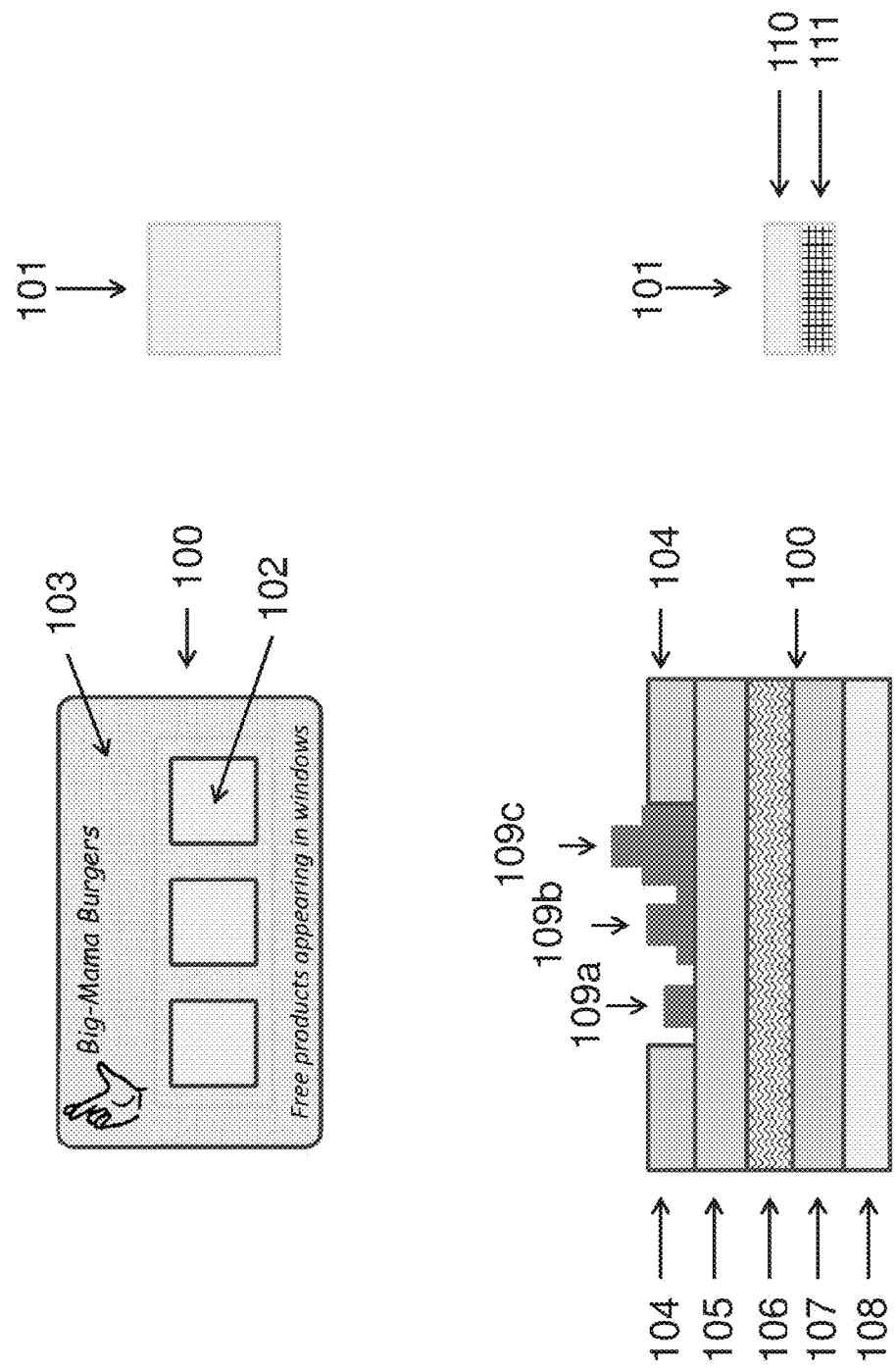

FIG. 41 shows the object of FIG. 40 in cross-sectional detail.

Figure 42A:
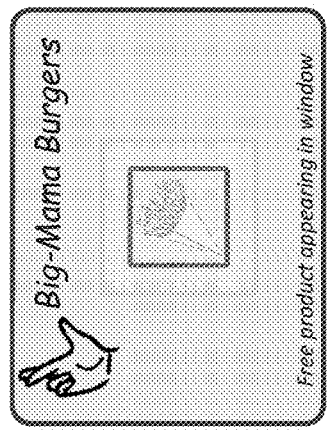
Figure 42B:
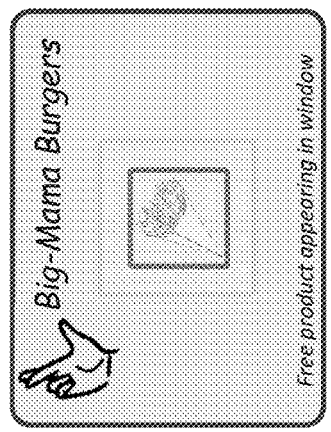
Figure 42C:
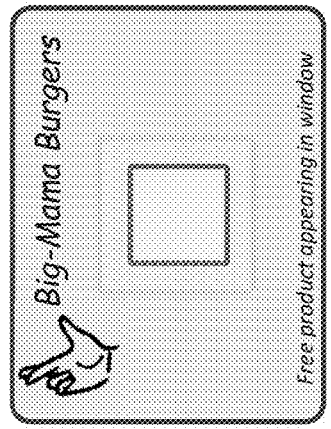

FIGS. 42A-C show an exemplary promotional object in which a single spot reveals latent information after a certain time after activation and the revealed information fades slowly or does not fade at any time that is relevant to the function of the promotional object.

Figure 43:
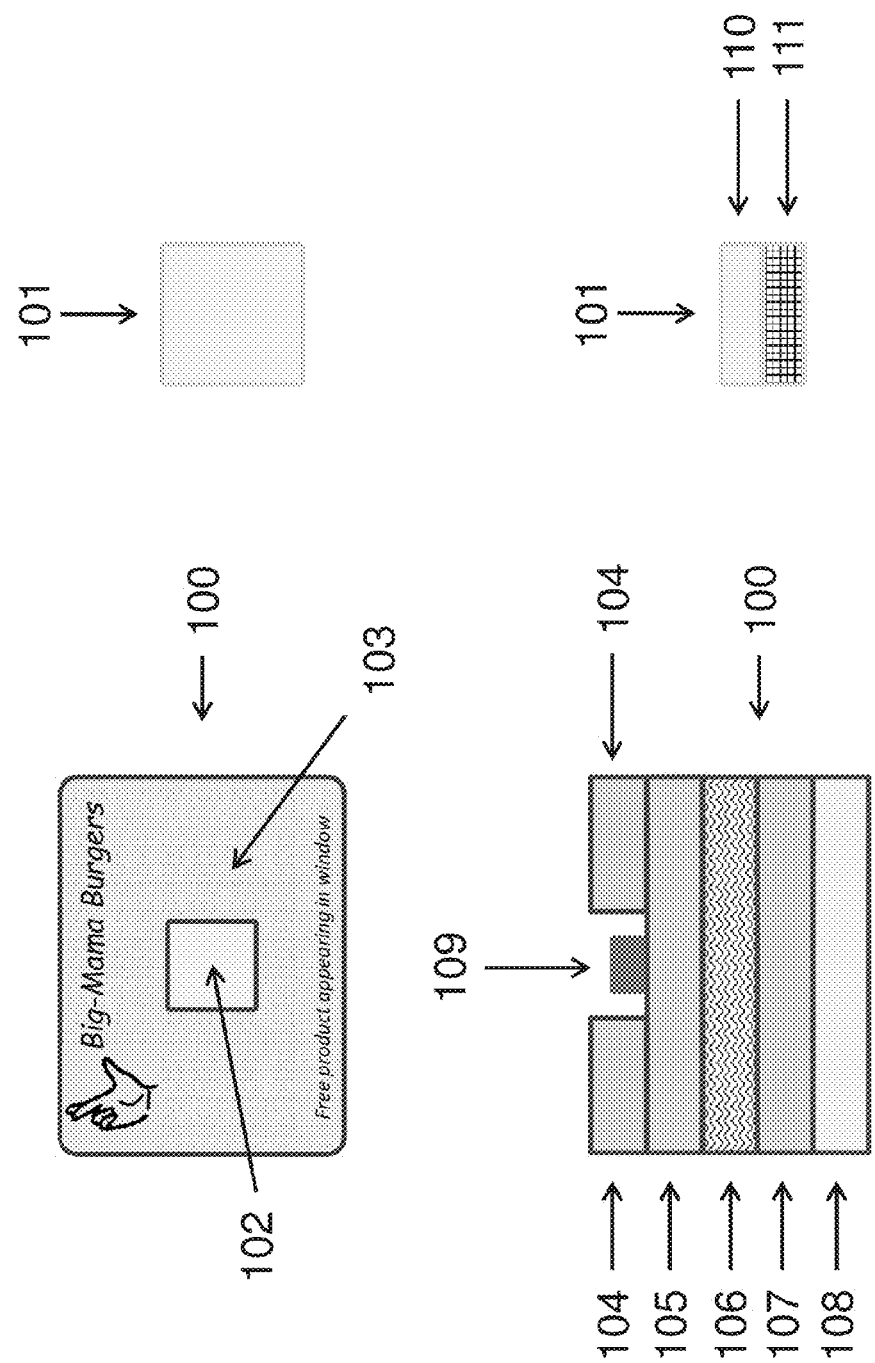

FIG. 43 presents a cross section of a non-limiting example of a promotional object of FIG. 42.

FIGS. 44A-D show a promotional object 103 in which information is revealed in some spots and remains, while such information is revealed in other spots but disappears within a functionally relevant time period.

Figure 44A:
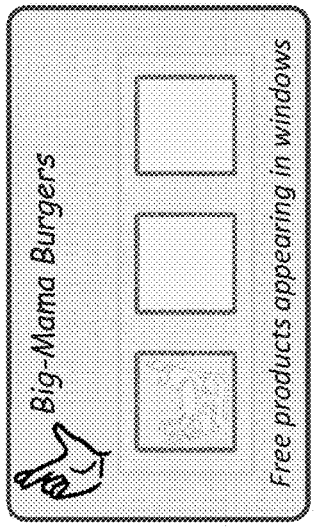
Figure 44C:
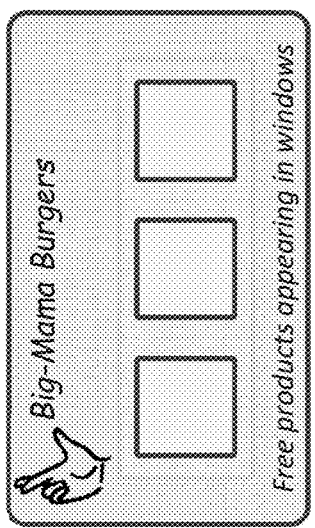
Figure 44B:
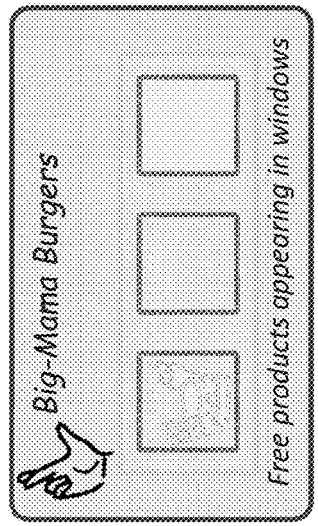
Figure 44D:
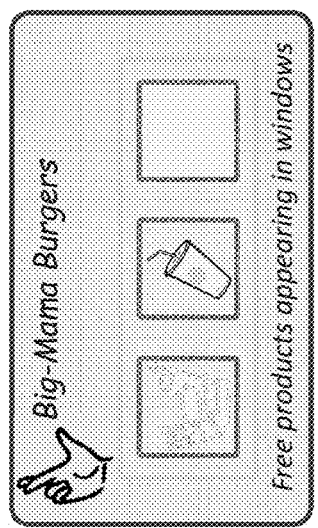
Figure 45:
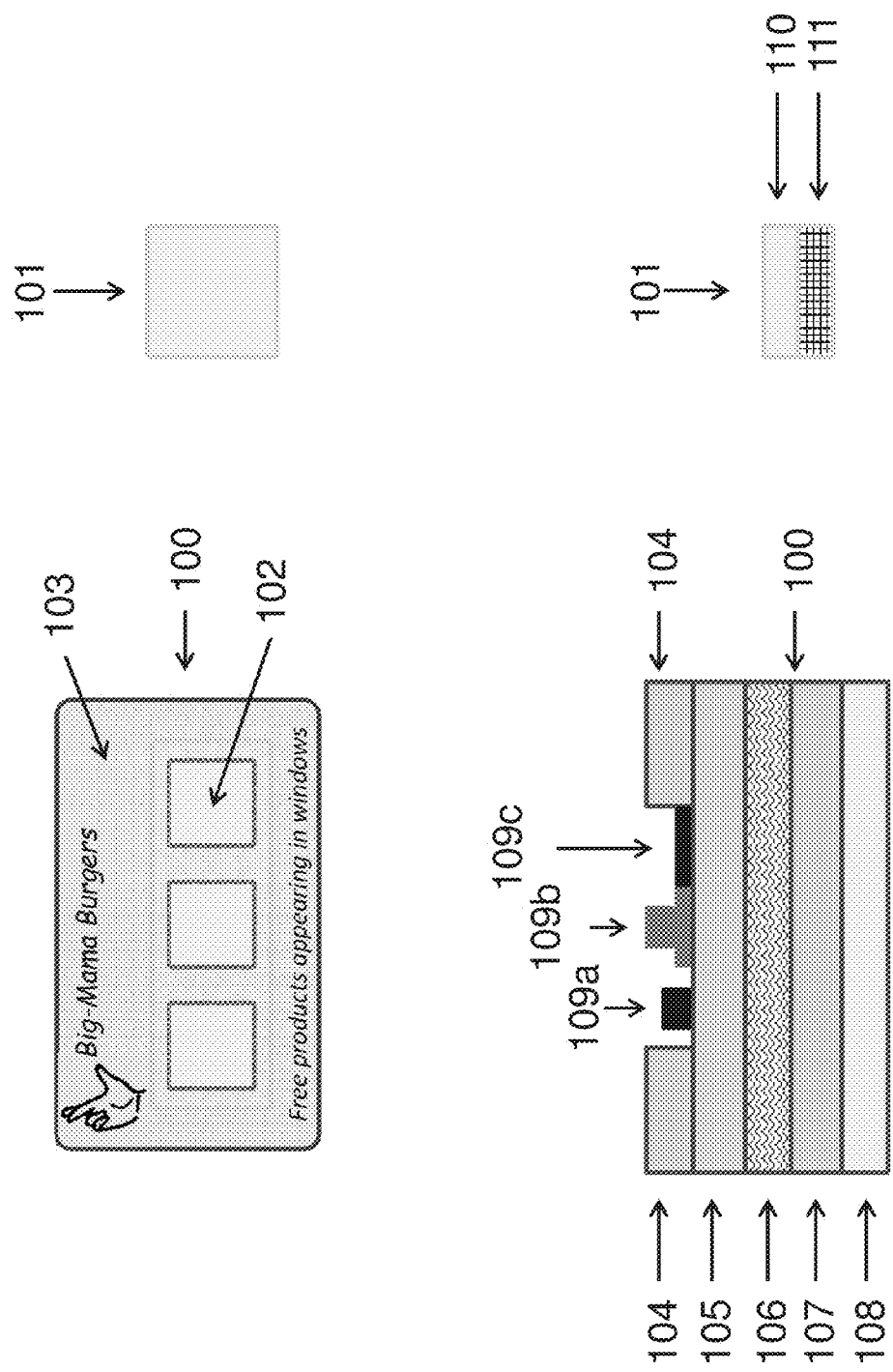

FIG. 45 shows the promotional object 103 of FIG. 44 in cross-section.

Figure 46A:
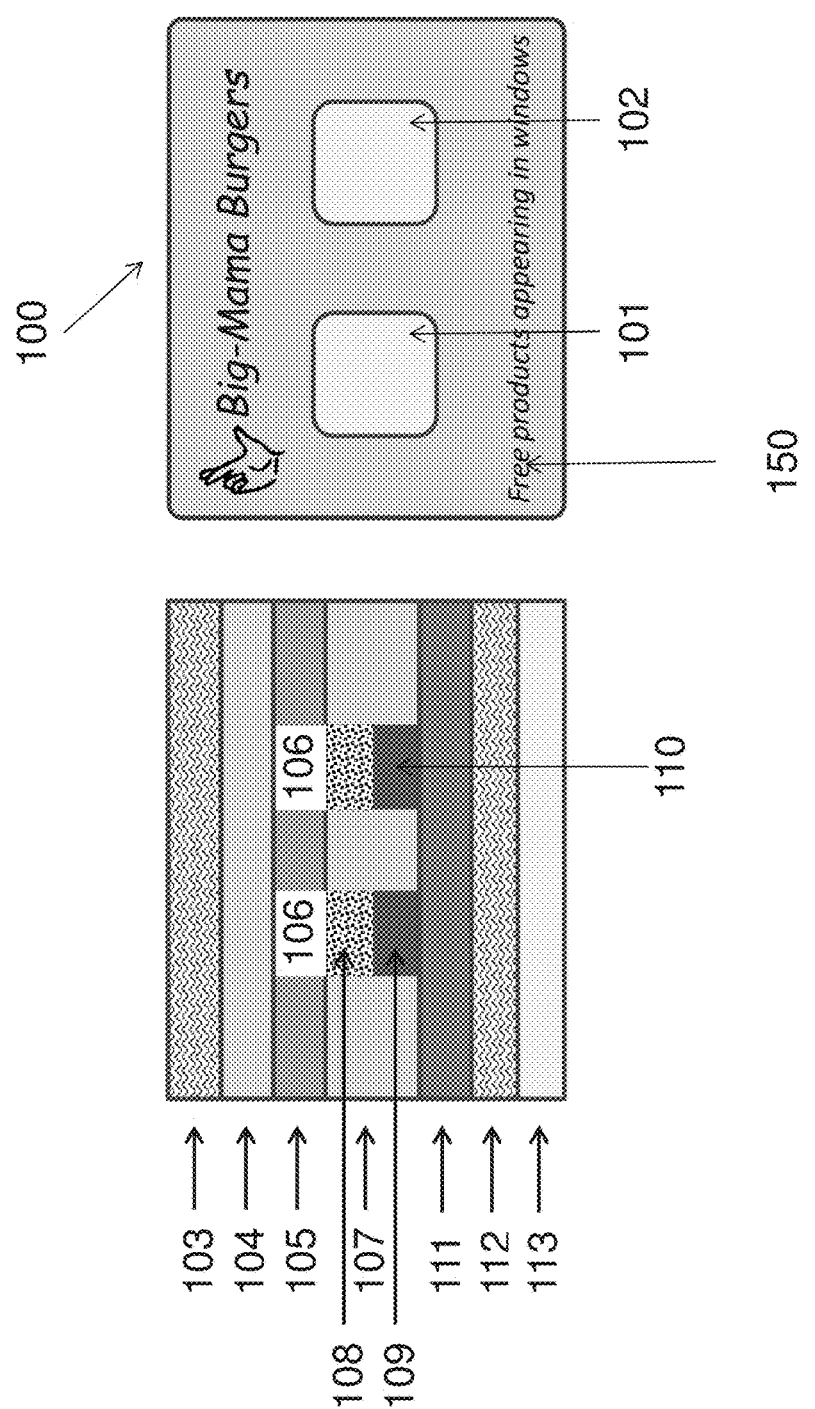
Figure 46B:
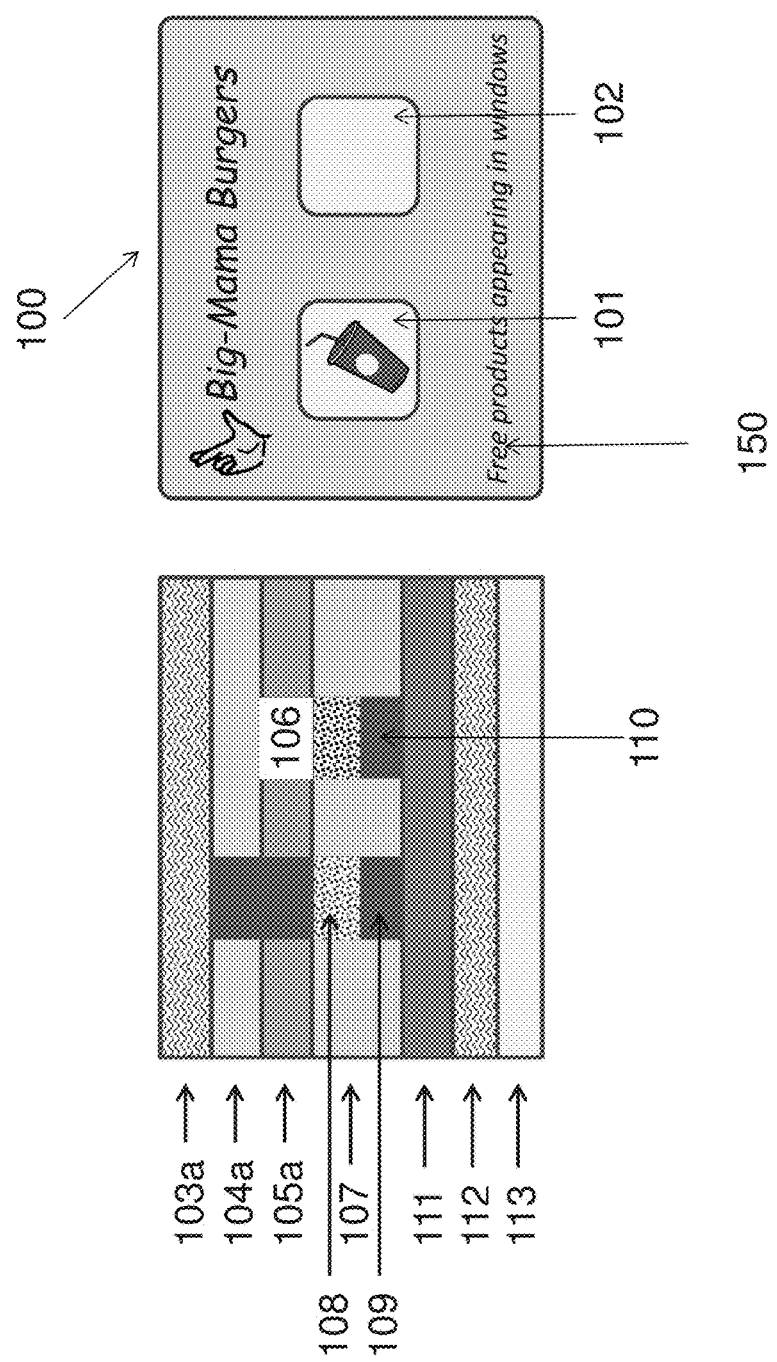
Figure 46C:
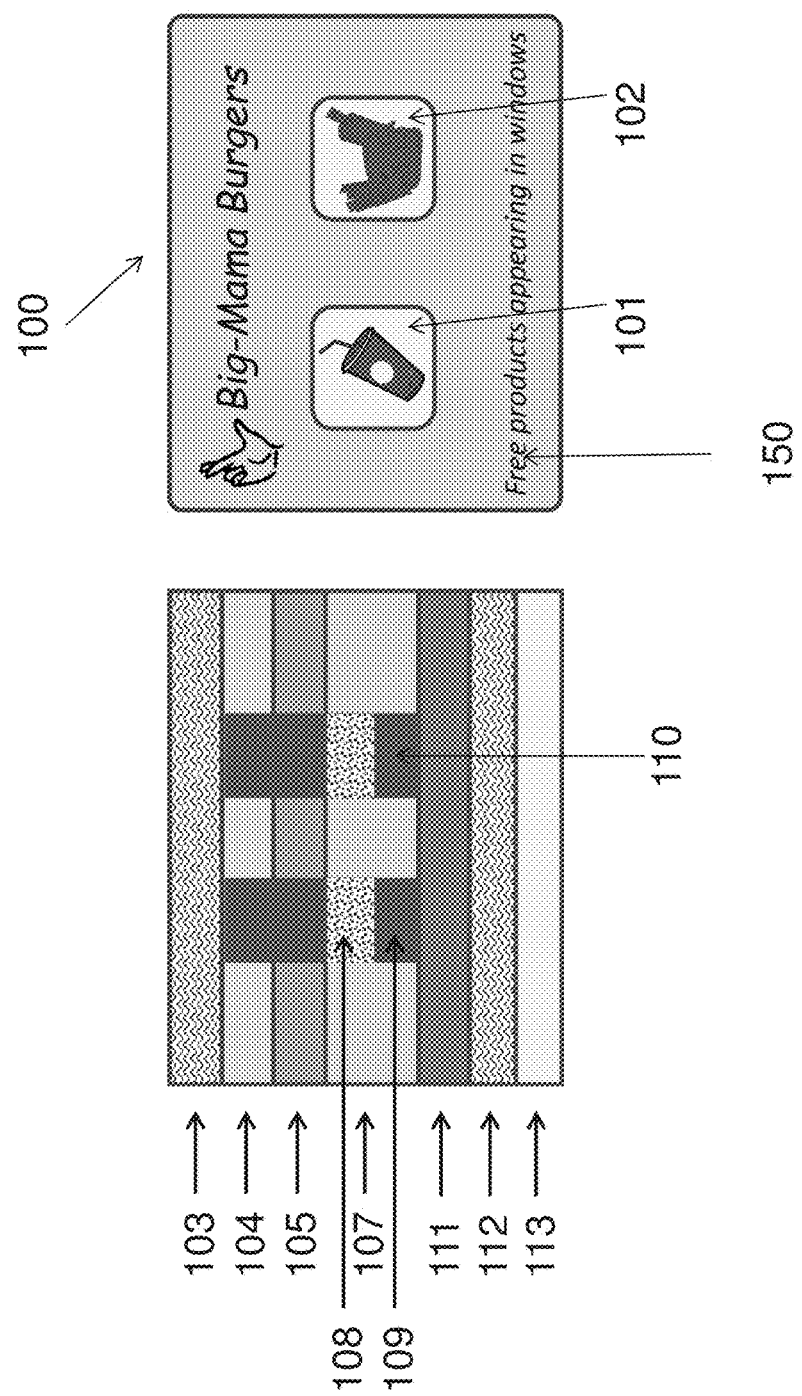

FIGS. 46A-C show a high temperature activated promotional object based on melting of an etchant composition and etching of a layer.

Figure 47A:
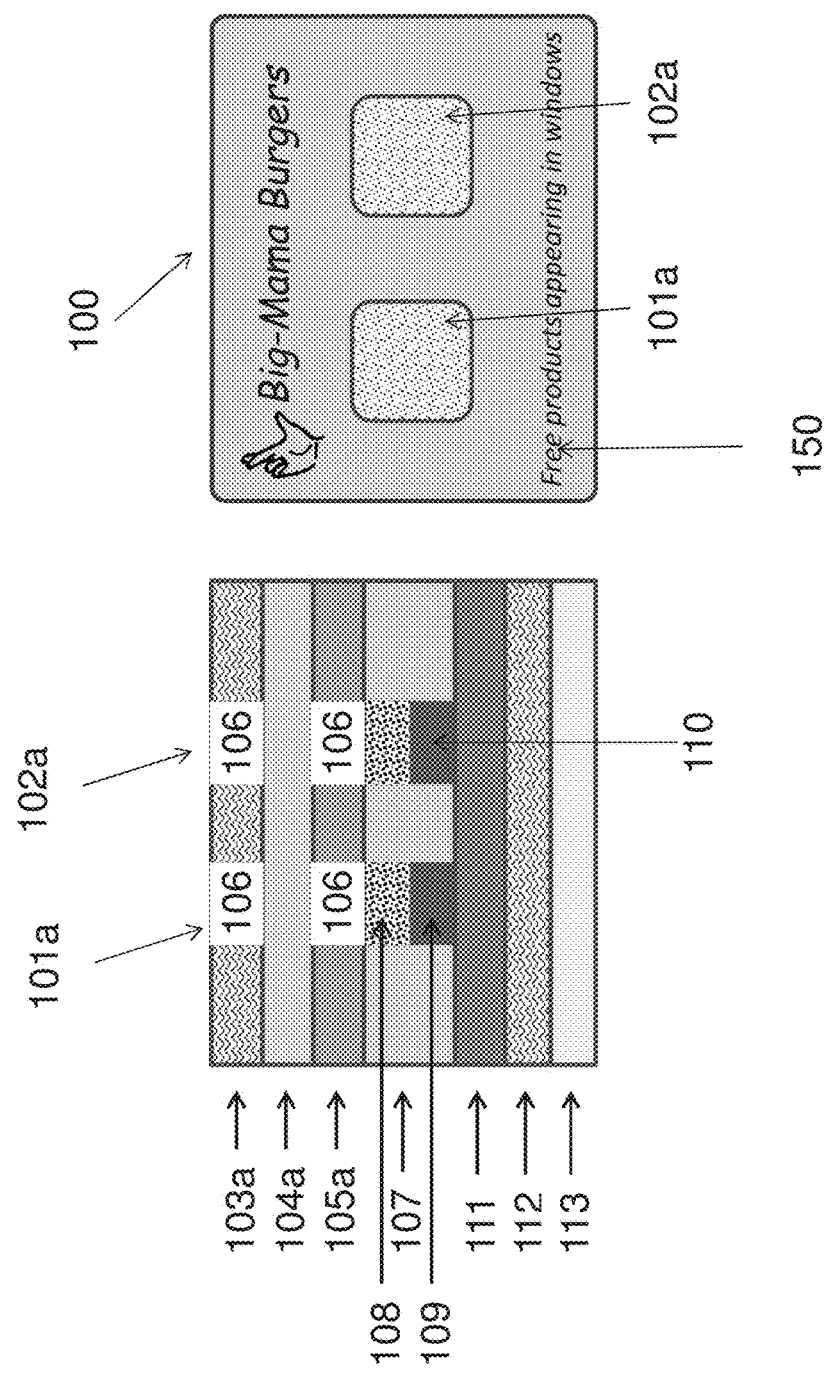
Figure 47B:
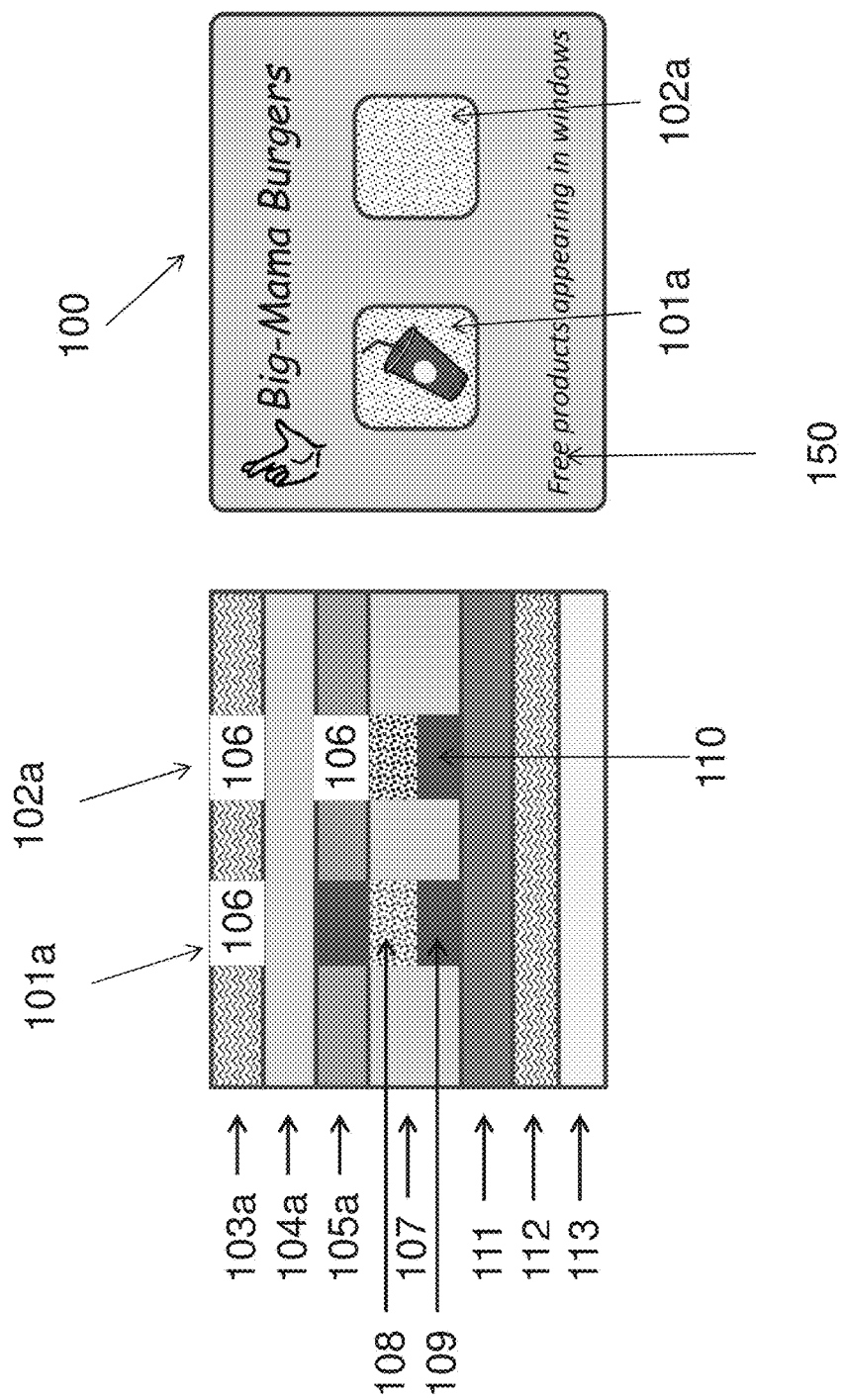
Figure 47C:
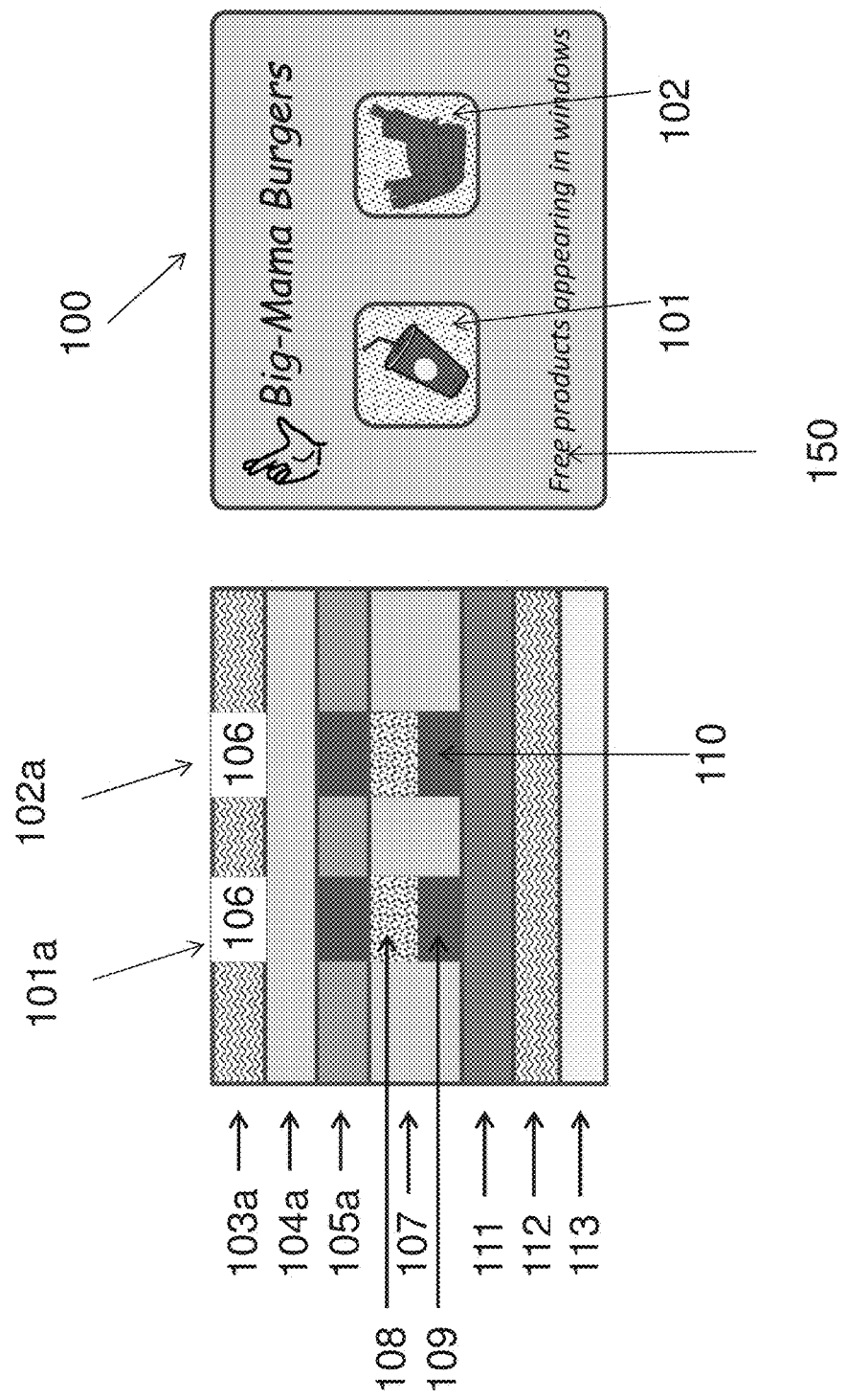

FIGS. 47A-C show a high temperature activated promotional object.

Figure 48A:
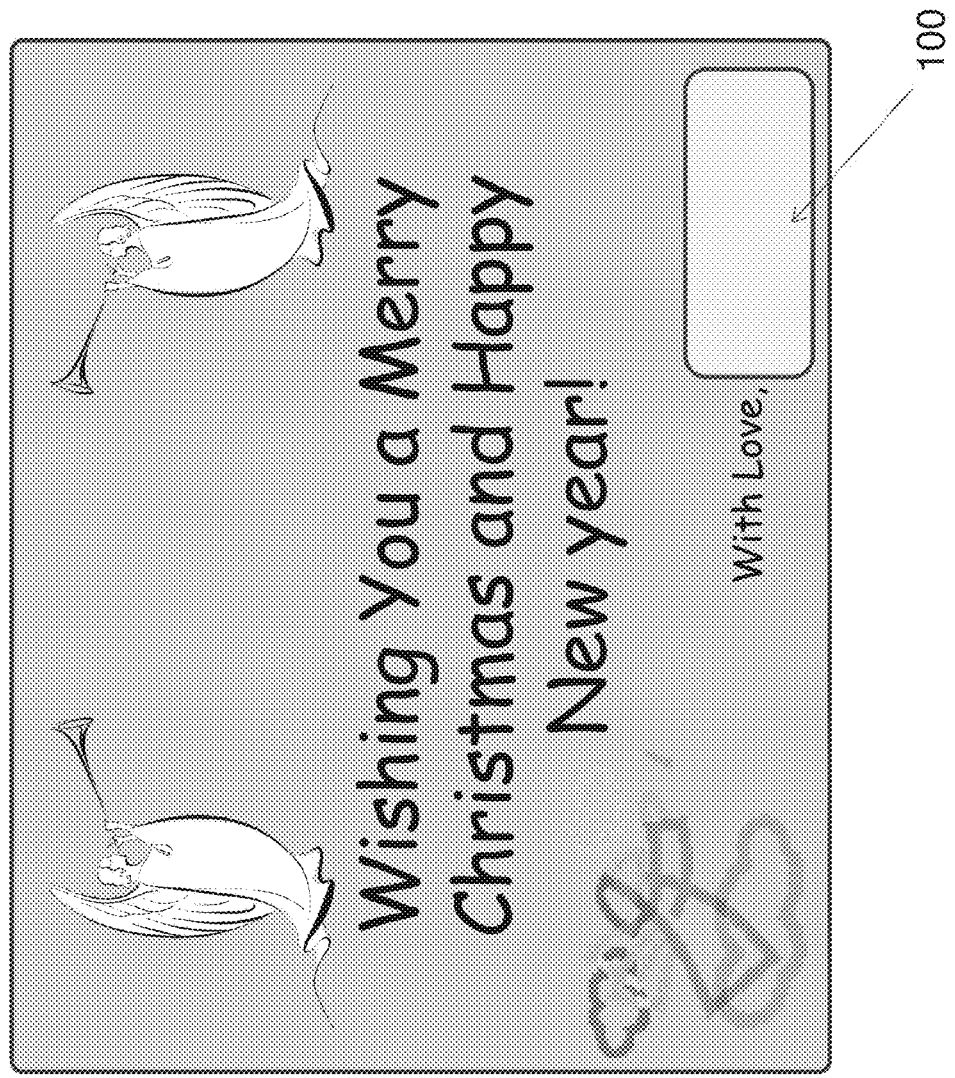
Figure 48B:
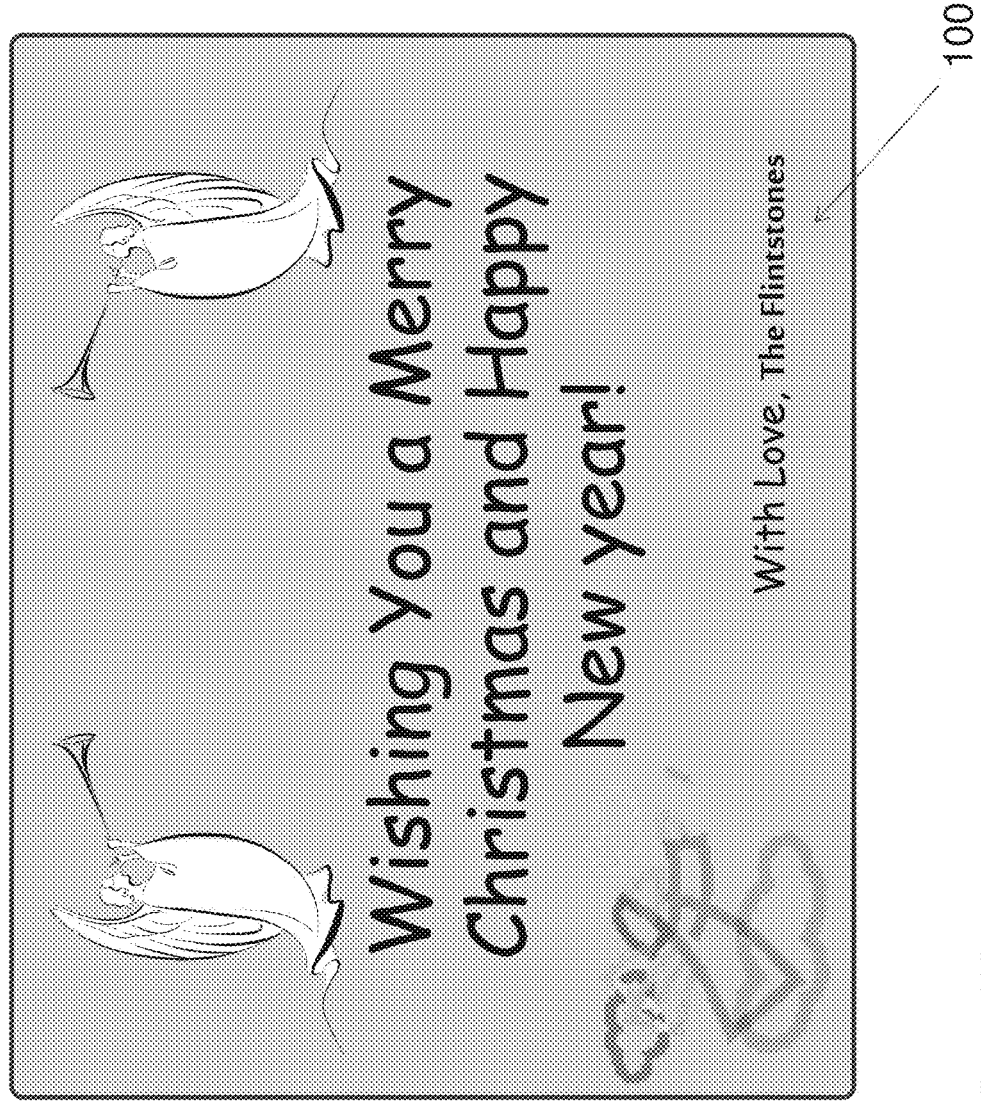

FIGS. 48A-B show a non-limiting example of an entertainment object as a greeting card.

FIGS. 49A-G show another non-limiting example of an entertainment object as a multiple choice story.

DESCRIPTION OF EMBODIMENTS OF THE INVENTION

The present invention, in some embodiments thereof, relates to an apparatus, system and method for a time temperature indicator (TTI) which is capable of providing a summary of the time and temperature history of a good to which it is coupled, optionally including with regard to providing an indication as to whether one or more temperature thresholds have been breached.

According to other embodiments, the TTI specifically provides an indication as to whether a temperature threshold at or around the freeze point has been breached, optionally even without providing a time and temperature history.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

According to at least some embodiments, there is provided a device which includes a substance that has a light characteristic that is altered irreversibly as a function of time and temperature; hence it is used to detect and reflect the time-temperature history to which the product has been exposed. Optionally, rather than a summary of the history, the device detects and reflects an indication as to whether a temperature threshold at or around the freeze point has been breached, optionally even without providing a time and temperature history.

The phrase "light characteristic", as used herein, refers to an intrinsic or an acquired capacity of a substance to interact with light, including emitting, radiating, absorbing, filtering, bleaching, quenching, refracting and/or reflecting.

Examples of a light characteristic include, without limitation, color and chromogenic activity, luminescence, photoluminescence, (e.g., fluorescence, phosphorescence), transparency and reflectivity, including intensities thereof and lifetimes thereof, where applicable.

Thus, according to some embodiments of the present invention, a light characteristic of the probe can be the color and chromogenic activity of the substance and/or its intensity and/or its integrated intensity, the phosphorescence lifetime and/or phosphorescence intensity and/or integrated intensity, and/or the fluorescence intensity and/or fluorescence lifetime, and/or lag time before discoloration, and/or lose of luminescence, and/or discoloration rate, and/or rate of loss of the luminescence, and/or reappearance of color of the probe (coloration), and/or rate of appearance of color of the probe, and/or reappearance of luminescence of the probe, and/or rate of appearance of luminescence, and/or color shift (change) of the probe and/or rate of color shift of the probe and combinations thereof.

Luminescence is a phenomenon in which energy is absorbed by a substance, commonly called a luminescent material, and emitted in the form of light. The absorbed energy can be in a form of light (photons), electrical field or colliding particles (e.g., electrons). The wavelength of the emitted light differs from the characteristic wavelength of the absorbed energy (the characteristic wavelength equals hc/E, where h is the Plank's constant, c is the speed of light and E is the energy absorbed by the luminescent).

The luminescence can be classified according to the excitation mechanism as well as according to the emission mechanism. Examples of such classifications include photoluminescence, electroluminescence, fluorescence and phosphorescence. Similarly, luminescent materials are classified into photoluminescent materials, electroluminescent materials, fluorescent materials and phosphorescent materials, respectively.

A photoluminescent material is a material which absorbs energy in the form of light, an electroluminescent material is a material which absorbs energy in the form of electrical field, a fluorescent material is a material which emits light upon return to the base state from a singlet excitation, and a phosphorescent materials is a material which emits light upon return to the base state from a triplet excitation.

In fluorescent materials, or fluorophores, the electron de-excitation occurs almost instantaneously, and the emission ceases when the source which provides the exciting energy to the fluorophore is removed.

In phosphorescent materials, or phosphors, the excitation state involves a transformation to a spin state which decays only slowly. In phosphorescence, light emitted by an atom or molecule persists after the exciting source is removed usually for a longer time than the respective fluorescence.

The phrases "visible light", "visible spectrum" and "optical spectrum", as these are used herein interchangeably, describe the portion of the electromagnetic spectrum that is visible or can be detected by the typical human eye, and thus electromagnetic radiation in this range of wavelengths is called visible light. A typical human eye can detect, and as a result the human brain can perceive, wavelengths in air from about 380 nm to about 750 nm.

The term "ultraviolet" or "UV", is used herein to describe a portion of the electromagnetic radiation (light) spectrum, spanning wavelengths shorter than that of visible light and longer than X-rays, and encompasses all subranges of UV, as listed in the table below.

| Name | Wavelength range | Energy per photon |
| --- | --- | --- |
| Ultraviolet A (long wave, black light, UVA) Near UV (NUV) | 400 nm-315 nm | 3.10-3.94 eV |
| | 400 nm-300 nm | 3.10-4.13 eV |
| Ultraviolet B (medium wave, UVB) | 315 nm-280 nm | 3.94-4.43 eV |
| Middle UV (MUV) | 300 nm-200 nm | 4.13-6.20 eV |
| Ultraviolet C (short wave, germicidal, UVC) | 280 nm-100 nm | 4.43-12.4 eV |
| Far UV (FUV) | 200 nm-122 nm | 6.20-10.2 eV |
| Vacuum UV (VUV) | 200 nm-10 nm | 6.20-124 eV |
| Extreme UV (EUV) | 121 nm-10 nm | 10.2-124 eV |

As used herein, the term "chromophore" refers to a substance, or a part thereof, that is characterized by a color, such as a colorant, dye or a pigment, as those which are typically used in, for example, inks and paints, and which change in response to temperature. According to some embodiments of the invention, such changes can be detected by the naked eye and/or by various spectrophotometric measurements.

Exemplary food products include natural, whole, raw, fresh, cooked, solid, liquid, liquefied, dried, powdered and otherwise processed plant- or animal-derived food products which provide a source of protein, fat, carbohydrates, vitamins and/or minerals for general sustenance of living, such as, for example, meats, fin-fishes, shell-fishes, dairy products, eggs, fruits, vegetables, honey, grains, herbs, nuts, coffee, tea and food additives, and any combination thereof. Specifically, the units, systems, articles and methods presented herein are useful in the food manufacturing, processing, distributing and retail industries to monitor the freshness and general quality of raw materials as well as finished goods, such as fresh meat and fish which are prone to oxidation or decomposition by microorganisms.

Exemplary nutraceutical products include, but are not limited to, powders, syrups, gels, tablets, pills, capsules and/or other forms of food additives, dietary supplements, probiotic products containing live beneficial microorganisms (e.g., probiotic microorganisms), food derived products or food extracts, typically used to enhance, improve, maintain or protect human well being and health.

Exemplary pharmaceutical products include, but are not limited to, tablets, pills, capsules and/or other forms of encapsulated, as well as bulk powdered, pelletized and granulated pharmaceutical substances, liquid pharmaceutical substances such as drug solutions, blood, serums, plasma and other bodily fluids and products thereof, or solid pharmaceutical substances used for the treatment of human or animal ailments or diseases.

Pharmaceutical products therefore encompass drugs for internal consumption via, for example, oral or systemic administration.

Pharmaceutical products further encompass, for example, bodily organs or tissues to be implanted in a subject, including blood and components thereof, liver, heart, cornea, retina, and the like, which should be maintained at an appropriate temperature and without breaching one or more temperature thresholds during the transplantation process.

Thus, exemplary temperature-sensitive products encompass drugs, cosmetic and cosmeceutical products for topical, nasal, mucosal, ophthalmic administration, for administration by inhalation and/or for administration via any other route.

Exemplary cosmetic and cosmeceutical products include, but are not limited to, products in the form of solutions, oils, ointments, pastes, gels, lotions, milks, suspensions, powders, aerosols, sprays, foams, shampoos, hair conditioners, lacquers, makeups, solid sticks and toothpastes.

An exemplary list of cosmetic and cosmeceutical products that can benefit from the methodology described herein include, without limitation, lip glosses, lipsticks, toothpastes, hair products and nail polish/lacquers.

According to at least some embodiments, the present invention features a TTI alone, a threshold indicator alone or a combination thereof.

Threshold indicators are single-use disposable indicators that are aimed at reporting a temperature excursion to temperatures that are above a set limit. Threshold indicators are used to monitor products that can be damaged when exposed to high temperatures, such as vaccines and other biological macromolecular materials that tend to undergo denaturation at elevated temperatures. The threshold indicator is designed to undergo an irreversible and tamper-resistant color change when exposed to temperatures above a set limit.

Overview and Metal Based TTI Devices

Figures 1, 1A:
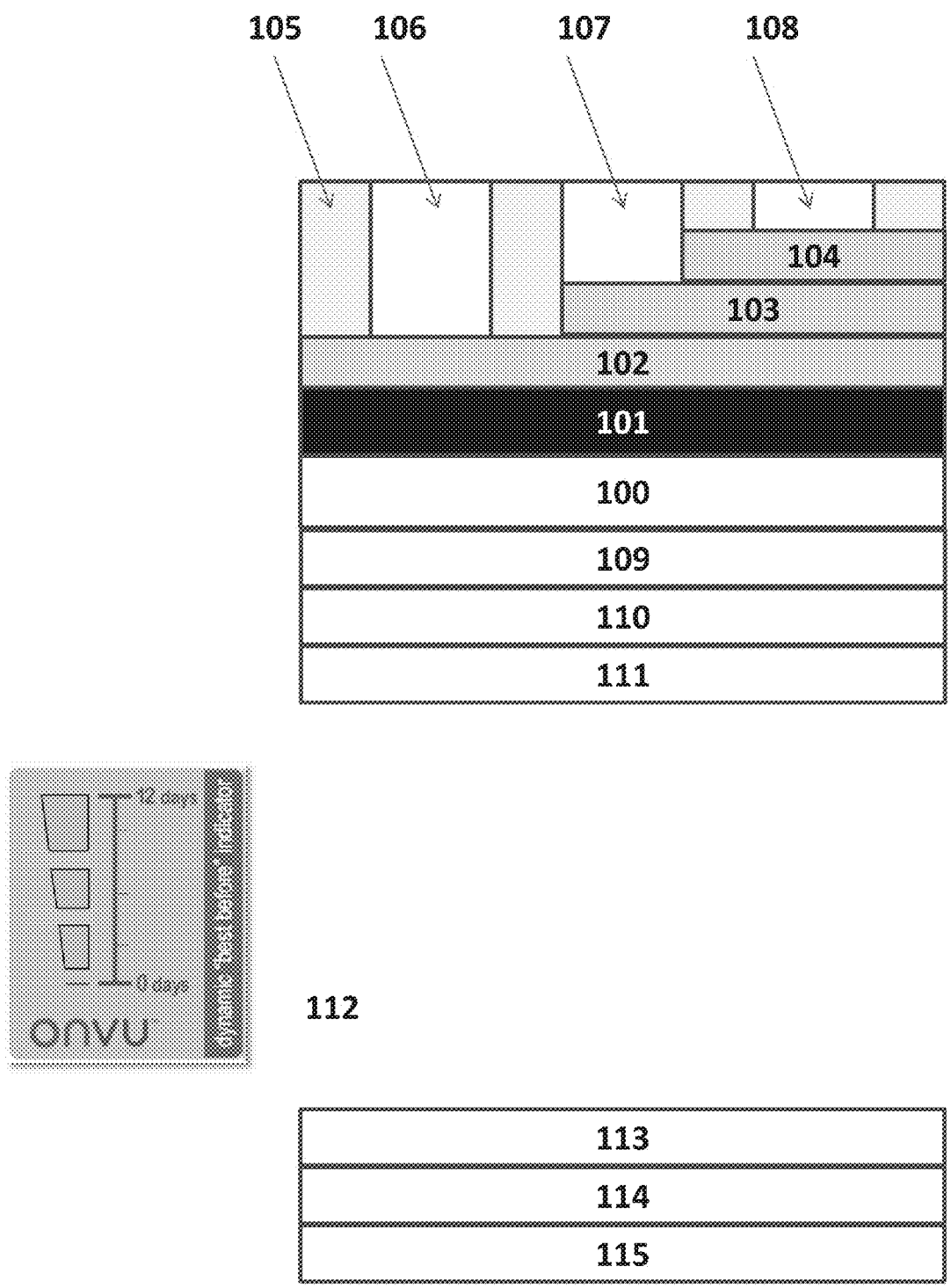
FIGS. 1A-1 and 1A-2 presents schematic illustrations of an exemplary TTI and its resulting kinetics at different temperatures according to at least some embodiments of the present invention.

Turning now to the drawings, FIG. 1 (with multiple parts) shows an overview of metal-based TTI devices and also some threshold indicators.

Figures 1, 1A, 2:
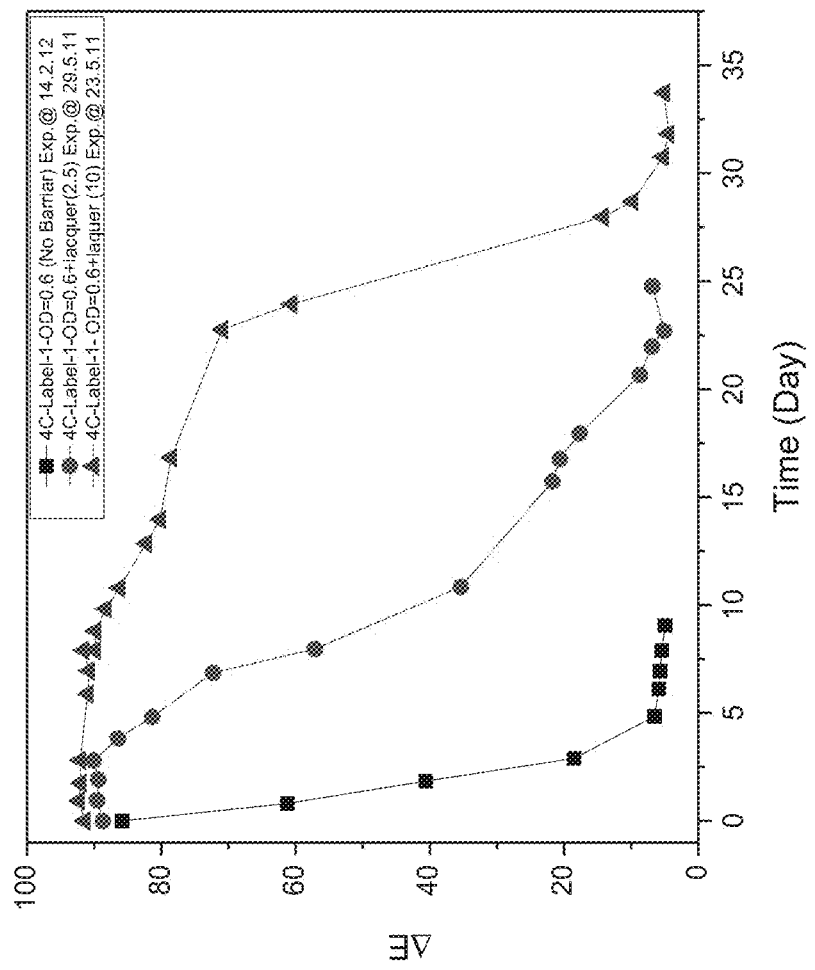

FIG. 1A-1 presents a schematic illustration of an exemplary TTI according to at least some embodiments of the present invention, while FIG. 1A-2 shows the kinetics of the behavior of this exemplary TTI.

FIG. 1A-1 shows a schematic diagram of an exemplary metal-based TTI with a plurality of layers. A 36 μm transparent PET film (100) coated with aluminum (PVD, O.D=0.6) (101) was loaded on a flexography machine (Arsoma 410S, Gallus) and the aluminum side was printed with three layers of a UV curable colorless primer (UVT 00041, Flint) (102, 103, 104), each of which hereinafter referred to as a barrier, forming a staircase-like layered film of increasing thickness. The web was then printed with three layers of white and one layer of yellow (105), leaving three openings in the form of trapezoid rectangles in a way that each trapezoid reveals a different layer of UV curable colorless primer (trapezoid openings 106, 107 and 108 exposing layers 102, 102+103 and 102+103+104 respectively). It should be noted that FIG. 1A is not drawn to scale and that while the width of the trapezoid openings is normally in the mm range, the thickness of the barrier and aluminum layers typically is in the range of nm to microns.

The first side of the label was finished by adding pictograms and logo. The web was then inverted on the machine and one layer of primer, one layer of yellow then two layers of white were printed sequentially atop the PET side (all layers combined in 109). The web was then covered with a pressure sensitive adhesive at the PET side (110) terminated with a siliconized release layer (111), slit and die cut, forming finished "active reactant" labels (112).

The "passive reactant" label of a TTI was produced on a reverse gravure coating machine. A 36 μm transparent PET film (113) was coated with a 25 μm thick layer of a mixture of a pressure sensitive adhesive and phosphoric acid (114). The web was then terminated with a siliconized release layer (115), slit and die-cut into finished labels (not shown).

The TTI was activated by adhering a "passive reactant" label to the aluminum side of the "active reactant" label. Again, it should be noted that FIG. 1A-1 is not drawn to scale and that while the width of the trapezoid openings is normally in the mm scale, the thickness of the barrier and aluminum layers is typically in the range of nm to microns. Consequently, the gaps between the barrier layers and the adhesive layer do not appear in reality. Initially, the three trapezoid spots had a mirror-like, shiny appearance. In a next step, the metallic surfaces lose their shiny appearance and turn dark. As time-temperature elapses, the aluminum layer is consumed sequentially, one trapezoid after the other (that is, the trapezoid openings are consumed in the following order: trapezoid openings 106, then 107, then 108 in the above described case) revealing the yellow color underneath. The color progression process normally does not follow a single exponent decay but is rather characterized by a lag period, with a duration that depends on the composition and thickness of the printed barrier and the temperature. Next, the color change progresses at a rate that is temperature dependent, often resembling a single exponent decay. In other embodiment the color change of this step resembles more of a staircase.

The results of this functionality and set of layers are shown in FIG. 1A-2 showing the color change as a function of the time of a TTI label that is a combination of (112) and the previously described die-cut label at stored at 4 C. Black rectangles show the rate of color change of the first trapezoid having a very thin barrier, red circles show the rate of color change of the second trapezoid having thicker barrier and blue triangles show the rate of color change of the third trapezoid having even thicker barrier.

FIG. 1A-3 shows an exemplary TTI that features both a threshold indicator and a time-temperature history indicator (in both non-limiting examples, the threshold indicators cause the word "EXPIRED" to become visible, for example optionally in red letters (latent before crossing at least one of the threshold temperatures). It should be noted that the threshold indicators turn-on may be expressed in other words and/or symbols and may come in one symbol or a plurality of symbols, separated or together (for example as presented in the figure).

According to at least some embodiments, the threshold indicator develops at a precise temperature point, but alternatively may develop in a range of a few degrees on either side of this precise temperature point, according to the material used and the thermal coupling between the perishable good and the temperature sensitive material. As non-limiting examples, the temperature point may optionally be selected from −40 C to +100 C, preferably is selected from −10 to 60 C and more preferably is in the range of at least +2 to +8° C. The time required for the threshold indicator to develop is optionally between a fraction of a second to several hours and even days and months, depending on configuration and embodiment.

Figures 1, 1A, 2, 3:
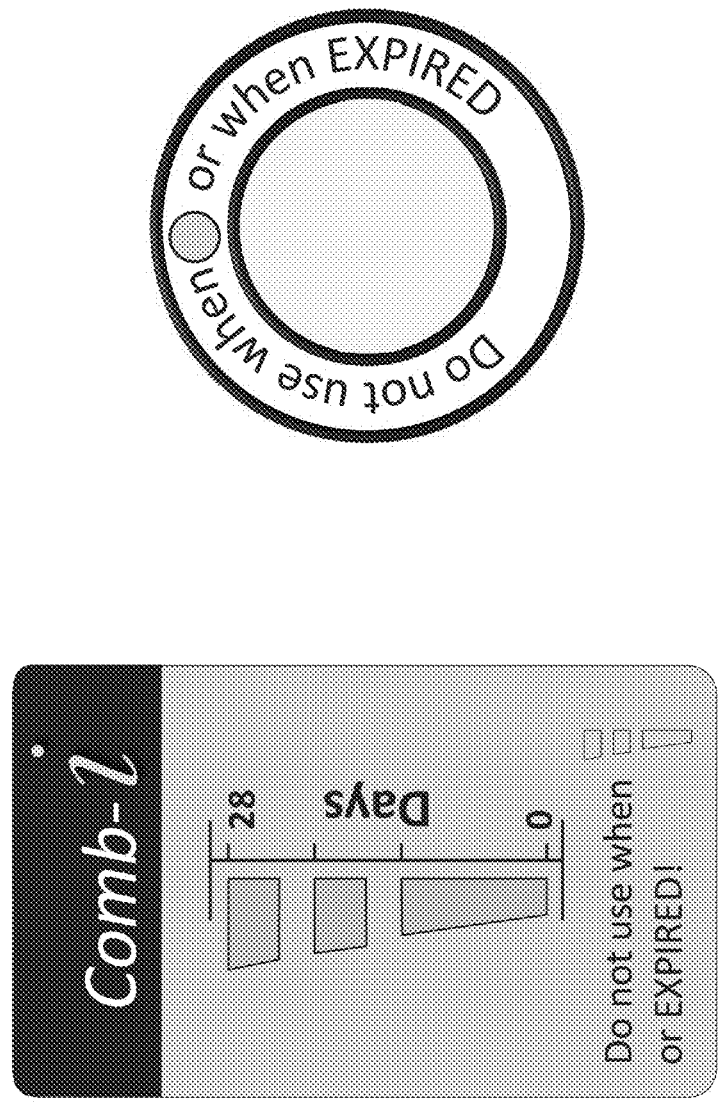
Figure 1B:
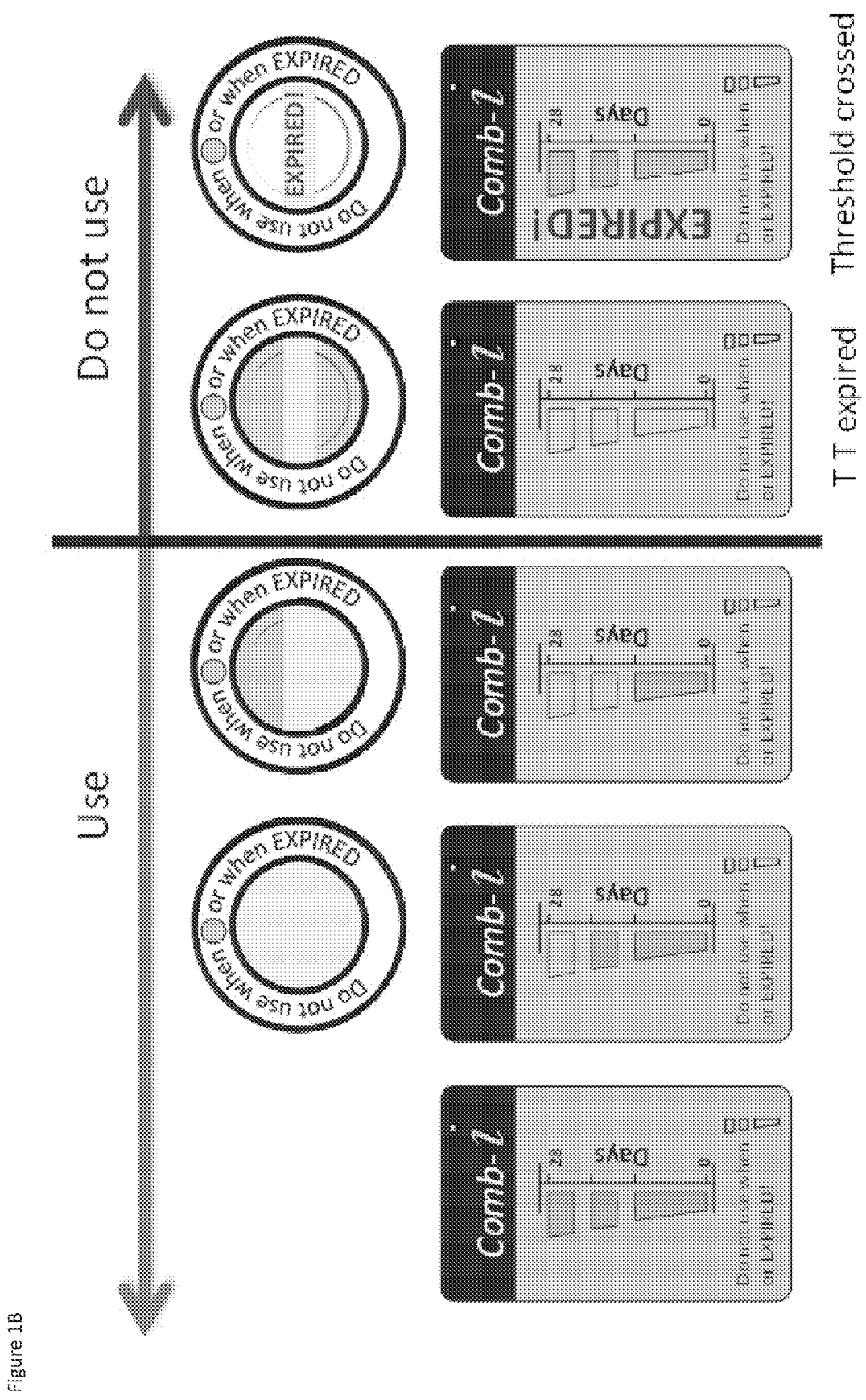
FIG. 1B shows the gradual development of two different examples of TTI combined with TI and FI residing on the same spot (the three panels of the rectangle label and two panels of the round label on the left side), as well as two panels (both for the rectangle and round labels) showing states in which the product should not be used (two panels on the right side)

FIG. 1B shows the gradual development of the TTI history part of the indicator (the three panels on the left side), as well as three panels showing states in which the product should not be used (three panels on the right side), which include such conditions as the threshold having been breached and/or the history showing that a combination of time and temperature indicates that the product should not be used.

FIG. 1C shows a different implementation of the metal based TTI of FIG. 1A-1 according to at least some embodiments of the present invention, with only one barrier layer, with the active layer and passive layer attached to one another in a way that allows activation of the TTI by simply removing a liner barrier and subsequently combining the two labels.

FIG. 3 shows the kinetics of a TTI made of aluminum (OD=0.6) on PET film at 4 C as a function of the water content in a pressure sensitive adhesive layer containing phosphoric acid (PSA) with the phosphoric acid serving as the passive reactant layer. As can be seen, in this case, the TTI's lifespan is shortened when the water content of the PSA increases.

FIG. 4 depicts the color of an active spot of an aluminum (OD=0.6) based TTI having no barrier as a function of the time after activation, while FIG. 5 graphs the color changes.

Figure 6:
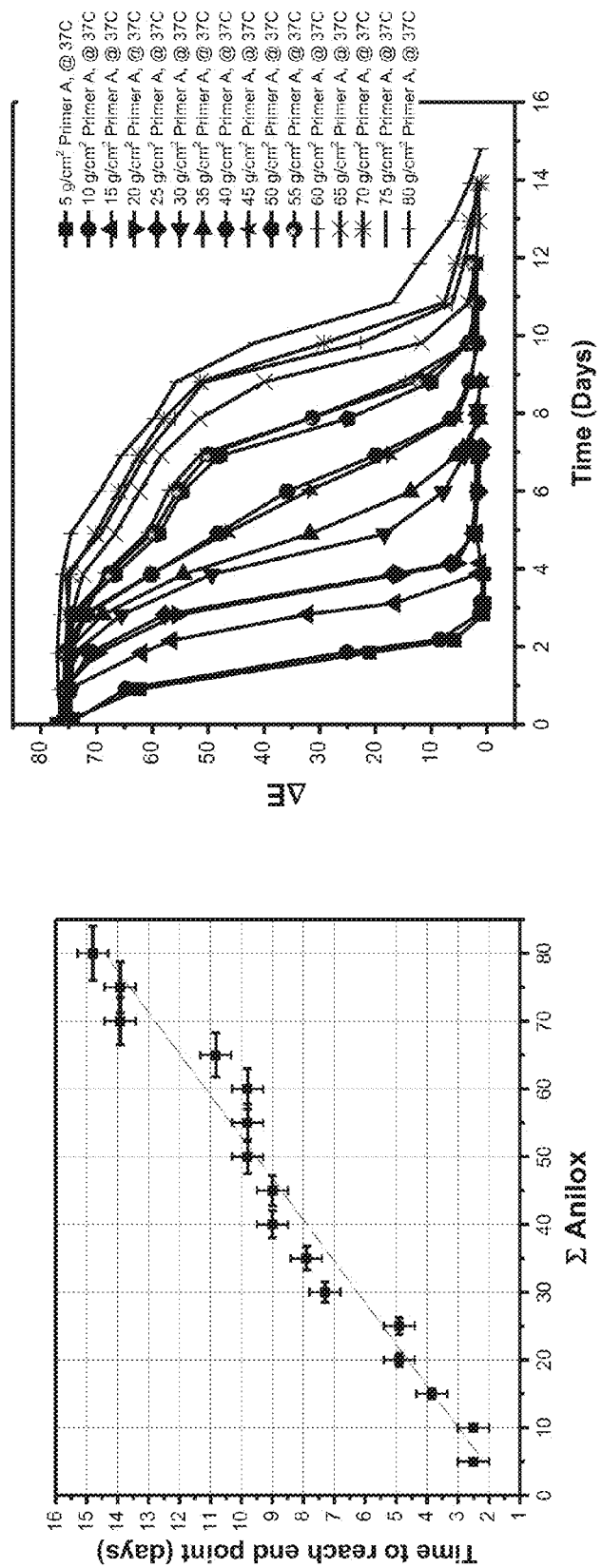
FIG. 6 depicts the time to reach end point as a function of the print thickness (expressed as the sum of anilox size of the printing stations). The graph on the right shows the kinetics of selected points of the graph on the left (color values as a function of the time at 37 C).

FIG. 6 depicts the time to reach end point as a function of the print thickness (expressed in the sum of anilox volumes of the different aniloxes used for printing the barrier). The graph on the right shows the kinetics of selected points of the graph on the left.

Figure 7:
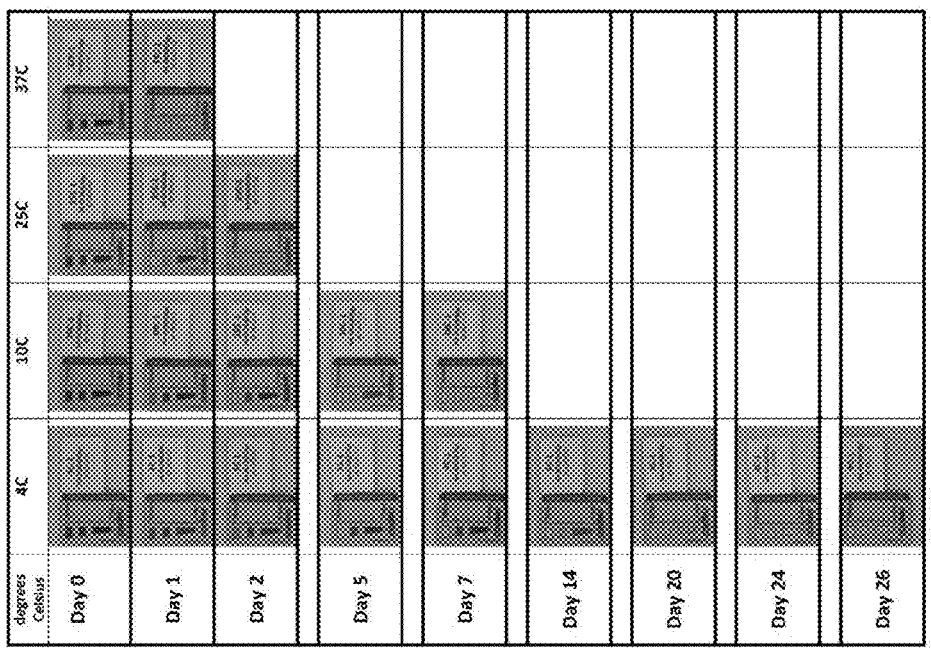
FIG. 7 depicts an embodiment of a three-spot time-temperature indicator having three trapezoid spots, each having a different barrier thickness, at different times after activation, when kept at constant temperatures.

FIG. 7 depicts an embodiment of a three-spot time-temperature indicator having three trapezoid spots, each having a different barrier thickness, at different times after activation, when kept at constant temperatures.

Figure 8:
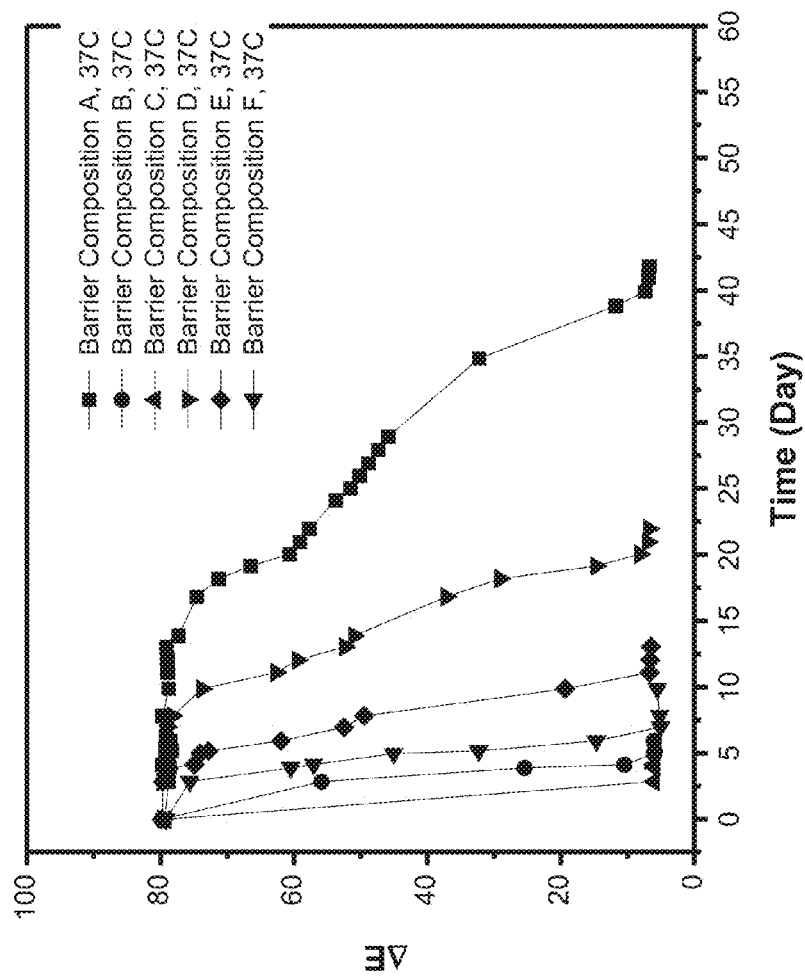
FIG. 8 depicts an example of how printing series of barriers made of the same monomer composition but having different proportions yield different time-temperature behavior of the TTIs.

FIG. 8 depicts an example of how printing series of barriers made of the same monomer composition but having different proportions yield different time-temperature behavior of the TTIs.

TTI Device Based Upon Disappearing Visual Information

Yet another preferred embodiment of a TTI of the present invention exhibits the summary of the elapsed time-temperature in the form of a disappearing signal. FIG. 19A depicts a cross section of a non-limiting, exemplary, illustrative TTI label according to this optional but preferred embodiment. The label is activated, meaning that the etching label was placed in contact with the aluminum label and the time-temperature history is being determined Optionally, if the barrier is printed on top of the aluminum layer with an optical and/or visual indication, then the barrier will show a disappearing signal. In other cases where the barrier is printed above all the region of the aluminum that is seen to the eye there will not be a signal appearing and disappearing. Both have the same cross section but for the purposes of description, FIG. 19A is assumed to show a disappearing signal.

Yet another possibility is to construct the TTI in the form disclosed in FIG. 19B. The label of FIG. 19A normally bears an adhesive on the side of the aluminized film, attached to layer 4 and a liner layer to protect it until adhesion to the product to be monitored. Inspection of the condition of such a label is done normally through the transparent polymer film 10 that is bearing the etchant composition. In the case of the TTI depicted in FIG. 19B the TTI actually bears an adhesive on the side of the film bearing the etchant composition, attached to layer 4 and a liner layer to protect it until adhesion to the product to be monitored. Inspection of the condition of such a label is done normally through a transparent polymer film 6 that is bearing the aluminum layer 5 (layers having the same numbers in FIG. 19B are the same material(s) as in FIG. 19A).

FIG. 20 depicts a non-limiting, exemplary, illustrative TTI with a disappearing signal (visual indication) according to at least some embodiments described herein in which the TTI exhibits the summary of the elapsed time-temperature in the form of a disappearing signal. Specifically, FIG. 20 shows X and V TTI labels according to the embodiment 1) just after activation, 2) after expiry of the first time-temperature segment, and 3) after expiry of the second and last time-temperature segment.

According to this embodiment a metalized (aluminum, PVD, OD=0.6, 6 in FIG. 19) PET film (36 µm, layer 5 in FIG. 19) is coated on the PET side with process yellow (two layers, anilox 10/180, layers 1 and 2 in FIG. 19) then process white (two layers, anilox 10/180, layers 3 and 4 in FIG. 19). Optionally, a layer of aluminum may also be printed after layer 4 to increase light opacity of the back printing. This layer may allow printing of fewer ink layers on the back of the label. The web is then optionally and preferably inverted, and the aluminum side of the label is printed with the desired graphics and pictograms (layer 7 in FIG. 19), to preserve the aluminum. A barrier layer (layer 8 in FIG. 19) is then printed in a way that after activation the active area of the label has a metallic appearance, but without any additional visible shape on it except for pre-printed graphics and pictograms (shown as X1 and V1 in FIG. 20 for the sake of illustration only and without any intention of being limiting).

After a first time-temperature segment, preferably a short one, an aluminum layer that is unprotected by the barrier layer is etched away, revealing all the layers that are protected by a barrier (X2 and V2 in FIG. 20). After a second time-temperature segment the aluminum layer of the TTI label that is covered by the barrier is etched away, revealing a homogeneous yellow background, signaling that the end of the pre-set time-temperature of the label and good to which it is calibrated and thermally coupled (X3 and V3 in FIG. 20). It should be noted that different barrier materials as well as different barrier thicknesses may be used in this embodiment, instilling the label with different lifespans as well as temperature sensitivities (activation energy) for the second time-temperature segment. It should further be noted that the label may be printed with one barrier layer or with a plurality of barrier layers providing segments that disappear one after the other, signaling the consumption of the pre-set time-temperature of the TTI label. It should be further noted that combinations of different barriers as well as different thicknesses may also be used in this embodiment. The barrier layer may be colorless or colored, preferably but not necessarily in the color of the revealing background.

It should be noted that the printing process described above may be performed in other sequences, for example, printing the front of the label first then inverting the web and printing the back. Alternatively, a colored metalized polymer may be used, avoiding the need to print at the back.

Optionally, any TTI of the above examples may be adapted to form an HTTI device, which measures elapsed time-temperature only above a pre-set temperature threshold, or an LTTI device, which measures elapsed time-temperature only below a pre-set temperature threshold, Threshold Indicators As previously described, threshold indicators provide an indication of exposure of the material or device (for example, optionally in the form of a label) to a temperature that is above a threshold temperature. However threshold indicators (TIs) may optionally be combined with freeze indicators (FIs) and/or time-temperature indicators (TTIs). Some non-limiting examples of TIs are described below.

FIG. 2 shows schematic illustrations of only the threshold indicator component alone according to various embodiments of the present invention. FIG. 2A shows a schematic view of a threshold indicator based on crystalline dyes, in which FIG. 2A-1 shows the threshold indicator below threshold temperature and FIG. 2A-2 shows the threshold indicator above threshold temperature.

Figures 2, 2B:
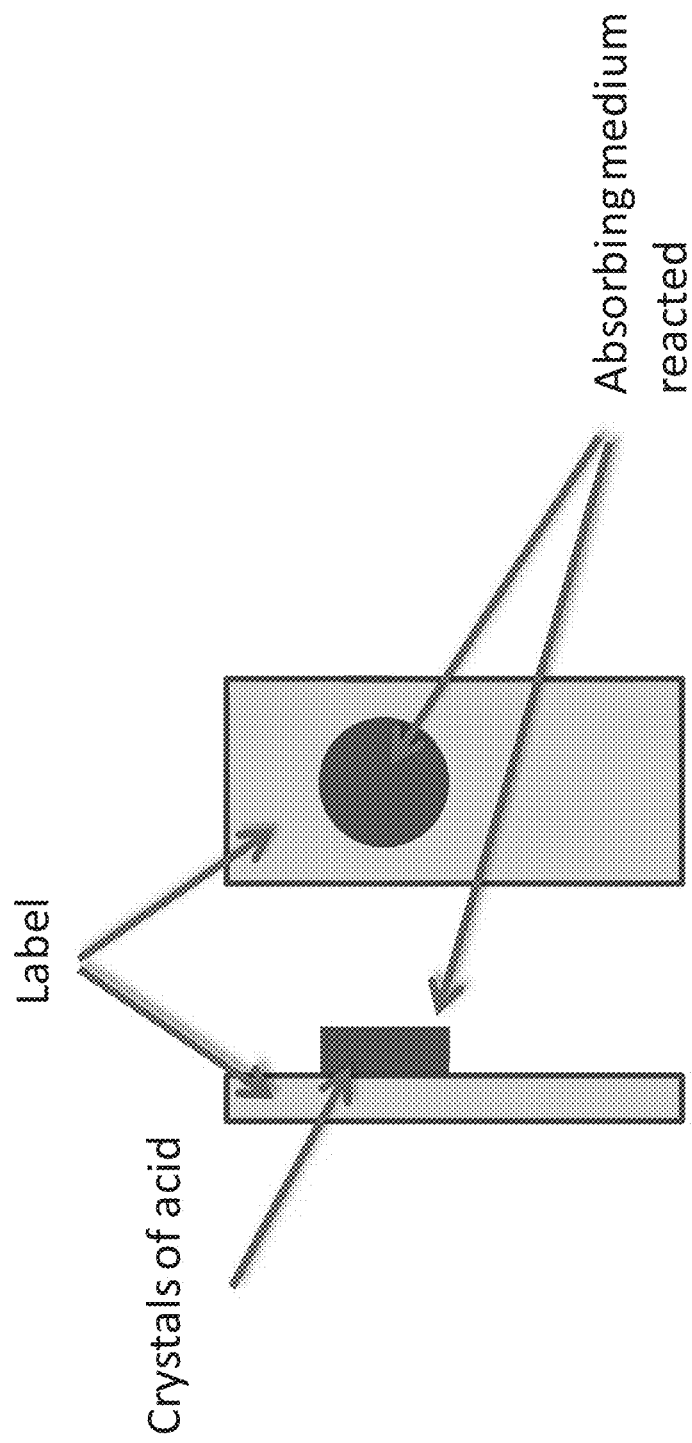

FIG. 2B shows a schematic view of a threshold indicator based on crystalline acid and acid-base indicator on paper, in which FIG. 2B-1 shows the threshold indicator below threshold temperature and in which FIG. 2B-2 shows the threshold indicator above threshold temperature. Non-limiting examples of materials for this embodiment include anthocyanidines, methyl red, and the like.

In both cases, the colors shown are exemplary; it is simply desired that the threshold indicator changes from a first color state to a second color state upon crossing the temperature threshold, in which the first and second color states are different. A color state may optionally be lack of color or a visible color, and/or development of or change in a pattern of a plurality of colors. Examples of preparing the materials for both of these indicators are described with regard to Examples G and H.

FIG. 13 shows a non-limiting, illustrative example of a threshold indicator based upon diffusion. A ~100 micron layer of a mixture of a crystalline material having its melting-point at the desired activation temperature of the TI and a dye is deposited on, or incorporated in, a substrate 1. After the mixture crystallizes, a second layer 2 in the form of an opaque and absorbing fabric (nonwoven polymer, paper etc.) is placed in direct contact with layer 1. These two layers are sandwiched in between two polymer layers, 3 and 6 using adhesive 7 that binds the two layers 3 and 6 all around layers 1 and 2.

Film 3 is optionally and preferably covered at its lower part with an adhesive 4 that enables the label to adhere to a surface, for example and without limitation, of a temperature sensitive good. The adhesive is protected until activation with a release layer (liner) 5 that is normally removed just before application of the label.

Layer 6 is optionally and preferably a transparent film printed with pictograms graphics, using opaque inks, leaving unprinted areas that will form the activation sign upon activation of the label. The film may optionally be translucent as long as the activation area remains optically available, for example visible. Upon activation (crossing the pre-set threshold temperature), the crystals in/on layer 1 melt, and the molten material dissolves the dye. The solution is being absorbed by layer 2, thus coloring it with the dye. This layer becomes visual in the color of the dye through the openings in transparent film 6.

FIG. 14 shows an exemplary label having the layer structure of FIG. 13 before (left) and after (right) activation (i.e. before and after crossing the threshold temperature).

FIG. 15 shows an exemplary, non-limiting illustrative threshold indicator based upon metal etching. A ~100 micron layer of a mixture of a crystalline material having its melting-point at the desired activation temperature of the TI and an etchant, such as phosphorous or phosphoric acid, is deposited on an optionally colored substrate 1. Optionally, after the mixture crystallizes, a second layer 2 in the form of a colored and absorbing and optionally opaque fabric (nonwoven polymer, paper etc.) is placed in direct contact with layer 1. Optionally and preferably, if layer 2 is not present, layer 1 itself (whether inherently or through an added composition on layer 1) and/or an optional layer below layer 1 (not shown) has some type of optically accessible color, which may optionally be the visible light range. For example, a color forming agent may optionally be present in the etching composition (etchant, crystals and dye) or in the carrier of the composition.

These two layers are sandwiched in between two polymer layers, layer 3 (preferably comprising an opaque material, optionally aluminum) and layer 6 (preferably comprising a metallic material which is more preferably aluminum) using adhesive 7 that binds the two layers 3 and 6 around layers 1 and 2. For example, layer 3 may optionally comprise a polymer film covered with aluminum, placed in contact with layer 4. Also for example, layer 6 may optionally comprise a transparent polymer film covered with aluminum, the aluminum layer being placed in contact with layer 2.

In order to form the activation sign, one possibility is to print the surface of the aluminum of layer 6 with an impervious barrier (not shown; a non-limiting example for such a layer is described in greater detail below), leaving as unprinted aluminum only the structure to be revealed. Film 3 is preferably covered at its lower part with an adhesive 4 that is used to adhere the label to surfaces. The adhesive is protected until activation with a release layer (liner) 5 that is normally removed just before application of the label.

FIG. 16 shows the threshold indicator of FIG. 15 in a schematic diagram of an exemplary label, in which a latent visual indication of expiry (that is, of a breach of a temperature threshold) appears upon activation of the label (as shown in the label on the right; the label on the left, before expiry, does not feature this visual indication).

Metal etching, such as aluminum etching as shown with regard to FIGS. 15 and 16, has an advantage over diffusion based TI technologies. Diffusion based TIs feature visual indications of the post-activation information on the label even before activation (see the fleur-de-lis structure in FIG. 14). The only change upon activation is expressed in the color (changing from white to red upon activation). This is a disadvantage, especially when a clear cut "Yes/No" indication is needed for HACCP. In such cases, a label containing a latent sign that is being revealed upon activation, such as in the case presented in FIG. 16, is clearly advantageous.

FIG. 17 shows a TI label having the layer structure of FIG. 15 (in this example without the impervious barrier) before and after activation.

Photonic Crystal Freeze Indicators
Freeze Indicators Based on Freezing of Water Water/Heavy Water Mixtures and Aqueous Solutions The specific technologies described above related to threshold indicators (TIs) which are employed to report temperature excursions to above a pre-set temperature.

These TIs are typically employed for reporting temperature excursions to pre-set temperatures above freezing, particularly for temperatures between 0 to 60 C. The FI technologies described below are employed to report temperature excursions that occur below a pre-set temperature; that is, exposure to a temperature that is below a minimum rather than above a maximum. These FIs are typically employed for reporting temperature excursions to pre-set temperatures above, below or at freezing, particularly for temperatures between −10 to +10 C.

Figure 9:
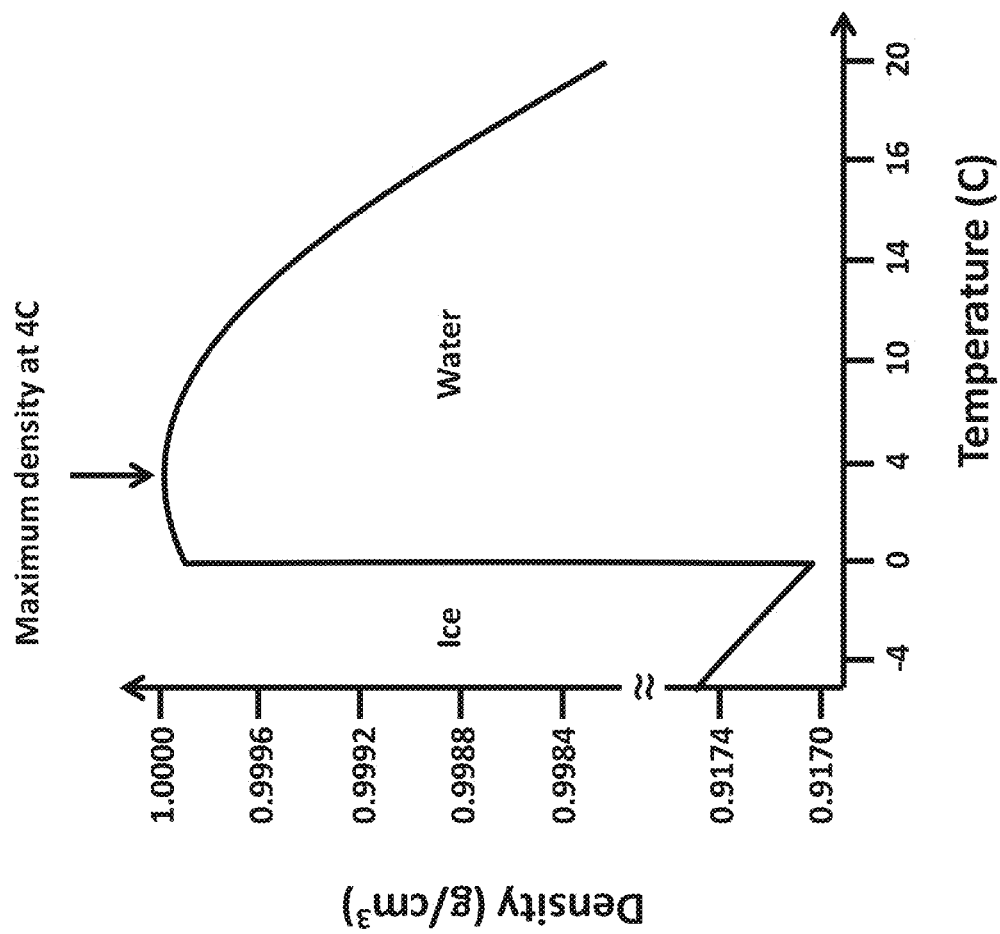
FIG. 9 depicts the density of $H_2O$ as a function of the temperature. This anomalous phenomenon was used in the past for building freeze indicators.

Water is an anomalous solvent having its peak density at 4 C ($H_2O$) and 11.6 ($D_2O$). FIG. 9 depicts the density of $H_2O$ as a function of the temperature. This anomalous phenomenon was used in the past for building freeze indicators. The general concept was based on the fact that water freezes at 0 C and upon freezing expands by ~9%. A sealed container containing water and a dye is placed on an absorbing medium. Upon freezing, water breaks its container and the dye solution stains the absorbing medium in a non-reversible manner.

More specifically, U.S. Pat. No. 4,191,125 to Johnson ("Johnson") discloses a freeze indicator which includes a frangible ampoule substantially filled with a mixture of water, a nucleating agent, and a surfactant. Upon reaching the freezing point of water, the water mixture freezes fracturing the frangible ampoule. According to Johnson a nucleating agent can be used to overcome the undercooling effect; a dye-printed pad can be employed to show a color change; and deuterium oxide may be added to raise the freezing point.

Among the many drawbacks of the abovementioned technology is that its embodiment is in the form of a macroscopic physical device that cannot be produced using low-end and low-cost means. Consequently, the use of such freeze indicators is rather limited. Surprisingly, the present inventors have found that "photonic crystals", a technology related to the light effects of periodically arranged nanometer/micrometer spheres, offers a suitable solution to the goal of producing low-cost freeze indicator labels. Furthermore, optionally this solution obviates the need for any macroscopic liquid container.

Such photonic crystals may also optionally be described as opal structured crystals, which as described herein relate to an ordered structure of object having same or similar size. According to at least some other embodiments of the present invention, there are also provided "inverse opal" structures, which are described in greater detail below.

Preparation of "Opal" Structures:

The preparation of "opal" crystalline assemblies of colloids is reported in the literature (see for example a) N. P. Johnson, D. W. McComb, A. Richel, B. M. Treble, R. M. De La Rue, *Synthetic Metals* 2001, 116, 469-473. b) Y.-J. Lee, S. A. Pruzinsky, P. V. Braun, *Langmuir* 2004, 20, 3096-3106. c) S. Kubo, Z.-Z. Gu, H. Segawa, K. Takahashi, O. Sato, *J. AM. CHEM. SOC.* 2004, 126, 8314-8319. d) G. A. Umeda, W. C. Chueh, L. Noailles, S. M. Haile, B. S. Dunn, *Energy Environ. Sci.* 2008, 1, 484-486. e) O. D. Velev, E. W. Kaler, *Adv. Mater.* 2000, 12, 531-534; all of which are hereby incorporated by reference as if fully set forth herein). Opal is composed of many tiny beads having a similar size, arranged in a crystalline like manner. These references relate to preparation of such structures from many nano/micron size beads.

The general approach to settling (gathering together in a usable format) nano-/micro-meter size beads is by applying a directional force to them, such as a flow of suspending solvent through a filter layer or gravity. This can be done either by using natural gravity or by using a centrifuge. Different materials, such as organic-polymer beads (polystyrene, latex, etc.), emulsion droplets, silica particles, etc., may be used as nano/micro meter size beads. The crystalline structure may be further derivatized by covering the surface with surfactants or polymers or by slight sintering to render the structure stable.

Johnson et al describe a method for preparing opal structures that feature a crystalline structure as follows. Tetraethyl-o-silicate (TEOS) is first hydrolysed and subsequently condenses into silica spheres from "seeds" at a uniform temperature.

Preparation of "Inverse Opal" Structures:

The preparation of "inverse opal" (hereinafter denoting an ordered structure of pores having same or similar size inside a solid and/or semi-solid matrix) is reported in the literature (see for example a) Y. Nishijima, K. Ueno, S. Juodkazis, V. Mizeikis, H. Misawa, M. Maeda, M. Minaki, *OPTICS EXPRESS*, 2008, 16, 13676-13684. b) R. C. Schroden, M. Al-Daous, C. F. Blanford, *Chem. Mater.* 2002, 14, 3305-3315. c) Y-J Lee, P. V. Braun, *Adv. Mater.* 2003, 15, 563-566; d) Stein et al, Chem Mater, 2008, 20, 649-666; e) Umeda et al, Energy Environ Sci. 2008, 1, 484-486; all of which are fully incorporated by reference as if fully set forth herein).

The general approach to make "inverse opal" structures is based on immersing "opal" structures inside a solution containing inorganic polymer-forming monomers, such as tetramethoxy silane, $(CH_3O)_4Si$, zirconium acetate $(Zr(OAc)_4)$, titanium isopropoxide $(Ti(O\text{-}iso\text{-}propyl)_4)$ etc., and applying conditions under which said inorganic polymer-forming monomers polymerize. The "opal" structure is then removed either by calcination at high temperatures (in the case of organic nano/micro meter size beads) or by dissolution (for example, with HF solutions in the case of silica beads), leaving the inorganic polymer outer shell with cavities in place of the nano/micro meter size beads.

Lee et al describe inverse opal hydrogels, formed by using a mixture of 2-hydroxyethylmethacrylate and acrylic acid as the building block for the hydrogel. The precursor or "opal" structure was formed from a polystyrene latex suspension. After photopolymerization of the building block in the template opal structure, the opal structure was removed by dissolution in chloroform.

Stein et al describe inverse opals made from ceria-zirconia materials. These materials are prepared by forming a nanoparticulate sol through a reaction of zirconyl chloride and cerium ammonium nitrate, which is then placed in a template of polystyrene beads in suspension, followed by removal of the beads by application of high temperatures. Thus, various chemical and/or physical reactions are possible to remove the opal template.

FIG. 28A shows an exemplary inverse opal photonic crystal, containing an aqueous solution. FIG. 28B shows an exemplary FI based upon this technology.

FIG. 28A shows an inverse opal photonic crystal containing water having a green color originating from the order and size of the nanocontainers (inverse opal particles (the green color is shown in the circle to indicate how the crystal appears visually). Upon freezing, water shatters the nanocontainers, destroying the three dimensional order of the nanocontainers and associated color (as shown by the colored circle, representing the change in the visual appearance of the crystal).

As shown in FIG. 28B, the following layers are present: layer 1—release tape (liner); layer 2—Adhesive; layer 3—Adhesive; layer 4—a composition containing photonic crystals which may optionally be in the form of an ink, a powder, a paste, a blister containing any of these and so forth; layer 5—a transparent or translucent polymer film; layer 6—(optionally) graphics, colors, pictograms and so forth and layer 7—base polymer film. In operation, the composition in layer 4 changes color (or, more typically, loses color) upon freezing (or at least reduction of the temperature below a low temperature threshold), thereby indicating that the low temperature threshold has been crossed. This change may optionally be determined optically and/or visually.

Unlike many other liquids, water expands in volume around the freezing point, such that upon freezing of water, the resultant volume of crystalline water is larger than the volume available in the container, resulting with the destruction of the container. The destruction of the container serves as an indication of freezing. The liquid inside the container may be died with a dye and the container placed on an absorbing material. The color of the absorbing material may also serve as an indication of freezing.

A major drawback of this technology is that the indicator is a rigid device having a macroscopic volume of water enclosed in a fragile container. This fact is associated with high costs, hazardous fragments of the container, macroscopic volumes of water, rigidity, large volume etc. impeding the application of such devices. Freeze indictors (FIs) that are based on the freezing of water and aqueous solutions may also be made by encapsulating the solution in nano-containers having a narrow size distribution and arranged in high order in two or three dimensions, forming a photonic crystal with the associated color properties.

Freeze indicators (FIs) according to the above description may generally be made of a macroscopic sealed container as described in FIG. 33. The device is composed of a container that contains dyed water or a dyed aqueous solution inside a container 1. The container 1 is usually placed on an absorbing fabric 2. In order to protect the system from any mechanical damage, the device is normally encased in a transparent and shock resistant case 3. Upon freezing, the volume of the frozen water is larger than the volume offered by the container, inducing its disintegration. Upon melting of the frozen water, the dye absorbs into the absorbing fabric, thereby amplifying the freeze signal.

Inverse Viscosity/Inverse Freezing/Inverse Melting Freeze Indicators

TTI and TI Devices Based on Inverse Freezing

Figure 10:
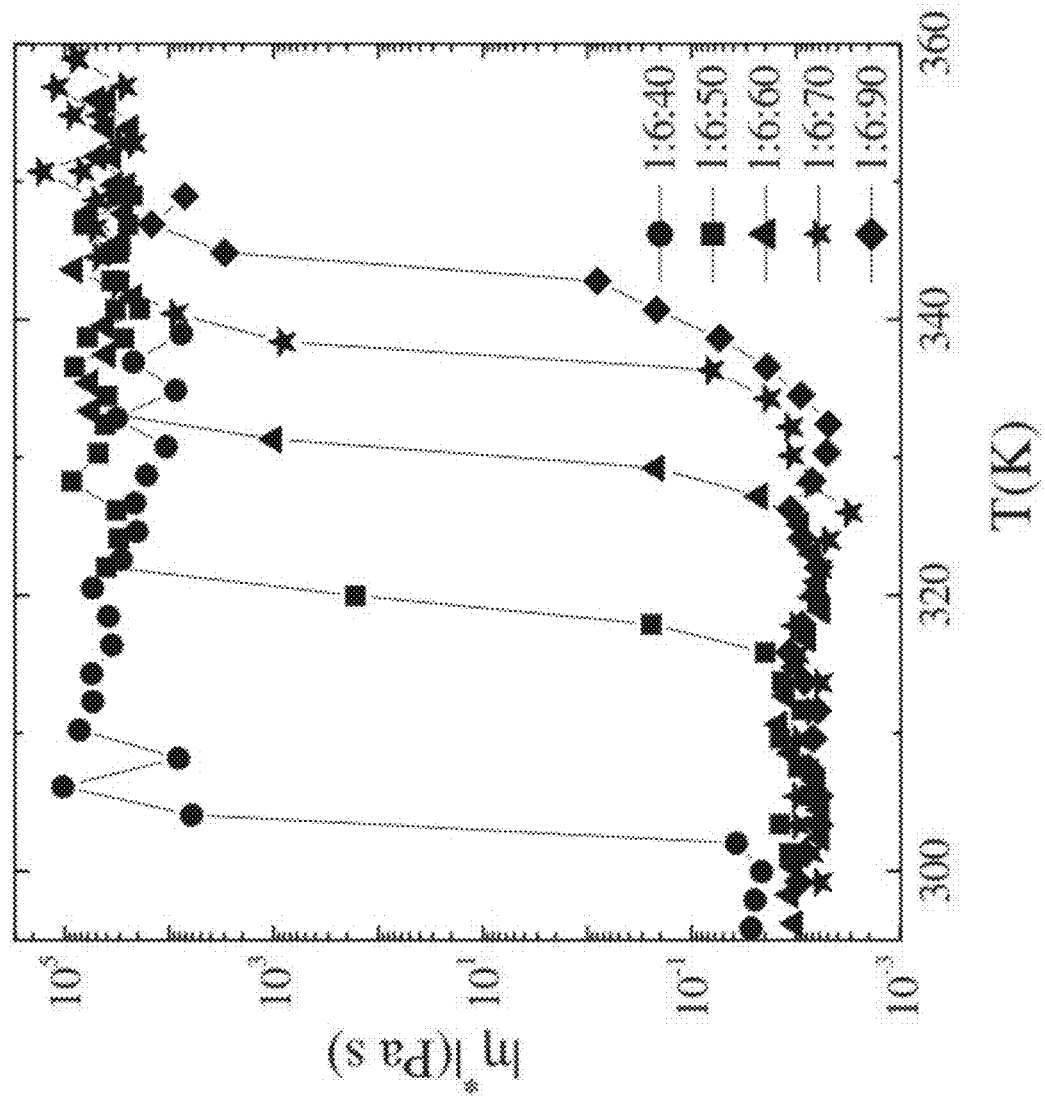
FIG. 10 presents the viscosity of different mixtures of alpha-cyclodextrin (alpha-CD), water and 4-methylpyridine (4MP) (molar ratio provided in graph) as a function of the temperature.

Inverse freezing is a phenomenon in which a material, normally a mixture, undergoes a liquid-to-solid transition upon heating. This transition is normally characterized by an abrupt increase of the viscosity of the system upon heating above a threshold temperature. This phenomenon may be applied to the production of very simple and inexpensive low-temperature threshold indicators, in a way that is similar to the below described upper-temperature threshold indicators of Examples G-I. FIG. 10 presents the viscosity of different mixtures of alpha-cyclodextrin (alpha-CD), water and 4-methylpyridine (4MP) (molar ratio provided in graph) as a function of the temperature. As can be clearly seen from the graph, at low temperatures the mixture is fluid with a viscosity of ~10-2 Pa s. Upon heating the viscosity does not change significantly until approaching a threshold temp. Around this point the mixture exhibits a sharp increase in viscosity and practically solidifies. Upon cooling, this solid "melts" and returns to its fluid nature.

FIG. 18A shows an exemplary inverse freeze indicator (FI) label while FIG. 18B shows this exemplary FI label in a schematic cross sectional diagram.

A ~100 micron layer of an inverse melting mixture (shown as layer 4), optionally containing a dye, having its melting-point at the desired activation temperature of the FI, is deposited on a substrate 3. Optionally, after the mixture crystallizes, a film layer 5 in the form of a perforated and substantially non-absorbing, optionally opaque, polymer film is placed in direct contact with layer 4. An absorbing and optionally opaque absorbing fabric 6 (nonwoven polymer, paper etc.) is placed in direct contact with film layer 5. These three layers 4-5 are sandwiched in between two polymer layers, layer 3 (preferably comprising an opaque material, optionally aluminum film, for example a polymer derivatized with or otherwise comprising aluminum) and layer 7 (preferably comprising a transparent material) which allows visual inspection of the color of layer 6. The layers are preferably attached by using adhesive 9 that binds the two layers 3 and 7 around layers 4, 5 and 6. Layer 8 may be made by printing and contains written information, graphics, logos etc. This printed layer 8 does not necessary cover the entire area of layer 7, optionally leaving unprinted openings for the inspection of the color of layer 6.

Film layer 5 is preferably covered at its lower part with an adhesive 2 that is used to adhere the label to surfaces. The adhesive is protected until activation with a release layer (liner) 1 that is normally removed just before application of the label.

FIG. 29 shows an exemplary technology for a FI based upon inverse melting. Yet another approach to produce FIs is based on the property of some materials and compositions to undergo inverse melting and/or inverse freezing and/or change their viscosity inversely to what most materials do, meaning that their viscosity is, at least in one temperature segment, proportional with the temperature (the viscosity is higher at higher temperatures and lower at lower temperatures). Such materials when cast in a certain shape, will retain their shape until melting (at, around or below a threshold low temperature) or until the viscosity drops to a sufficiently low value to allow fluidity (again, at, around or below a threshold low temperature).

FIG. 29 shows a very simple FI based on inverse melting/inverse freezing system enclosed in a vial. Steps 1-2 (heating the vial to above 30 C until solidification of the material and then inverting the vial) are performed in order to charge the FI. Upon reaching temperatures lower than 30 C, the red solid in the vial liquefies and drops to the bottom of the vial, following gravity.

Non-limiting examples of the preparation of such inverse-freezing indicators are shown in Example J.

Inverse TTI Devices—

One early embodiment of time-temperature indicators includes a porous medium and a colored viscous liquid penetrating into it at a rate that is temperature dependent. The penetration rate is viscosity dependent and this in turn is temperature dependent, normally being low (fluid) at high temperatures and high (viscous fluid or solid) at low temperatures. Interestingly, using composition showing inverse melting one can device an inverse TTI that will "count" elapsed time-temperature in an "inverse" manner, revealing the aggregated time-temperature excursions to lower temperatures. If the inverse freezing composition is characterized by a sharp transition in its viscosity as a function of the temperature the TTI is a partial TTI and reports temperature excursions to temperatures below this transition point.

Inverse melting and/or inverse freezing materials and/or materials that change their viscosity inversely to "normal" materials may also be harnessed to the production of inverse TTI systems, which are able to report the summary of the inverse time temperature count (meaning that they will react more rapidly at lower temperatures and more slowly at higher temperatures). Optionally, such inverse TTI systems are partial TTI, providing the time-temperature history only below a pre-set threshold temperature.

For such TTIs, the active material is optionally enclosed inside the container and the device is inactive until seal is destroyed. The viscosity of the active material is very high at above a pre-set temperature and the device is practically inactive (meaning that the time-temperature count practically halts or is too low to have any practical importance). Upon descending below the pre-set temperature the active material of the device becomes less viscous and starts migrating inside the porous material, the migration distance providing a measure to the (inverse) time-temperature count. The device may be equipped with a scale providing information correlating the migration distance with time at a given temperature or any other useful information.

Figure 30B:
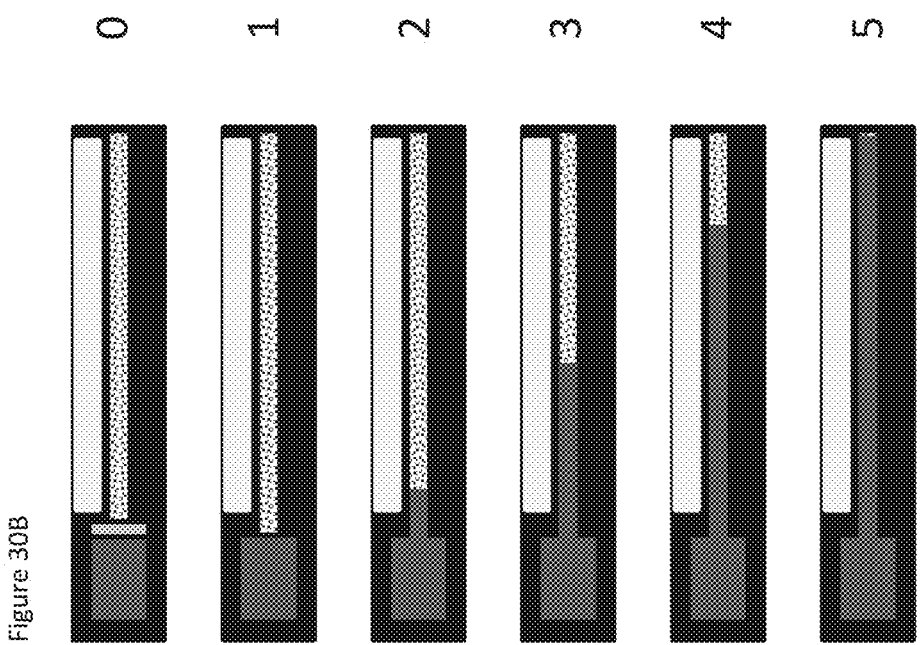

FIGS. 30A and 30B show exemplary inverse TTIs based upon diffusion, in cross section. As shown in FIGS. 30A1 and 30A2, which are schematic diagrams of a cross-section of an exemplary inverse TTI based upon diffusion, a packaging 100 surrounds a porous medium 101 which is separated from an inverse melting material in a container 103 by a destroyable seal 102 (FIG. 30A1). FIG. 30A2 shows an inspection window 104; the inverse melting material from container 103 enters porous medium 101 once destroyable seal 102 is destroyed, thereby providing an optical indication (such as a visual indication for example) of the time temperature history.

FIG. 30B shows the inverse TTI of FIG. 30A before activation (0), after activation (1) and after being exposed to increasing time-temperature doses (2)-(5).

Non-limiting examples of such devices are shown in Example M.

Optionally, any of the above TTI, FI and/or TI devices may be combined in any manner, for example optionally in a single label or even a single device.

Optional Light to Dark TTI

The aluminum etching TTI technology described in the above examples is typically characterized by the transition from metallic shine through a dark layer to the background color (mostly a light color), placed behind the aluminum layer. Some applications require that the color change of the TTI be from a light color to a dark color. Placing a dark color behind the aluminum layer considerably shorten its lifespan, making this solution less desirable for certain applications. For example, as the aluminum starts to disintegrate, it first breaks into small islands that appear black. If put atop a white or light color background the eye sees a superposition of black and light color (say, for white you see gray, starting from almost black just after the islands are formed and ending in white where all the aluminum is etched). If a dark color is used, say black, this appearance is not apparent. It is therefore desirable to have the ability to construct a TTI that is based on metal etching that provides the elapsed time-temperature history from a light color to a dark color.

For both art known TTIs and TTIs described herein, as the time temperature history is determined by the device, a metal etching process occurs, during which the metal layer progresses from a mirror-like layer, through a perforated black layer, to a transparent layer. Based on this aluminum etching process, the visual effect of the active spot of the TTI is from a dark color to a light color, such as, for example and without limitation, bright yellow.

The color change of the TTI described above mainly relies on a combination of light absorption by the black aluminum layer and a reflection from the yellow layer printed under the aluminized layer. As the aluminum layer is being etched away, the contribution of its absorption is reduced, more light reaches the yellow layer and thus more light is reflected from it.

However, sometimes it is desirable for the process of indication/visualization to be reversed, such that the initial color of the TTI is a light color and as time elapses and temperature occurs, the color of the TTI becomes dark.

In the new "Light to Dark TTI" structure a light-diffusive etchant label is used instead of the existing transparent one. This is achieved by coating the same etchant composition as described above on a light-diffusing film with a specific haze value, say for example optionally and without limitation in the range of 25-60% haze values, such that the CIE-Lab color scheme for the active spot has particular values.

FIGS. 31 A-D show schematic block diagrams of exemplary light to dark TTI devices according to at least some embodiments of the present invention. For each figure, a top layer I is the light-diffusing layer and remains constant during all transition phases. A middle layer II is the aluminized film layer (that is, this layer comprises aluminum and a polymer as described above, although of course other materials could be used) and is etched during the transition phases, affecting light transmission and reflectance.

A bottom layer III is the printed color under the aluminum that is gradually revealed through light reflectance as the aluminum is etched.

FIG. 32A shows such an exemplary light to dark TTI device in a label, indicating the effects of elapsed time, showing an activated Light to Dark TTI stored at 50° C. in various stages of transition.

FIG. 32B shows a graph of CIE-Lab color value of the active spot for an exemplary light to dark TTI device, in which the device has a black back color behind the aluminized film and a front hazy PET film as the top layer. The color values are shown as a function of the time after activation (with the device being stored at 60 C).

By contrast, FIG. 32C shows a graph of CIE-Lab color value of the active spot for a TTI device that is "dark to light" as described above, in which the device a process yellow back color behind the aluminized film and a clear (non hazy) PET film as the top layer, with the device being subjected to the same conditions and the graph showing the color values as a function of the time after activation.

Optional Impervious Barrier for FI, TI or TTI Devices

Optionally, an impervious barrier may optionally be added to any device described herein. The impervious barrier is preferably applied to such devices having an etched metallic layer, such as TTI devices described herein. Such devices comprise an aluminum label (or layer) and an activation label (or layer). The activation label contains an etchant that etches aluminum at a rate that is temperature dependent. The aluminum label normally contains active segments, in which the etching process is translated into a visual effect reporting a visual/electrical/optical summary of the elapsed time-temperature. The aluminum label also contains printed areas in the form of pictograms, written information and graphics. Upon placing the activation label atop the aluminum label the etchant starts etching the aluminum layer of the base label.

One side effect of this process is that the aluminum underneath the printed areas is also etched. Although this process is significantly retarded and slowed by the printed ink layer, the etching of the aluminum layer under the graphic represents a serious esthetic drawback and therefore must be prevented.

For that purpose, optionally a protective, printable and UV curable impervious barrier composition may be printed atop non-functional areas of the labels that are devoted to non-changing information, such as pictograms, logo and graphics.

The following is a non-limiting example of an impervious barrier composition and the effect of printing it underneath non-functional areas of the label.

Such an impervious barrier was designed according to the following guidelines:
1) UV-curable ink.
2) Can be printed on the same machine and using the same technology (Flexography) as all other printed layers.
3) Retards significantly the etching process of aluminum by the activation label. In order to retard the etching process, and in view of the fact that the etchant is a polar system (water, phosphoric acid), very hydrophobic building blocks and cross-linker were selected. A non-limiting example that was used to demonstrate the approach is having the following composition:
IBOA (SR506D) 20% W/W
SR368 30% W/W
SR295 40% W/W
Esacure KIP 100F 10% WAY The chemical structures of these molecules are shown in FIG. 21. These molecules may optionally be used for the production (for example, by flexography printing and UV curing) of a non-limiting, exemplary, illustrative impervious barrier for a TTI.

The impervious barrier indeed blocks all etching processes. Due to limited adherence to the aluminum layer as well as to various commercially suitable primers, the impervious barrier is optionally and preferably printed in between the ink layers, more preferably as the third layer above the aluminum (primer, ink I, impervious barrier, ink II, and so forth).

FIG. 22 depicts labels with and without the impervious barrier at different temperatures.

FIG. 23 depicts the CIE-Lab color values of the non-functional yellow part of TTI labels as a function of the time after activation with and without impervious barrier printed under the non-functional areas of the labels. CIE-Lab color values are a specific color scheme determined by the International Commission on Illumination (abbreviated CIE for its French name, Commission Internationale de l'Éclairage).

As can be clearly seen from the graph, the etching of the aluminum layer may be completely blocked by printing an impervious barrier having the above mentioned composition atop it.

Top Coating for TTI Devices

Water imperviousness may optionally be improved by adding a top coating to any TTI device as described herein. For example, optionally a top coating of a PVDC layer may be added to TTI labels for improved water resistance. In many cases, activated labels are used at refrigerated temperatures and come in contact with condensed humidity in the form of water drops. As the top PET layer is not a perfect barrier for water, this water condensation atop the label influences the time temperature count (label kinetics). In order to overcome this limitation the top PET layer was coated with a water impermeable layer in the form of a two micron thick PVDC (Polyvinylidene chloride) layer.

FIG. 24 depicts the kinetics of two TTI labels immersed in water at 4 C, of which one contains a top PVDC coating while the other does not. As can be clearly seen from the graph, labels bearing a PVDC layer are water tolerant and retain their kinetics while the kinetics of uncoated labels are influenced from being immersed in water. Also presented in the graph as a reference two labels, one coated with PVDC and the other uncoated that were placed in an incubator having ~50% relative humidity (RH).

Printing with Flexography

Optionally the above described bather layer may also be produced by deposition, for example by flexography printing, of polymers such as for example alkali soluble polyacrylates, atop the aluminum. For example, a TTI label as previously described, with a layer comprising aluminum, may optionally have an alkali soluble polyacrylate polymer printed atop the active aluminum spot by means of flexography.

FIG. 34 shows the optical density as a function of the time after activation of an aluminized TTI label having an alkali soluble polyacrylate polymer printed atop the active aluminum spot by means of flexography. Specifically, the label has no back printing and the aluminized film is transparent. The labels were stored at a constant temperature of 25 C.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non-limiting fashion. The first set of Examples (Examples A, B, etc) describe various non-limiting examples of optional technologies which may be used. The second set of Examples (Examples 1, 2 etc) describes various business applications of time and/or temperature sensitive devices.

Example A: Freeze Indicator Made of Ordered "Opal" Nanospheres Immersed in Water Mono-dispersed nanometer-sized poly(methyl methacrylate) (PMMA) beads prepared according to a literature known procedure (see for example Y. Xia, B. Gates, Y. Yin, Y. Lu, Adv. Mater. 2000, 12, 693-713 (and references therein). were closely packed by filtration through a filter paper followed by careful slow drying. The ordered bead structures pellets were crushed into powder and immersed in water, avoiding destruction of the close packing order of the beads. The colored powder (color depending on particle size) was then packed inside a thin PMMA coating. Upon freezing, the crystalline structure of the "opal" is destroyed irreversibly and the colored matrix turns white.

Example B: Freeze Indicator Made of Ordered "Inverse Opal" Nanocontainers Containing Water Mono-dispersed nanometer-sized poly(methyl methacrylate) (PMMA) beads, prepared according to a literature known procedure (R. C. Schroden, M. Al-Daous, C. F. Blanford, Chem. Mater. 2002, 14, 3305-3315), were closely packed by filtration through a filter paper followed by careful slow drying. The ordered bead structures pellets were crushed into powder. The powder was then added to a solution of methanol (6.0 mL) and zirconium acetate (solution in dilute acetic acid in ethanol, 6.0 mL). The mixture was allowed to solidify and was further dried in a low temperature oven (60-80 C). Zirconium acetate was converted to zirconia by calcination under air. The same process also removed the PMMA template. The calcination point was reached by heating the sample at a rate of 2 C/min up to 300 C. The sample was kept at 300 C for 2 h, and then the temperature was increased again at a rate of 2 C/min until reaching 450 C. The sample was kept at 450 C for 2 h, and then decreased to ambient temperature at a rate of 5 C/min. The resulting solid was then pulverized, resulting with an "inverse opal" powder having a bright color that depends on the PMMA particle size. The "inverse opal" powder was then immersed in water for several hours, then sealed by enclosing it in a thin PMMA coating.

Upon freezing, the crystalline structure of the "opal" is destroyed irreversibly and the colored matrix turns white, as demonstrated by test results.

Controlling the Freeze Temperature

The temperatures at which aqueous solutions freeze are strongly dependent on the content of the solution. For example, added salts cause the solution to freeze at temperatures that are lower than zero Celsius. FIGS. 11 and 12 depict the effect of added NaCl to the freezing point of water.

It is more difficult to induce freezing of water at temperatures that are higher than zero Celsius. Nevertheless, this can be achieved by mixing water with its isotopologues (HOD and $D_2O$ for any practical use, in which one or more hydrogen atoms are replaced with deuterium). While pure $H_2O$ freezes at 0 C, pure $D_2O$ is reported to freeze at +3.8 C, providing the ability to induce freezing and associated volume expansion at temperatures above the normal freezing point.

Example C: Freeze Indicator Made of Ordered "Inverse Opal" Nanocontainers Containing a Mixture of $H_2O$ with $D_2O$ A freeze indicator made according to example A was prepared using $D_2O$. The freezing temperature of $D_2O$ is +3.8 C while the freezing temperature of $H_2O$ is 0 C. Thus, any freezing temperature in between the two border temperatures may be achieved simply by mixing the two water isotopologues.

Example D: Freeze Indicator Made of Ordered "Opal" Nanocontainers Immersed in a Mixture of $H_2O$ with $D_2O$ A freeze indicator made according to example B was prepared using $D_2O$. The freezing temperature of $D_2O$ is +3.8 C while the freezing temperature of $H_2O$ is 0 C. thus, any freezing temperature in between the two border temperatures may be achieved simply by mixing the two water isotopologues.

Example E: Freeze Indicator Made of Ordered "Inverse Opal" Nanocontainers Containing a Mixture of $H_2O$ with NaCl A freeze indicator made according to example B was prepared using $H_2O$. The freezing temperature of is 0 C while adding salts such as NaCl, KCl, $CaCl_2$ etc. reduces the freezing point of the solution. Thus, any freezing temperature in between at least 0 C and −20 C may be achieved simply by mixing salts with water.

Example F: Freeze Indicator Made of Ordered "Opal" Nanocontainers Containing a Mixture of $H_2O$ with NaCl A freeze indicator made according to example A was prepared using $H_2O$. The freezing temperature of is 0 C while adding salts such as NaCl, KCl, $CaCl_2$ etc. reduce the freezing point of the solution. Thus, any freezing temperature in between at least 0 C and −20 C may be achieved simply by mixing salts with water, and/or optionally by mixing water with an organic solvent such as ethanol, methanol, isopropanol or acetone; combinations of these approaches are also possible. The results of mixing various salts with water are shown in FIG. 11, while the results of mixing the organic solvent methanol or the salt sodium chloride with water are shown in FIG. 12.

Example G: Threshold Indicator—Lauric Acid 1 gr of lauric acid in the form of fine crystals was suspended in water containing 0.1 gr poly (ethyleneoxide)

using vigorous stirring. The solution was filtered using a absorbing medium loaded with a congo-red acid indicator absorbed to it.

The absorbing medium was adhered to the surface of a label with the acid crystalline powder facing the label and the clear side of the absorbing medium facing the viewer.

The label was then put on a heating plate and heated gradually (~0.5 C/min), starting from 22 C, while inspecting the color of the absorbing medium. The color of the absorbing medium was unchanged (slight yellowish color) until a temperature of 44 C was reached. At this point, the absorbing medium develops red spots in points where the crystals of the lauric acid melted. The absorbing medium turned full red within 10-20 sec, depending on the loading of the crystals on the absorbing medium.

Example H: Threshold Indicator—4'-Amino-N-methylacetanilide 1 gr of 4'-Amino-N-methylacetanilide, in the form of fine crystals, was suspended in water containing 0.1 gr poly (ethyleneoxide) using vigorous stirring. The solution was filtered using a filter-paper loaded with a phenol red base indicator absorbed to it.

The filter-paper was adhered to the surface of a label with the acid crystalline powder facing the label and the clear side of the filter-paper facing the viewer.

The label was then put on a heating plate and heated gradually (~0.5 C/min), starting from 22 C, while inspecting the color of the filter-paper. The color of the filter-paper was unchanged (slight yellowish color) till reaching 70 C. At this point, the filter-paper developed red spots in points where the crystals of the 4'-Amino-N-methylacetanilide melted. The filter-paper turned full red within 10-20 sec, depending on the loading of the crystals on the filter-paper.

Example I: Threshold Indicator Based on Melting of Dye Crystals

Example I-1

0.1 gr of E-azobenzene (formula given below) in the form of fine crystals was suspended in water containing 0.01 gr poly (ethyleneoxide) using vigorous stirring. The solution was filtered using a filter-paper.

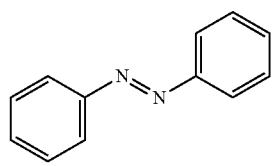

(E)-diphenyldiazene, (E)-Azobenzene

The filter-paper was adhered to the surface of a label with the crystalline powder facing the label and the clear white side of the filter-paper facing the spectator.

The label was then put on a heating plate and heated gradually (~0.5 C/min), starting from 22 C, while inspecting the color of the filter-paper. The color of the filter-paper was unchanged (white) until the temperature of 69 C was reached. At this point, the filter-paper develops yellow-orange spots in points where the crystals of the E-azobenzene melted. The filter-paper turned fully yellow-orange within 10-20 sec, depending on the loading of the crystals on the filter-paper.

Example I-2

0.1 gr of N,N-diethyl-4-[(E)-phenylazo]aniline in the form of fine crystals was suspended in water containing 0.01 gr poly (ethyleneoxide) using vigorous stirring. The solution was filtered using a filter-paper.

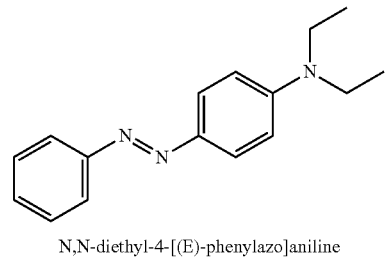 [SMILES: CCN(CC)c1ccc(/N=N/c2ccccc2)cc1]

N,N-diethyl-4-[(E)-phenylazo]aniline

The filter-paper was adhered to the surface of a label with the crystalline powder facing the label and the clear white side of the filter-paper facing the spectator.

The label was then put on a heating plate and heated gradually (~0.5 C/min), starting from 22 C, while inspecting the color of the filter-paper. The color of the filter-paper was unchanged (white) until the temperature of 95 C was reached. At this point, the filter-paper develops yellow-orange spots in points where the crystals of the N,N-diethyl-4-[(E)-phenylazo]aniline melted. The filter-paper turned fully yellow-orange within 10-20 sec, depending on the loading of the crystals on the filter-paper.

Example J: Low-Temperature Freeze Indicators Based on Materials Showing Inverse Freezing Example J-1 One Label System A mixture of 1:6:40 α-cyclodextrin (α-CD), water and 4-methylpyridine (4MP) was stirred at 15 C until homogeneous. Small amount (~1×10$^{-4}$ M) of erythrosine B was added to the solution in order to render it red. The mixture was spread on a polymer film and warmed to 50 C for solidification. The solidified material was covered with a porous non absorbing film. Filter-paper or non-woven polypropylene fabric was then used to cover the spread in a way that hinders the spread from the eye. The indictor was left to cool down at a rate of ~0.1-0.2 C/min upon cooling no change is observes in the appearance of the filter-paper until temperature reached 37 C. At this temperature the spread turns liquid and wets the filter-paper, thus coloring it reddish. The coloration process is completed within seconds.

Example J-2 Two Label System

A mixture of 1:6:40 α-cyclodextrin (α-CD), water and 4-methylpyridine (4MP) was stirred at 15 C until homogeneous. Small amount (~1×10$^{-4}$ M) of erythrosine B was added to the solution in order to render it red. The mixture was spread on a polymer film and warmed to 50 C for solidification. The solidified material was covered with a porous non absorbing film and this was then covered with a siliconized protective layer. This part of the indicator is inactive as it lacks an absorbing medium that its coloration with the dyed fluid denotes temperature abuse. Activation of the indicator is performed by removing the siliconized protective layer and uncovering the solid mixture spread, and then covering it with a filter-paper or another absorbing layer such as non-woven polypropylene layer. The indictor was left to cool down at a rate of ~0.1-0.2 C/min upon cooling no change is observes in the appearance of the filter-paper until temperature reached 37 C. At this temperature the spread turns liquid and wets the filter-paper, thus coloring it reddish. The coloration process is completed within seconds.

Example K—Combined High and Low Temp. Threshold Indicators

Example K-1 One Label System

A mixture of 1:6:40 α-cyclodextrin (α-CD), water and 4-methylpyridine (4MP) was stirred at 15 C until homogeneous. A small amount (~$1\times10^{-4}$ M) of erythrosine B was added to the solution in order to render it red; this substance is optional and may be omitted. The mixture was spread on a polymer film in the form of a circle, warmed to 50 C for solidification.

0.1 gr of 4'-Amino-N-methylacetanilide, in the form of fine crystals, was suspended in water containing 0.01 gr poly (ethyleneoxide) using vigorous stirring. The suspend powder was filtered, dried and placed on the same polymer film bearing the α-cyclodextrin (α-CD), water and 4-methylpyridine (4MP) spread and the system was covered with a porous film.

A phenol red base indicator was absorbed to a filter-paper and the filter-paper was dried. The filter-paper was then adhered to the surface of a polymer film bearing the crystals and spread in a way the filter-paper hinder them from the spectator.

The label was then put on a heating plate and heated gradually (~0.5 C/min), starting from 50 C, while inspecting the color of the filter-paper. The color of the filter-paper was unchanged (slight yellowish color) till reaching 70 C. At this point, the filter-paper develops red spots in points where the crystals of the 4'-Amino-N-methylacetanilide melted. The filter-paper turned full red within 10-20 sec, depending on the loading of the crystals on the filter-paper. A similar label at 50 C was left to cool down at a rate of ~0.1-0.2 C/min. Upon cooling no change is observes in the appearance of the filter-paper until temperature reached 37 C. At this temperature the spread turns liquid and wets the filter-paper, thus coloring it reddish. The coloration process is completed within seconds.

Example K-2 Two Label System

A mixture of 1:6:40 α-cyclodextrin (α-CD), water and 4-methylpyridine (4MP) was stirred at 15 C until homogeneous. A small amount (~$1\times10^{-4}$ M) of erythrosine B was added to the solution in order to render it red; as previously described, this substance is optional. The mixture was spread on a polymer film in the form of a circle and warmed to 50 C for solidification.

0.1 gr of 4'-Amino-N-methylacetanilide, in the form of fine crystals, was suspended in water containing 0.01 gr poly (ethyleneoxide) using vigorous stirring. The suspend powder was filtered, dried and placed on the same polymer film bearing the α-cyclodextrin (α-CD), water and 4-methylpyridine (4MP) spread, and the system was covered with a porous film, then covered with a siliconized protective layer.

This part of the indicator is inactive as it lacks an absorbing medium that its coloration with the dyed fluid denotes temperature abuse. A phenol red base indicator was absorbed to a filter-paper and the filter-paper was dried.

Activation of the label was done by adhering the filter-paper to the surface of the polymer film bearing the crystals and spread in a way that the filter-paper shields them from the spectator.

The label was then put on a heating plate and heated gradually (~0.5 C/min), starting from 50 C, while inspecting the color of the filter-paper. The color of the filter-paper was unchanged (slight yellowish color) till reaching 70 C. At this point, the filter-paper develops red spots in points where the crystals of the 4'-Amino-N-methylacetanilide melted. The filter-paper turned full red within 10-20 sec, depending on the loading of the crystals on the filter-paper. A similar label at 50 C was left to cool down at a rate of ~0.1-0.2 C/min. Upon cooling no change is observes in the appearance of the filter-paper until temperature reached 37 C. At this temperature the spread turns liquid and wets the filter-paper, thus coloring it reddish. The coloration process is completed within seconds.

Example L: Combined Electrical Threshold-Freeze Indicator

As can be clearly appreciated from the above examples, the TI or TTI device may optionally be constructed separately in the form of electrical threshold indicator as well as electrical freeze indicator. It should also be noted that any of the abovementioned threshold indicating examples may be put in between electrodes and be read also through reading any electrical property that changes as a function of the changes to the device that are caused by crossing threshold/freeze limits A non-limiting example is provided below of a one-label combined TTI device.

A mixture of 1:6:40 alpha-cyclodextrin (alpha-CD), water and 4-methylpyridine (4MP) was stirred at 15 C until homogeneous. A small amount (~$1\times10^{-4}$ M) of erythrosine B was added to the solution in order to render it red; as previously described, this substance is optional. The mixture was placed at a small part at the end of an absorbing medium (filter paper, non-woven polypropylene, glass beads or alike) adhered atop an electrically conductive electrode surface and warmed to 50 C for solidification.

0.1 gr of 4'-Amino-N-methylacetanilide, in the form of fine crystals, was suspended in water containing 0.01 gr poly (ethyleneoxide) using vigorous stirring. The suspended powder was filtered, dried, mixed with a very small amount of crystals of a red color pigment and placed at a small part at the end of a second absorbing medium adhered atop the same electrically conductive electrode surface and dried. Both filter-papers were then covered with a second electrode (may be also a transparent electrode).

The label was then put on a heating plate and heated gradually (~0.5 C/min), starting from 50 C, while inspecting the color of the absorbing medium. The color of the filter-paper was unchanged (white) till reaching 70 C. At this point, the absorbing medium bearing the crystals of 4'-Amino-N-methylacetanilide starts wetting in red where the crystals of the 4'-Amino-N-methylacetanilide melted and dissolved the crystals of the red pigment. The red wet part of the absorbing medium gradually expands until it reaches its end and the absorbing medium is completely red. The red color progresses at a rate that is temperature dependent, faster at elevated temperatures. At temperatures around the freezing point of 4'-Amino-N-methylacetanilide and below it the progression of the red color is practically halted. The capacitance and resistance of the system changes as the red color progresses inside the absorbing medium. This allows reading of the excursions above the threshold temperature using any electronic device that is capable of reading capacitance and/or resistance.

A similar label at 50 C was left to cool down at a rate of ~0.1-0.2 C/min Upon cooling no change is observes in the appearance of the absorbing medium until temperature reached 37 C. At this temperature the spread turns liquid and wets the absorbing medium, thus coloring it reddish. At this point, the absorbing medium starts wetting in red where the solid composition became fluid. The red wet part of the absorbing medium gradually expands until it reaches its end and the absorbing medium is completely red. The red color progresses at a rate that is temperature dependent, slower at elevated temperatures. At temperatures around the freezing point of mixture and above it the progression of the red color is practically halted. The capacitance and resistance of the system changes as the red color progresses inside the absorbing medium. This allows reading of the excursions above the threshold temperature using any electronic device that is capable of reading capacitance and/or resistance.

Example M—Inverse TTI Devices

Example M-1 One Label System

A mixture of 1:6:40 alpha-cyclodextrin (alpha-CD), water and 4-methylpyridine (4MP) was stirred at 15 C until homogeneous. A small amount (~1×10$^{-4}$ M) of erythrosine B was added to the solution in order to render it red. The mixture was warmed to 50 C for solidification and then spread atop the end of an absorbing medium strip that was adhered to a polymer film in a way it covers only a small portion of the absorbing medium strip and in places it covers the strip it is spread homogeneously across it. The part of the absorbing medium that is covered with the mixture was then covered with an opaque polymer film in a way the absorbing medium hinder them from the spectator.

The label was then put on a heating plate at 70 C and was left to cool down at a rate of ~0.1-0.2 C/min Upon cooling no change was observed in the appearance of the absorbing medium strip until temperature reached ~37 C. At this temperature the spread turns liquid and wets the absorbing medium strip, thus coloring it reddish. The colored fluid front progresses along the absorbing medium strip at a rate that is inversely temperature dependent so that upon cooling it accelerates and upon heating it slows down and even stops migrating.

Similar embodiments may include a sealed container containing the spread and that inverse TTI activated by pressure or by puncturing the container or by creating openings in it in any way known in the art. Yet another embodiment may include a container residing on an inert support, say a polymer film, with another label containing the porous paper strip in a way that only combining the two initiates the time-temperature count.

Example M-2 Two Label System

A mixture of 1:6:40 alpha-cyclodextrin (alpha-CD), water and 4-methylpyridine (4MP) was stirred at 15 C until homogeneous. A small amount (~1×10$^{-4}$ M) of erythrosine B was added to the solution in order to render it red; this substance is optional as previously described. The mixture was spread on a polymer film in the form of a circle and warmed to 50 C for solidification.

0.1 gr of 4'-Amino-N-methylacetanilide, in the form of fine crystals, was suspended in water containing 0.01 gr poly (ethyleneoxide) using vigorous stirring. The suspended powder was filtered, dried and placed on the same polymer film bearing the alpha-cyclodextrin (alpha-CD), water and 4-methylpyridine (4MP) spread, then covered with a siliconized protective layer. This part of the indicator is inactive as it lacks an absorbing medium that its coloration with the dyed fluid denotes temperature abuse. A phenol red base indicator was absorbed to an absorbing medium and the absorbing medium was dried.

Activation of the label was done by adhering the filter-paper to the surface of the polymer film bearing the crystals and spread in a way the absorbing medium hinder them from the spectator.

The label was then put on a heating plate and heated gradually (~0.5 C/min), starting from 50 C, while inspecting the color of the absorbing medium. The color of the absorbing medium was unchanged (slight yellowish color) till reaching 70 C. At this point, the absorbing medium develops red spots in points where the crystals of the 4'-Amino-N-methylacetanilide melted. The absorbing medium turned full red within 10-20 sec, depending on the loading of the crystals on the absorbing medium. A similar label at 50 C was left to cool down at a rate of ~0.1-0.2 C/min Upon cooling no change is observes in the appearance of the absorbing medium until temperature reached 310K. At this temperature the spread turns liquid and wets the absorbing medium, thus coloring it reddish. The coloration process is completed within seconds.

Example N—Out of Standard Temperature TTI Devices

As can be appreciated from the various examples of TTI devices given in Example M, one can easily combine known normal TTIs (for example, the abovementioned metal based TTI or a diffusion based TTI known in the art) with inverse TTIs (for example, two TTI located side by side, experiencing the same temperature at any given time).

This type of indicator will provide a visual indication of the history of the product to which it is thermally coupled, indicating the time-temperature it experienced outside set temperature boundaries.

Example O—Freeze Indicator

Materials:
α-CD=α-cyclodextrin
2-MP=2-Methyl pyridine=2-Picoline
4-MP=4-Methyl pyridine=4-Picoline
Preparation of Samples:
X-MP and water were added to α-CD in a glass vial at low temperature and stirred until all the cyclodextrin was dissolved.

Results are shown in FIG. 25. As can be seen from the figure, all the compositions are solid at 50 C. At 23 C some of the compositions liquefy while others remain solid. Most compositions are liquid at 0 C while all of them are liquids at −23 C. As can be seen from FIG. 25, one can tune the liquefaction of the medium simply by selecting the members of the composition and their ratio.

Example P—Tests of Threshold-60 V1 Label

This label is a TTI prepared according to the above examples. Its structure is shown in FIG. 26.

The active medium used in this label was characterized by DSC (Differential Scanning Calorimetry). The melting temperature of the mixture of Myristic acid and Erythrosine B was determined Experiment conditions: Melting points were recorded on a PL-DSC (Polymer Laboratories) machine. Calibration of the machine was performed on an Indium standard (mp=156.6° C.). 13.2 mgr of the Myristic acid and Erythrosine B mixture (~2% w/w dye in the acid) were melted and cooled to room temperature, allowing re-crystallization. The mixture was loaded into a metallic capsule and DSC was run at a rate of 0.1 C/min. The observed melting temperature of the mixture is around 55 C The results are presented in FIG. 27.

Next, 16-20 labels were incubated at three controlled temperatures (25° C., 37° C., 50° C.). The labels were photographed every few days with the aim to verify if they activate after incubation at the test temperatures (results not shown). The labels stored at 25° C., 37° C. and 50° C. were not activated for at least 161 days. The surface of the labels stored at 50° C. became wavy, probably because of some deterioration of the polypropylene material and/or ink used for printing. All labels tested were activated when placed at temperatures above the threshold temperature.

Next, four Threshold-60 V1 labels were placed on glass plates and immersed in water baths at 37° C. and 50° C. The labels stored, immersed in water, at 37° C. were stable for at least 109 days. They were not damaged nor activated at any time during storage. The labels remained active and could be activated by heating them to temperatures above the threshold temperature. The labels stored, immersed in water, at 50° C. were destroyed after about 60 days. The upper PP film of the label was destroyed and water penetrated the label interior. The dyestuff was washed out of the labels and the labels lost their ability to be activated. Thus the labels can withstand some immersion in water.

Business Examples

The next set of Examples (Examples 1-4) describes various non-limiting, exemplary business applications of time and/or temperature sensitive devices. Such Examples may optionally be implemented with any of the above described technologies.

Example 1—Promotional Object

According to at least some embodiments, there is provided a promotional object, which is a time and/or temperature sensitive device having a display that features a coupon or other incentive to stimulate a purchase and/or a visit to a commercial location. Non-limiting examples of such a commercial location include a store, a restaurant, a movie theatre, a live performance location, a club and the like. The display may optionally feature the incentive in a single appearance after a set time or with a multi stage appearance, in which the display changes a plurality of times to feature the incentive(s).

The promotional object may optionally take a two dimensional or three dimensional shape. Non-limiting examples of such an object include a label and a card. The promotional object features a display that is capable of displaying a single sign or a plurality of signs. According to at least some embodiments, however, optionally the sign or at least part of the sign is initially concealed upon provision of the promotional object to the user. In other words, optionally the recipient (user) does not initially see the entirety or all of the concealed sign or signs of the display. The user may optionally see other sign or signs, which may optionally be pre-printed on the object, for example to indicate that the display will change at a later time.

Alternatively, according to at least some embodiments, a single sign or plurality of signs may optionally be displayed, for example from receipt of the promotional object by the user, and then gradually disappear.

Optionally, the latent sign may optionally bring its holder a benefit only if the same sign or a complementary sign is present on the object in its non-latent parts (that is, in a part of the object that is immediately visible to the user). Alternatively, the object may optionally contain a plurality of signs that are latent at the time the coupon is issued and are revealed at a rate that is temperature dependent or at a rate that is time and temperature dependent in a way that they form different combinations that lead to different benefits at different time intervals after activation of the object.

As previously described, even if the promotional object comprises both time and temperature sensitive elements, the user may optionally perceive the time sensitive element only, given that the display changes after at least some time has elapsed. Optionally and alternatively, the promotional object may feature only temperature sensitive elements, requiring application of heat and/or cold for the display to change.

Optionally, different promotional objects may feature different signs, indicating different benefits, or alternatively they may feature the same sign, indicating the same benefit. Optionally, only some promotional objects feature a sign or signs indicating a benefit.

The promotional object may optionally be printed with the desired text and/or graphic design, optionally and preferably including the logo and brand name of the issuing body. The display of the promotional object preferably comprises an active area, which can be separate from the printed information or be entirely or partially integrated with it. Depending upon the time and/or temperature sensitive technology used to implement the active area, the active area may optionally comprise a plurality of layers. For example, the active area may optionally comprise a metal layer (a non-limiting example of which is aluminum) and a second layer that contains an etchant that is capable of etching the metal layer at a rate that is temperature dependent or at a rate that is time and temperature dependent.

As the etching process is dynamic, at different time intervals after activation, the coupon offer different benefits to its holder. For example, such an implementation may optionally be used for an object which contains a plurality of signs that are latent at the time the coupon is issued and are revealed at a rate that is temperature dependent or at a rate that is time and temperature dependent in a way that they form different combinations that lead to different benefits.

Without wishing to be limited by a single implementation or a closed list, the at least time lapsed nature of the display, such that the user needs to wait for at least a certain period of time before using the promotional object, enables the issuing entity to ensure that the user cannot use the object before a certain period of time has elapsed. For example and without limitation, if the promotional object included an incentive issued by a store, the user would be required to return to the store (optionally a different branch of the same store) to use the incentive displayed on the object.

A non-limiting, exemplary detailed implementation of such a promotional object is shown in FIG. 35 below. For all of the figures described in Example 1, although a certain number of layers is described, optionally any number of layers may be used.

FIG. 35A depicts schematic top and cross section views of a non-limiting example of a promotional object before activation. Before activation, the object optionally comprises two separate systems, a base label 100 and an activation label 101.

Base label (100) optionally and preferably comprises a polymer film (106) bearing a thin metal layer 105, such as for example, aluminum. Metal layer 105 may be partially covered with colors, pictograms and writing such as logo and information (104), leaving at least one part of the metal layer 105 as an uncoated layer (102). Covered layer (104) may be composed of a single layer of paint or lacquer or polymer. Alternatively, covered layer (104) may contain a plurality of layers of paints and or lacquers and or polymer layers. The polymer film (106) may be printed on its non-aluminized surface (107) with information, such as for example the check or "✓" shape, which remains latent until etching of the aluminum layer had advanced. The polymer film (106) may optionally be further printed and coated with additional layers providing additional latent information, background color etc. (108). Layer (108) optionally comprises a single layer of paint or lacquer or polymer. Alternatively, layer (108) may contain a plurality of layers of paints and or lacquers and or polymer layers. Base label 100 may optionally further comprise and additional layer (109) which comprises an adhesive and a liner material.

Activation label (101) optionally comprises a transparent or semi-transparent, usually colorless polymer layer (110) that bears a thin layer of the metal etching component inside a pressure sensitive adhesive (111).

As a non-limiting example, activation of an object 103 is optionally performed by adhering activation label (101) to the uncoated metal segment (102) of base label (100). The freshly activated object 103 bears a shiny metal surface (102).

Figure 35B:
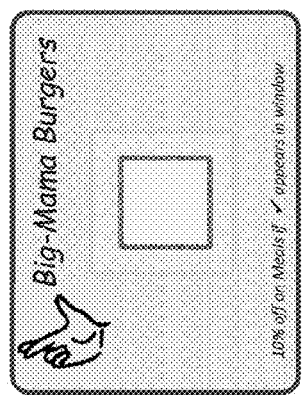
Figure 35C:
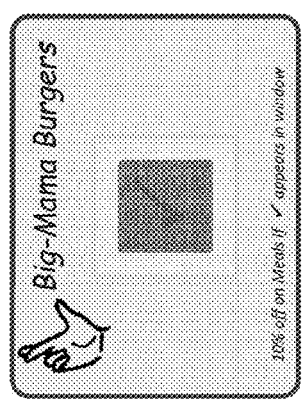
Figures 1, 35C:
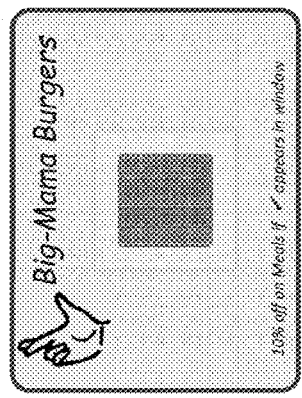
Figure 35D:
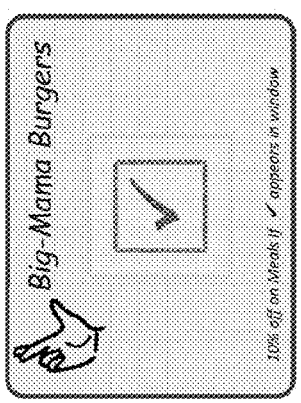
Figures 1, 35D:
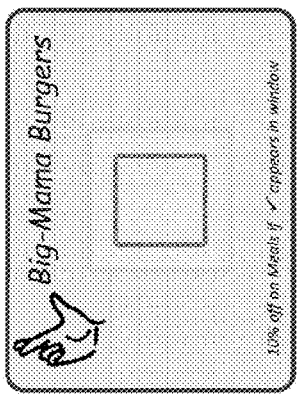

FIGS. 35B-D1 show object 103 with metal layer 105 that is gradually being etched by the metal etching component inside a pressure sensitive adhesive (111). FIG. 35B shows object 103 just after activation. As the metal layer is etched, the latent signal (107) is revealed gradually, as shown in FIGS. 35C and 35D. For comparison, FIG. 35C-1 and FIG. 35D-1 present an object 105 in which the check sign was not printed at the stages that are equivalent to FIG. 35C and FIG. 35D, respectively.

According to at least some embodiments, the promotional object may optionally comprise a sandwich label. For example, the activation label may optionally be attached to the base label in a way that is described above in FIG. 1C.

According to at least some embodiments, the promotional object may optionally comprise an impervious layer under a printed surface. For example, in order to solve the problem of the etchant label etching the aluminum under the printed regions, it is possible to use an impervious barrier layer, described above in FIG. 21 (presenting a non-limiting example of a composition of monomers), FIG. 22 (presenting pictures of labels fresh after activation and after 203 days at 37 C and 50 C) and FIG. 23 (presenting graphs of the yellow color of the labels of FIG. 22 incubated at 37 C as a function of the time after activation).

According to at least some embodiments, the promotional object may optionally comprise a plurality of spots being revealed at different time intervals after activation. For example, FIGS. 6-8 above describe the formation of a plurality of aluminum spots having the same metal layer thickness that are being etched at different temperature dependent or time temperature dependent rates using different light transmissive permeable barrier layers that are printed atop the aluminum layer and serve for altering the etching properties of the aluminum layer by the etchant layer. Such light transmissive permeable barrier layers may be used for creating objects in which the latent information concealed under the aluminum spots are revealed at different time intervals after activation.

Different conditions may optionally apply to the materialization of the object benefit such as giving the object owner the sum of the revealed benefits or giving the object owner the sum of the revealed benefits within a set time limit or giving the object owner the last revealed benefit or alike. For example, FIG. 36 depicts a multi spot promotional object according to at least some embodiments of the present invention, implemented according to the abovementioned technologies. Each of FIGS. 36A-D show a promotional object 120 at different time intervals. FIG. 36A shows object 120 before activation. FIG. 36B shows an initial incentive, in this case 50% off of the product shown in the left most window, as the first display after activation. In FIG. 36C, after a further lapse of at least time, another product is shown in the middle window. In FIG. 36D, after a further lapse of at least time, yet another product is shown in the right most window. The benefit grows with time after activation and the holder is motivated to keep the object and re-visit the store, restaurant or other issuing business location.

For yet another example, FIG. 37 shows a multi spot object made according to the abovementioned technologies according to at least some embodiments at different time intervals after activation but with the provision of only one incentive to the user. In this case, the benefit does not necessarily grow with time after activation and the user is required to decide when is the best time re-visiting the store and materializing the benefit.

According to at least some embodiments, the promotional object may optionally comprise a plurality of spots both appearing (being revealed) and disappearing at different time intervals after activation. FIGS. 6-8 above teach the formation of light transmissive permeable barrier layers that are printed atop the aluminum layer and serve for altering the temporal and temperature dependent evolution of the etching of the aluminum layer by the etchant layer. Such light transmissive permeable barrier layers may be used for creating objects in which the latent information it contains in the aluminum spots is revealed at different time intervals after activation then, at a later stage is erased. FIGS. 38A-C shows an object according to at least some embodiments in which a single spot reveals latent information after a certain time after activation and then after yet another time interval the revealed information fades and disappears. FIG. 39 presents a cross section of a non-limiting example of an object of FIGS. 38A-C.

Before activation, an object 103 preferably comprises two separate systems, base label 101 and activation label 101 as shown in FIG. 39.

Base label (100) optionally and preferably is constructed as described above with regard to FIG. 35A. As previously described, metal layer 105 preferably features an uncovered or uncoated part 102. The uncovered part 102 of the metal layer 105 is preferably printed with a light transmitting permeable barrier layer or layers (109) that is printed atop metal layer 105 and alters the etching properties of metal layer 105 by the etchant layer of activation label 101 (see for example FIGS. 6-8 above).

Activation label (101) is preferably prepared as described above, with a transparent or semi-transparent, optionally colorless polymer layer (110) that bears a thin layer of the metal etching component inside a pressure sensitive adhesive (111).

Activation of object 103 is preferably performed by adhering activation label (101) to the uncoated metal segment (102) of base label (100). The freshly activated base label 100 bears a shiny metal surface (uncoated part 102) that is gradually being etched by the metal etching component inside a pressure sensitive adhesive (111).

Just after activation uncoated part 102 may optionally appear reflective as shown in FIG. 38A. As uncoated part 102 of the metal layer is not fully covered by the permeable barrier layer 109, the uncoated parts of the aluminum are etched faster, revealing a metallic shape in the form of the printed permeable barrier layer 109, as shown in FIG. 38B. After an additional time interval the etchant layer of activation label 101 penetrates the permeable barrier 109 and etches the aluminum layer of uncoated metal part 102 underneath, causing the disappearance of the exposed signal, as shown in FIG. 38C.

FIGS. 40A-D depict a object in which a plurality of spots reveal latent information at different time intervals after activation and then after yet additional time intervals the revealed information exposed in the different spots they fade and disappear. Printing different permeable barriers or the same permeable barrier but at a different thickness on the different metallic parts allows the programming of the order and rate of disappearance of the revealed information. FIG. 41 shows the object of FIG. 40 in cross-sectional detail.

Before activation, the object 103 of FIG. 41 optionally and preferably comprises two separate systems: base label (100) and activation label 101 as previously described. Base label 100 is optionally and preferably constructed as described with regard to FIG. 39; however preferably the background of at least two of the three aluminum spots (uncoated metal part 102) is also covered with a permeable barrier layer 109 in order to allow the latent information concealed in each aluminum spot to be revealed at a different time after activation. If these layers (109) are printed from different compositions or of the same composition but with a different thickness, the different permeable barriers 109 will present different protection against the etching process, resulting in different lifetimes for etching of the same aluminum layer 105 under the different permeable barriers.

Activation label (101) is also preferably constructed as described with regard to FIG. 39.

Activation of the object 103 is performed by adhering activation label (101) to the uncoated metal segment (102) of base label (100). The freshly activated base label 100 bears shiny metal surfaces (102) that are gradually being etched by the metal etching component inside pressure sensitive adhesive (111) of activation label 101. Just after activation uncoated metal segment (102) optionally and preferably appears reflective as shown in FIG. 40A. As the metal layer 105 is covered by different thicknesses of the permeable barrier layer 109, the parts of the metal layer 105 that are coated with the thinnest layer 109 are etched first, revealing a metallic shape in the form of the thicker permeable barrier layer 109 in the spot on the left as shown in FIG. 40B. After an additional time interval the etchant layer penetrates the thinner permeable barrier layer 109 around the thicker permeable barrier layer 109 of the central spot, revealing the second concealed shape, shown in FIG. 40C. At this stage there are two exposed shapes. After yet another time interval, the shapes on the left and central spots are etched, leaving blank spots while the surrounding aluminum layer of the right spot is etched, revealing the third shape, as shown in FIG. 40D. This shape will also disappear with time. The holder of the object may optionally select an incentive at any time, such that waiting for the process to end is no longer the best solution for maximizing profit.

The above embodiments may also optionally be further combined by an appearing signal relying on the use of an impervious barrier, as described in greater detail below, as well as combinations of this embodiment with the above embodiments. Also optionally, the promotion object may be provided in a preactivated form, such that the time and/or temperature sensitive clock has already started running and the time required for any of the above events to occur is already elapsing, also described in greater detail below.

In yet another embodiment the appearing latent signal is achieved through printing an impervious barrier atop the aluminum layer. As this layer is impervious to the etchant, the unprinted surrounding areas of the aluminum layer are etched at a certain time after activation of the promotional object while all the aluminum area that was printed with the impervious barrier are not being etched at any time after activation that is relevant to the purpose of the function of the promotional object.

FIGS. 42A, 42B and 42C show an exemplary promotional object in which a single spot reveals latent information after a certain time after activation and the revealed information fades slowly or does not fade at any time that is relevant to the function of the promotional object. By "relevant to the function of the promotional object" it is meant that the display does not fade during the time period required for the promotional object to display the latent information. FIG. 43 presents a cross section of a non-limiting example of a promotional object of FIG. 42.

Before activation, the promotional object 103 comprises two separate systems as previously described, a base label 100 (prepared as described above) and an activation label 101 (also prepared as described above).

An uncovered part (metal segment) 102 of the metal layer 105 is optionally and preferably covered (for example by being printed, painted, sprayed, coated and so forth) with a light transmissive impervious barrier layer (109) that alters the etching properties of the metal layer 105 by the etchant layer of activation label 101 (see also FIGS. 6-8 above).

Activation of the promotional object 103 is performed by adhering activation label (101) to the uncovered metal segment (102) of base label (100) that is partially covered by the impervious layer (109). The freshly activated base label 100 bears a shiny metal surface (102) as part of metal layer 105. The portions of metal layer 105 that are not covered by impervious layer 109 are gradually etched by the metal etching component inside a pressure sensitive adhesive (111).

Just after activation the metallic area 102 is reflective as shown in FIG. 42A. As the metal layer 105 is not fully covered by the impervious barrier layer (109), the uncoated parts of metal layer 105 are etched while the covered parts are not etched, revealing a metallic shape in the form of the printed permeable barrier layer (109), as shown in FIG. 42B. The revealed form is preferably not etched by the etchant, and hence does not fade or is not destroyed, at any time that is relevant to the function of the promotional object as shown in FIG. 42C.

For some applications of the present technology it is advantageous to have some of the barrier layers (109) as permeable layers that retard the etching process of metal layer 105, while other barrier layers 109 are impervious layers that prevent etching of metal layer 105. In both cases barrier layers 109 preferably are in contact with metal layer 105. The purpose of this embodiment is to increase the complexity of the display of information of which the promotional object 103 is capable.

FIGS. 44A-D show a promotional object 103 in which information is revealed in some spots and remains, while such information is revealed in other spots but disappears within a functionally relevant time period. By "functionally relevant time period" it is meant that the display changes during the time period required for the promotional object to remain functioning, for example to provide information to the user through the visual display. FIG. 45 shows the promotional object 103 of FIG. 44 in cross-section.

Covering the metal segments with different combinations of permeable and impervious barriers allows the programming of the order and rate of appearance and disappearance of the revealed information. Promotional object 103 is constructed as previously described, except that some of the uncovered parts 102 of the metal layer 105 are covered with one or more light transmissive permeable barrier layers 109b (in the present example, also shown as the image in the central segment in FIG. 44).

Other uncoated aluminum segments 102 were printed with impervious layers 109a and 109c (in the present example, also shown as the image in the left segment and the entire right segment in FIG. 44). These printed layers 109a-c atop the metal layer 105 alter the etching properties of the metal layer 105 by the etchant layer of the adhesive label 101 (also described in FIGS. 6-8 above).

In this case the image in the left segment is revealed first, as shown in FIG. 44B. This image is formed by the etching of the bare metal (aluminum in this example) layer segment 102 around an impervious layer 109a so the image does not fade at any time that is relevant to the function of the promotional object 103. The image of the central spot is revealed at a second stage as it is covered by a permeable layer 109b, around the image as shown in FIG. 44C. The image in the central segment will fade and disappear with time as it is printed using a permeable barrier layer 109b. The right aluminum segment 102 will not be etched at any time after activation that is relevant to the function of the promotional object 103 as shown in FIG. 44D.

If promotional object 103 is used for providing incentive(s) such as a coupon for example, the user may optionally not be most rewarded (or incentivized) by waiting for the process to end, but instead may optionally be most incentivized/rewarded by using the promotional object more rapidly.

FIG. 45 presents a cross section of a non-limiting example of a promotional object of FIG. 44.

It should be clear that the rate of the etching process of the aluminum layers by the etchant layers are temperature dependent and so is the etching process through the permeable barrier layers. The implication of this temperature dependence of the process is that refrigeration relents the etching. In many cases, refrigeration of already activated layers to 10 C, 4 C or −18 C, depending on specific compositions, will stall the progress of the promotional object. It is therefore possible, for some applications and for some embodiments, to pre-activate the labels and store them at a reduced temperature so that it is readily available for customers.

High Temperature Activated Promotional Object

The above non-limiting examples related to promotional objects that were solely time dependent or time and temperature dependent. For some applications it is desired to have a promotional object bearing a latent image that is revealed upon crossing a given threshold temperature. Such an implementation may optionally be performed as described in FIGS. 13-14 and the accompanying text (based on melting and diffusion of a material) and/or as described in FIGS. 15-18 and the accompanying text (based on melting of an etchant composition and etching of a layer).

As a non-limiting example, a high temperature activated promotional object based on melting of an etchant composition and etching of a layer may optionally be constructed as described in FIG. 46 (top and cross-sectional views of the promotional object, shown at the right and left, respectively). FIG. 46A presents the promotional object (100) before it is thermally activated. As shown in the top view on the right, promotional object 100 comprises a printed metal surface 150 with two bare metal segments (101) and (102). Optionally any number of bare metal segments may be provided.

The left cross-sectional view of the promotional object 100 reveals its structure. A polymer layer (103) bears a very thin metal layer (for example, aluminum) (104) on its bottom surface and printing and/or graphics on its other (outer) side (not shown; shown as printed metal surface 150 in the right view). The metal layer 104 is layered (as described herein, optionally printed, covered, coated etc) with an impervious barrier (105) except around the portions/shapes (106) to be revealed in each metallic segment (101) and (102) at a later stage.

Metal layer 104 is in contact with an etching layer (107) that hosts two inactivated solid etchants (109) and (110), each characterized by a different activation temperature. Non limiting examples of etching compositions contain phosphoric and/or phosphrous acid, an organic material characterized by having its melting point at the desired activation temperature and possibly a colorant, such as for example a Congo red dye. Such an organic material may be for example myristic acid for segments to be activated around 55 C and undecylic acid for segments to be activated around 29 C.

A porous and absorbing material (108) optionally separates the solid etchants (109) and (110) from the metal layer (104) at the areas that are not protected by the impervious barrier (105). A preferably opaque layer (111) seals the lower side of etching layer 107 (that is, the side not contacting metal layer 104). Optionally, adhesive (112) and liner (113) are placed under the opaque layer (111), rendering the promotional object 100 as a sticky label.

In this non-limiting example, preferably as long as the promotional object 100 is maintained below the melting temperature of the etchant composition having the lowest melting temperature, the promotional object 100 is stable with time and does not reveal any of its latent information. Thus, this non-limiting example represents a temperature only activated promotional object (optionally such objects may be constructed to be activated by low temperatures, for example temperatures below freezing).

FIG. 46B describes the process of activation of the first segment (101). Upon reaching the melting temperature of the lowest melting etchant composition (in this example etching composition (109)), the etching composition (109) liquefies (melts), absorbs into the porous material (108) and comes in contact with the metal layer (104) in parts it is not covered by the impervious barrier layer (105). In this non-limiting example, the metal layer 104 is aluminum. The metal layer 104 is etched, revealing the color of the etchant composition (109) and/or the color of the absorbing material (108) that is soaked with the etchant composition (109). This results with the appearance of a sign of a soft-drink after segment 101 is etched, signaling that the holder of the promotional object 100 won a free soft drink. As the second etchant composition (110) has a higher melting temperature (say 55 C) the metallic segment (102) does not reveal yet its latent information.

FIG. 46C describes the process of activation of the second segment (102). Upon reaching the melting temperature of the highest melting etchant composition (in this example composition 110), the etching composition (110) liquefies, absorbs into the porous material (108) and comes in contact with the metal layer (104) in the part not covered by the impervious barrier layer (105). The metal layer 104 is etched, revealing the color of the etchant composition (110) and/or the color of the absorbing material (108) that is soaked with the etchant composition (110). The etching of segment 102 results in the appearance of a symbol indicating a full meal, indicating that the holder of the promotional object 100 won a free meal. As the first etchant composition (109) has a lower melting temperature (say 29 C) the metallic segment (101) revealed its latent information at a lower temperature and the holder of the promotional object 100 receives both a soft drink and a meal.

As a non-limiting example, a high temperature activated promotional object may optionally be constructed based on melting of a composition and diffusion, as described in FIG. 47 (top and cross section views are shown).

FIG. 47A presents the promotional object (100) before it is thermally activated. The various components are as described in FIG. 46, except that promotional object 100 lacks metal layer 104. Instead, preferably a substantially optically transparent polymer layer (104a) features at least two segments 101a and 101b that are nonprinted, shown as nonprinted segments 106. The remainder of polymer layer 104a is preferably printed, for example with colors, text, images and/or graphics, shown as printed layer 103a. Optionally a further printed layer 105a may be present below polymer layer 104a.

Printed layer 105a is in contact with a layer (107) that hosts two inactivated solid colorants (109) and (110), each characterized by a different activation temperature. Non limiting examples of solid colorants compositions contain an organic material characterized by having its melting point at the desired activation temperature and possibly a colorant, such as for example erythrosine B. Said organic material may be for example an organic acid, an organic alcohol, an organic amine, an organic amide, an organic ester, a hydrocarbon and alike. For example, for segments to be activated around 40 C one can use heneicosane, which is a linear hydrocarbon; and for segments to be activated around 49 C one can use hexadecanol. A porous and absorbing material (108) preferably separates the solid colorants (109) and (110) from the polymer layer (104a), at least under the areas that are not obscured by the printed layers (103a) and/or (105a) within the segments (101a) and (102a).

The shape of the latent image may optionally be formed by destroying the absorbing ability of layer (108) at places where the colorant should not be absorbed, thus forming the desired shape. This may be done, for example by selective absorption of a material at specific parts of layer 108, thereby eliminating the ability of these specific parts to further absorb material. A preferably opaque layer (111) seals layer 107 on the side facing away from layer 105a. Optionally, adhesive (112) and liner (113) are placed under the opaque layer (111), rendering the promotional object 100 as a sticky label.

As long as the promotional object 100 is maintained below the melting temperature of the lowest colorant composition, the promotional object 100 is stable with time and does not reveal any of its latent information. FIG. 47B describes the process of activation of the first segment (101a). Upon reaching the melting temperature of the lowest melting colorant composition (say 40 C, in this example the composition (109)), the composition (109) liquefies and absorbs into the absorbing parts of the porous material (108), revealing the first latent information such as a shape, symbol or image (in this case, a soft-drink) in segment (101a), signaling that the holder of the promotional object won a free soft-drink. As the second etchant composition (110) has a higher melting temperature (say 49 C), segment (102a) does not reveal yet its latent information.

FIG. 47C describes the process of activation of the second segment (102a). Upon reaching the melting temperature of the highest melting etchant composition (say 49 C, in this example the melting temperature of composition (110)), the colorant composition (110) liquefies and absorbs into the absorbing parts of the porous material (108). This process reveals the color of the colorant composition (110) and/or the color of the absorbing material (108) that is soaked with the etchant composition (110). This results in the appearance of a sign of a full meal, signaling that the holder of the promotional object won a free meal. As the second etchant composition (110) has a higher melting temperature, segment (102a) revealed its latent information at a higher temperature; when this higher temperature is reached, the holder of the promotional object 100 receives both a soft drink and a meal.

As can be appreciated, the same general embodiments outlined in FIGS. 46 and 47 may be applied, with possible minor alterations, to construct a low-temperature activated promotional object based on melting of an etchant composition and etching of a layer, as well as for constructing a low-temperature activated promotional object based on melting of a composition and diffusion. The adaptation to activation upon lowering the temperature is achieved by, for example replacing the abovementioned etchant composition with an inverse freezing composition, such as the ones described above, and adding a small amount of an etching base, such as hydroxide salts and alike. Alternatively, this may be achieved by replacing the abovementioned solid colorant composition by an inverse freezing composition that optionally contains a dye.

Example 2—Prize Object

According to at least some embodiments, there is provided a prize object, which is a time and/or temperature sensitive device having a display that features a prize that is won. The prize may optionally be a lottery prize or the like. Optionally, the prize is only indicated as being won on certain prize objects, while other objects may optionally feature a display indicating a consolation prize or no prize. The display may optionally feature the prize in a single appearance after a set time or with a multi stage appearance, in which the display changes a plurality of times to feature the prize(s).

The prize object may optionally be implemented as described in Example 1.

Example 3—Entertainment Object

According to at least some embodiments, there is provided an entertainment object, which is a time and/or temperature sensitive device having a display that features a story in parts or a greeting card that reveals some type of visual indication over time. Such a story and/or visual indication may be described as information. This information can be preprinted or variable; if the latter, optionally the information is controlled by the user.

The entertainment object may optionally be implemented as described in Example 1. Non-limiting examples are shown in FIG. 48 as a greeting card. FIGS. 48A and 48B present a non-limiting example of a greeting card with latent information that is revealed only after some time after activation. For example, the greeting card may be made of a fully printed simple card with a place to add personal words and/or a signature. This part and/or any other part of the greeting card is then covered with a label (100) that is adhered above the part that is to be concealed. The label (100) is composed of a transparent polymer film that is coated with a thin metal layer, such as an aluminum layer, and an adhesive underneath the film. The label (100) is then covered by an activation label that is composed of a substantially transparent film bearing an adhesive layer that contains an etchant capable of etching the metal layer to which it is attached. After a pre-set time/time-temperature the aluminum layer of label (100) is etched and what is concealed underneath is revealed, as shown in FIG. 48B.

As another non-limiting example of an entertainment object, the object may optionally take the form of a multiple choice story. For example, a story is printed with multiple choices; the selected option for the progression of the story is revealed by the reader.

Figure 49A:
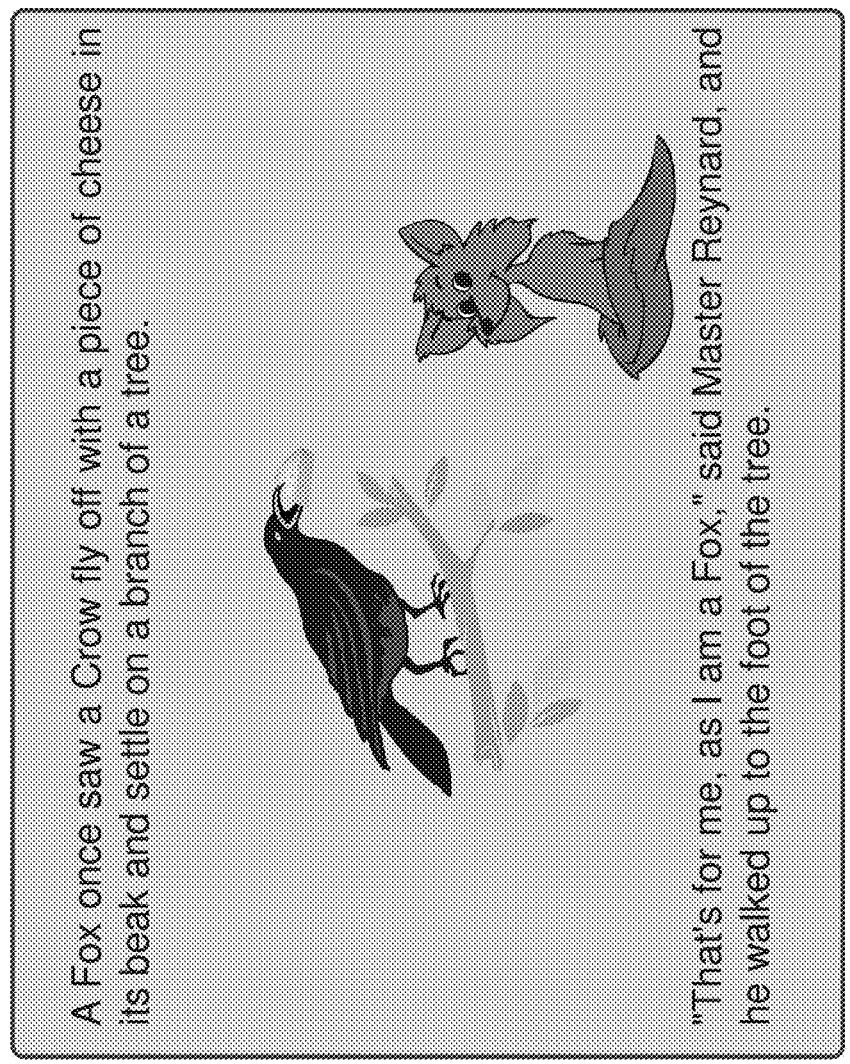
Figure 49B:
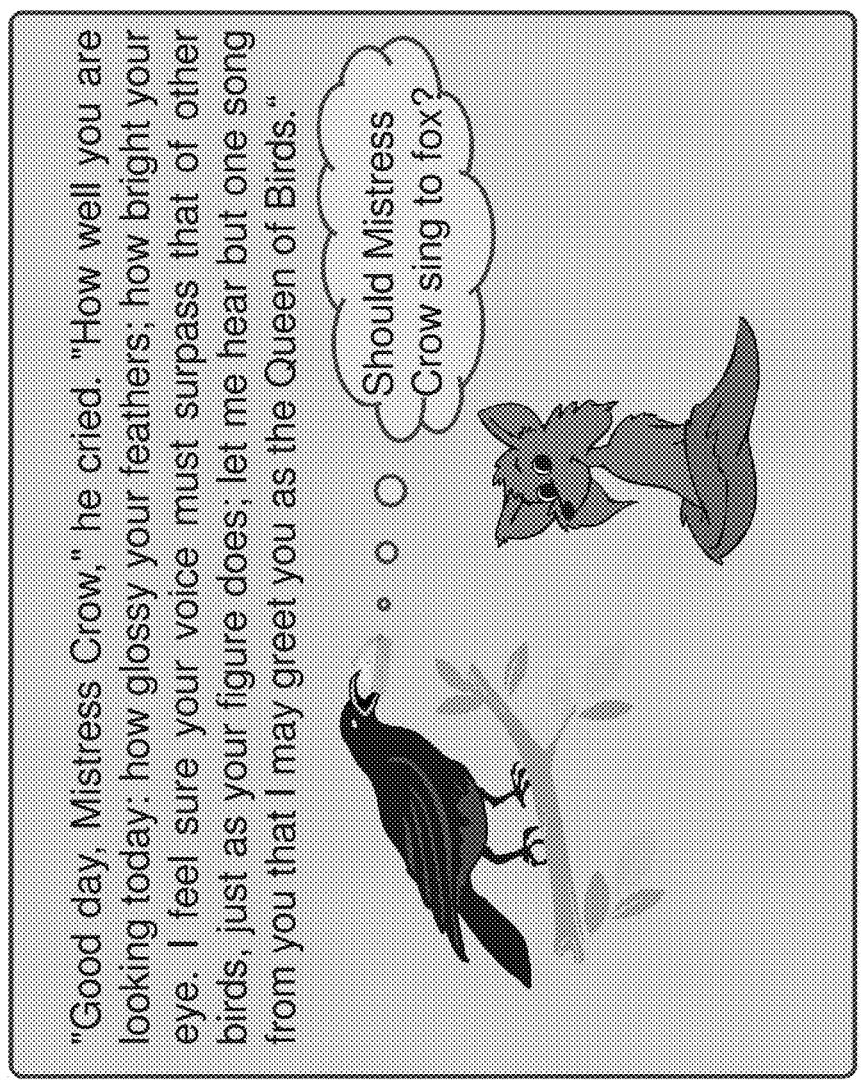
Figure 49C:
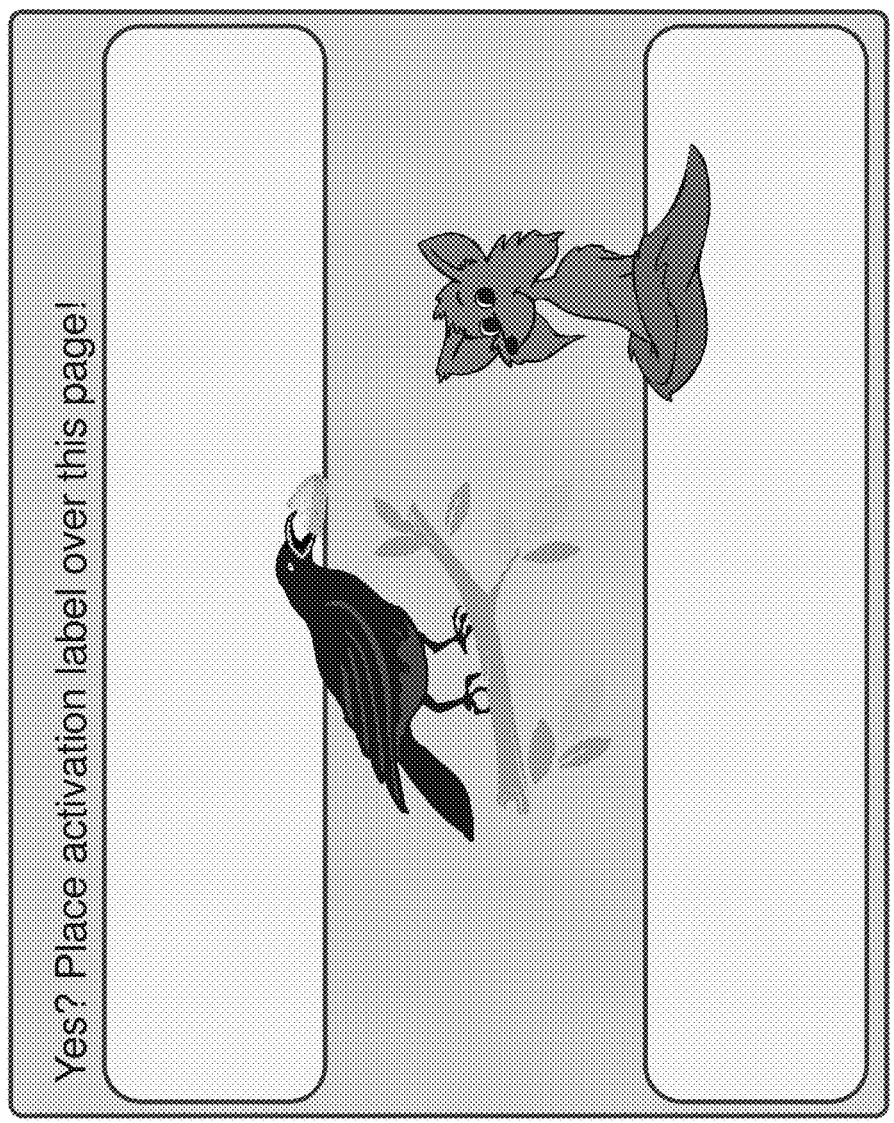
Figure 49D:
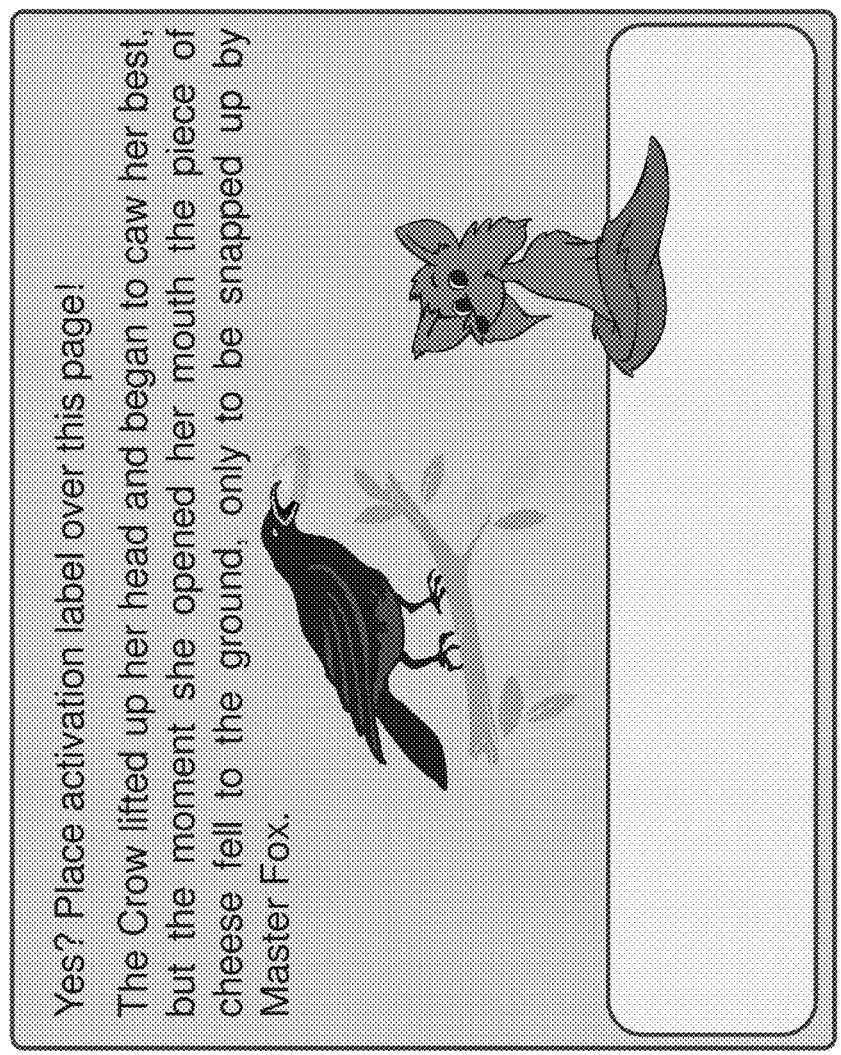
Figure 49E:
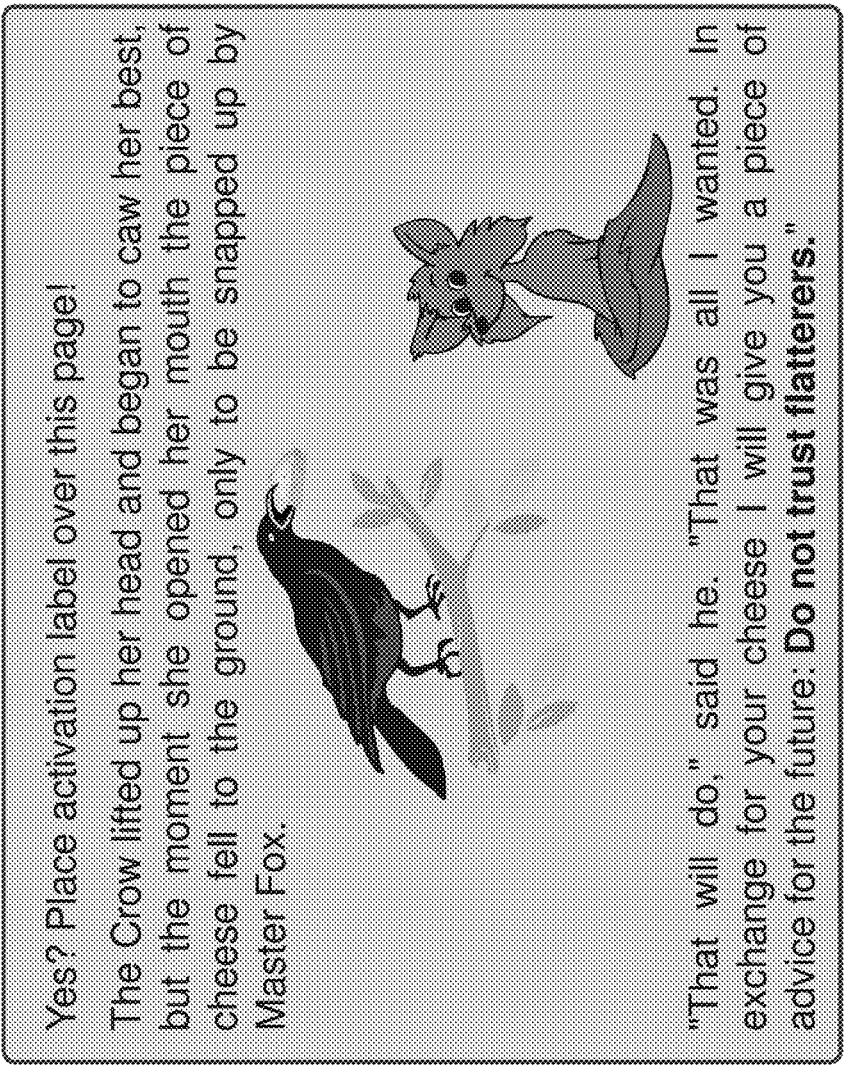
Figure 49F:
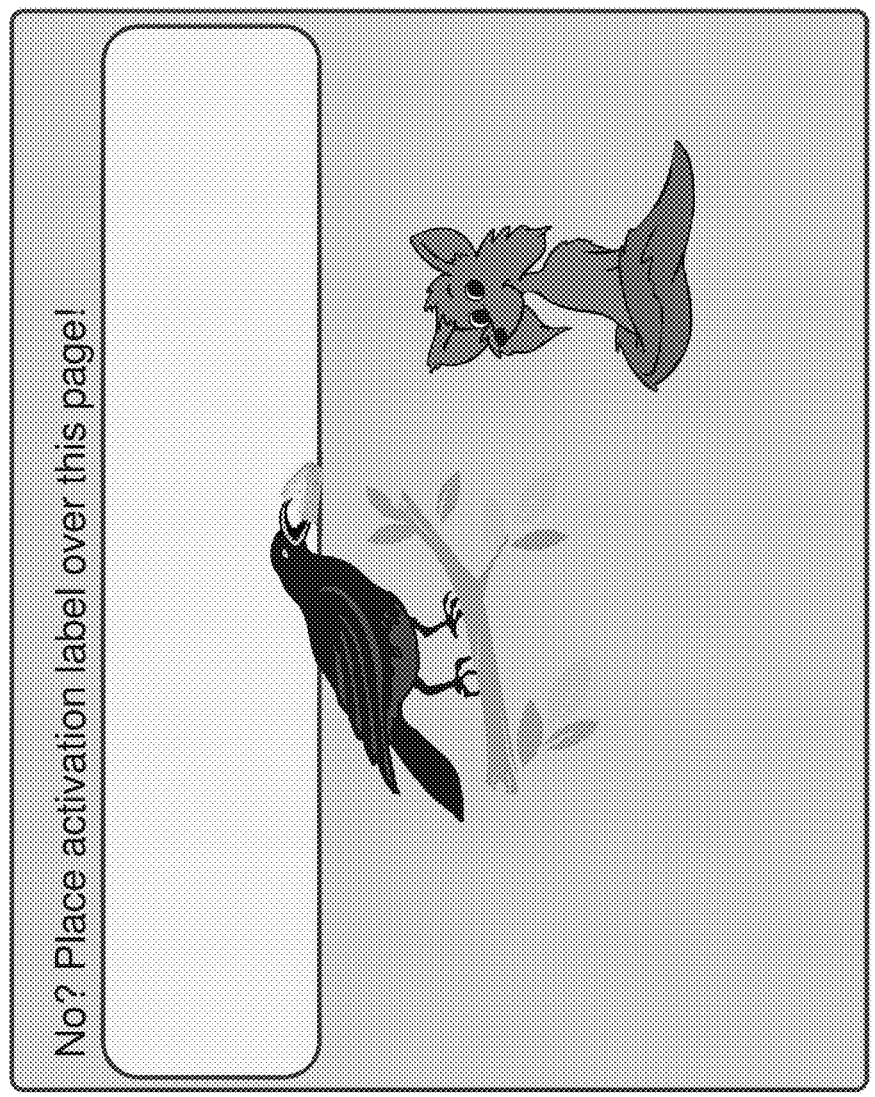
Figure 49G:
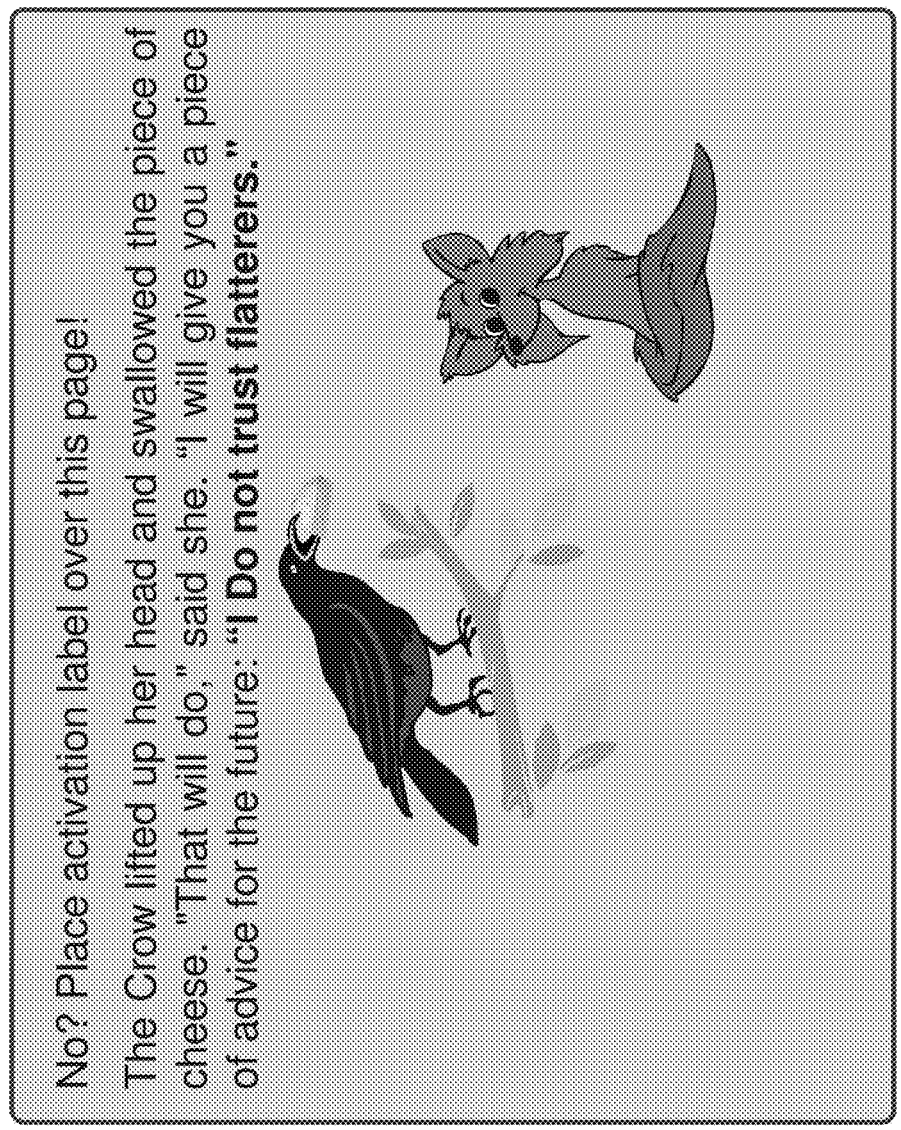

The book may be produced using any of the technologies described above, depending on the desired effects. The present example makes use of the technology outlined in FIG. 35. FIG. 49 shows a short story based on the story "The Fox and The Crow". FIGS. 49A and 49B depict the first two pages of the story. At the end of page two there exist two possible pathways to the enrollment of the story. A positive answer to the question in page two leads to placing an etchant label atop page 3, FIG. 49C. The etchant label etches the aluminum layer concealing the second part of the story according to the chosen scenario, FIG. 49D. The third part of the story is revealed at a later stage, FIG. 49E. Alternatively, a negative answer to the question in page two directs the user to place an etchant label atop page 4, FIG. 49F. The etchant label etches the aluminum layer concealing the second part of the story according to the chosen scenario, FIG. 49G.

Example 4—Time Limited Object

According to at least some embodiments, optionally any of the above embodiments may be combined with a time limitation, such that after a certain amount of time has elapsed, the promotion, prize or entertainment display ceases to display the visual indication. For example, for an incentive such as a store coupon, the user would need to bring the coupon to the store while the visual indication was still being displayed, thereby incentivizing the user to go to the store more quickly. This could be implemented as described for example with regard to FIGS. 40 and 41.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. In an indicator device configured to provide an optical and/or electrical indication that a threshold temperature has been passed, which indicator device comprises an indicator material that exhibits a change in optical and/or electrical properties upon melting, the improvement wherein said threshold temperature is a minimum temperature and said indicator material comprises an inverse melting material, whereby melting of said inverse melting material provides an indication that a minimum temperature threshold has been breached.

2. The indicator of claim 1, wherein said inverse melting material is solid, or undergoes non-linear increase of viscosity, above a certain temperature or above a certain temperature range.

3. An indicator device in accordance with claim 1, wherein said indicator material further comprises a dye.

4. In a time-temperature indicator device that is configured to provide an indication of the elapsed time or time-temperature history of a good to which it is thermally coupled that has occurred over a given period of time within a relevant temperature range, the improvement wherein the relevant temperature range is that below a minimum temperature threshold, whereby the device is an inverse time-temperature indicator device configured to provide an indication of the elapsed time or time-temperature history of a good to which it is thermally coupled over a given period of time at temperatures below said minimum temperature threshold.

5. An inverse time-temperature indicator device according to claim 4, comprising an inverse viscosity material having a viscosity that is proportional to the temperature within said relevant temperature range, such that the viscosity rises as the temperature rises and decreases as the temperature decreases within said relevant temperature range.

6. The indicator device of claim 5, further comprising two conductive layers separated by a porous layer, wherein said inverse viscosity material penetrates said porous layer at a rate that increases with lowering the temperature within said relevant temperature range, and thereby provides an indication to the elapsed time or time-temperature that has occurred at temperatures below said minimum temperature threshold.

7. An indicator device in accordance with claim 5, wherein said inverse viscosity material further comprises a dye.

* * * * *